(12) United States Patent
Matsumoto et al.

(10) Patent No.: US 9,650,565 B2
(45) Date of Patent: May 16, 2017

(54) CARBAZOLE COMPOUND AND USE THEREOF

(75) Inventors: Naoki Matsumoto, Shunan (JP); Takanori Miyazaki, Shunan (JP); Shinichi Ishikawa, Shunan (JP)

(73) Assignee: TOSOH CORPORATION, Yamaguchi (JP)

( * ) Notice: Subject to any disclaimer, the term of this patent is extended or adjusted under 35 U.S.C. 154(b) by 0 days.

(21) Appl. No.: 13/502,834

(22) PCT Filed: Oct. 20, 2010

(86) PCT No.: PCT/JP2010/068469
§ 371 (c)(1),
(2), (4) Date: Apr. 19, 2012

(87) PCT Pub. No.: WO2011/049123
PCT Pub. Date: Apr. 28, 2011

(65) Prior Publication Data
US 2012/0203010 A1 Aug. 9, 2012

(30) Foreign Application Priority Data

Oct. 20, 2009 (JP) ................. 2009-241665
Oct. 20, 2009 (JP) ................. 2009-241666

(51) Int. Cl.
*C07D 209/88* (2006.01)
*C09K 11/06* (2006.01)
(Continued)

(52) U.S. Cl.
CPC .......... *C09K 11/06* (2013.01); *C07D 209/88* (2013.01); *C07D 401/04* (2013.01);
(Continued)

(58) Field of Classification Search
CPC ............. C07D 209/82; C07D 209/88
(Continued)

(56) References Cited

U.S. PATENT DOCUMENTS

| | | | |
|---|---|---|---|
| 7,431,997 B2 | 10/2008 | Hwang et al. | |
| 2005/0221124 A1 | 10/2005 | Hwang et al. | |

(Continued)

FOREIGN PATENT DOCUMENTS

| | | |
|---|---|---|
| JP | 2003-316035 | 11/2003 |
| JP | 2005-154421 | 6/2005 |
| JP | 2006-028176 | 2/2006 |
| JP | 2006-056841 | 3/2006 |
| JP | 2006-151979 | 6/2006 |
| JP | 2006-298895 | 11/2006 |
| JP | 2006-298898 | 11/2006 |
| JP | 2007-520470 | 7/2007 |
| JP | 2008-044923 | 2/2008 |
| JP | 2008-078362 | 4/2008 |
| JP | 2008-195841 | 8/2008 |
| JP | 2009-76817 | 4/2009 |
| KR | 10-2005-0118098 | 12/2005 |
| KR | 2009-0129799 | 12/2009 |
| KR | 2010-0005903 | 1/2010 |
| KR | 2010-0071723 | 6/2010 |
| KR | 2010-0073543 | 7/2010 |
| TW | 200914445 | 4/2009 |
| WO | 2005/040117 | 5/2005 |
| WO | 2005/090512 | 9/2005 |
| WO | 2006/108497 | 10/2006 |

OTHER PUBLICATIONS

STN Results, Yagi et al., WO 2007043484 (2007).*
STN/CAS online results Seo et al., KR 2010071723 (2008).*
STN online search result for Yoshimura et al., JP 2003316035 (2003).*
STN results KR 2010073543, Kim et al., (2010).*
STN results KR 2009129799, Choi et al., (2009).*
Kenichi Goushi et al., "Triplet exciton confinement and unconfinement by adjacent hole-transport layers", Journal of Applied Physics vol. 95, No. 12, Jun. 15, 2004, pp. 7798-7802.
M. A. Baldo et al., "Very high-effidiendy green organic light-emitting devices based on electrophosphorescence", Applied Physics Letters vol. 75, No. 1, May 7, 1999, pp. 4-6.
Applied Physics Letters vol. 82, No. 15 et al., "Blue organic electrophosphoresc using exothermic host-guest energy transfer", Apr. 14, 2003, pp. 2422-2424.
Search Report from International Patent Application No. PCT/JP2010/068469, mail date is Dec. 14, 2010.
Korean Office Action issued in Counterpart Patent Appl. No. 10-2012-7012994, dated Jan. 17, 2017.

*Primary Examiner* — Yong Chu
*Assistant Examiner* — Sonya Wright
(74) *Attorney, Agent, or Firm* — Greenblum & Bernstein, P.L.C.

(57) ABSTRACT

A carbazole compound represented by the following formula:

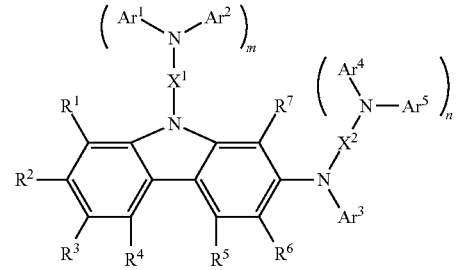

wherein, when m=1, n=0, $Ar^1$, $Ar^2$, $Ar^3$ and $X^2$ are $C_{6-50}$ aryl or $C_{4-50}$ heteroaryl, provided that $Ar^1$ and $Ar^2$, or $Ar^3$ and $X^2$ may form together a ring; $X^1=C_{6-50}$ arylene; $R^1$, $R^2$, $R^4$, $R^5$ and $R^7$ are H, halogen, amino, $C_{1-18}$ alkyl, $C_{1-18}$ alkoxy, $C_{6-50}$ aryl or $C_{4-50}$ heteroaryl, $R^3$ and $R^6$ are H, halogen, $C_{1-18}$ alkyl, $C_{1-18}$ alkoxy, $C_{6-50}$ aryl or $C_{4-50}$ heteroaryl;
when m=0, n=1-3, $Ar^3$, $Ar^4$ and $Ar^5$ are $C_{6-50}$ aryl or $C_{4-50}$ heteroaryl, $Ar^4$ and $Ar^5$ may form together a ring; $X^1=C_{1-18}$ alkyl, $C_{6-50}$ aryl or $C_{4-50}$ heteroaryl; $X^2=C_{6-50}$ arylene; $R^1$-$R^7$ are H, halogen, $C_{1-18}$ alkyl, $C_{1-18}$ alkoxy, $C_{6-50}$ aryl or $C_{4-50}$ heteroaryl;
when m=0, n=0, $X^1=C_{1-18}$ alkyl, $C_{6-50}$ aryl or $C_{4-50}$ heteroaryl; $Ar^3$ and $X^2$ are $C_{6-50}$ aryl or $C_{4-50}$ heteroaryl; $R^2=H$, halogen, $C_{1-18}$ alkyl, $C_{1-18}$ alkoxy; $R^1$ and $R^3$-$R^7$ are H, halogen, $C_{1-18}$ alkyl, $C_{1-18}$ alkoxy, $C_{6-50}$ aryl or $C_{4-50}$ heteroaryl. The carbazole compound is suitable for an organic EL device.

1 Claim, No Drawings

(51) Int. Cl.
  *C07D 401/04*  (2006.01)
  *H01L 51/00*  (2006.01)
  *H05B 33/14*  (2006.01)
  *H01L 51/50*  (2006.01)

(52) U.S. Cl.
  CPC ......... *H01L 51/0072* (2013.01); *H05B 33/14* (2013.01); *C09K 2211/1029* (2013.01); *H01L 51/5016* (2013.01); *H01L 51/5056* (2013.01); *H01L 51/5064* (2013.01)

(58) Field of Classification Search
  USPC .................................................. 548/440, 442
  See application file for complete search history.

(56) References Cited

U.S. PATENT DOCUMENTS

| | | |
|---|---|---|
| 2005/0225235 A1 | 10/2005 | Kim et al. |
| 2006/0020136 A1 | 1/2006 | Hwang et al. |
| 2006/0115680 A1 | 6/2006 | Hwang et al. |
| 2007/0231503 A1 | 10/2007 | Hwang et al. |
| 2008/0107919 A1 | 5/2008 | Hwang et al. |
| 2008/0145708 A1 | 6/2008 | Heil et al. |
| 2008/0254318 A1 | 10/2008 | Nakashima et al. |
| 2008/0284328 A1 | 11/2008 | Nakashima et al. |
| 2009/0066235 A1 | 3/2009 | Yabunouchi et al. |

\* cited by examiner

CARBAZOLE COMPOUND AND USE THEREOF

TECHNICAL FIELD

This invention relates to a novel carbazole compound and an organic electroluminescent device made by using the carbazole compound.

BACKGROUND ART

An organic electroluminescent device (hereinafter referred to "organic EL device" when appropriate) is a planar light emitting device having a structure such that an organic material film is sandwiched between a pair of electrodes, which is characterized as being thin and light-weight, and having a wide viewing angle and a rapid responsibility, therefore, the organic EL device is expected to be widely used for various display devices. Recently, the organic EL device is being utilized for display of cell phones and others.

Organic EL devices are devices utilizing a function of emitting light upon recombination of holes, injected from an anode, with electrons injected from a cathode. Typical organic EL devices have a multilayer structure comprising a hole transport layer, an emitting layer, an electron transport layer and others. The hole transport layer and the electron transport layer are layers having a charge-transporting function, but not having a light-emitting function. More specifically the hole transport layer and the electron transport layer have a function of promoting charge-injection into the emitting layer, and confining charges injected in the emitting layer as well as energy of excitons generated in the emitting layer. Therefore the charge-transport layers play very important role for reducing the drive voltage of the organic EL device and enhancing the luminous efficiency.

As a hole transport material, amine compounds having appropriate ionization potential and hole transportability are used. For example, 4,4'-bis[N-(1-naphthyl)-N-phenylamino] biphenyl (NPD) is well known as such amine compounds. However, NPD has a low glass transition temperature (Tg) and is readily crystallized under high temperature conditions, therefore, organic EL devices made by using NPD have a problem in durability. More specifically organic EL devices having a hole transport layer comprising NPD exhibit high drive voltage and low luminescent efficiency. Therefore, new improved materials are eagerly desired.

In recent years, an organic EL device having an emitting layer comprising a phosphorescent material is being developed. In the phosphorescent device, a hole transport material having a high triplet level is required. NPD is not satisfactory as the hole transport material for phosphorescent device. For example, it is reported that an organic EL device comprising NPD and a green phosphorescent material exhibits a low luminous efficiency (see, for example, non-patent document 1).

Recently, amine compounds having one or more carbazole rings in the molecule are reported as having a high triplet level as compared with that of NPD, and exhibiting good hole transportability. However, heretofore proposed amine compounds having a carbazole ring or rings have a chemical structure such that a nitrogen atom is bonded to 3-position of a carbazole ring (see, for example, patent documents 1 through 7). 3-Position of a carbazole ring is a para-position to the electron-donating nitrogen atom of the carbazole ring, therefore, an amino group introduced in 3-position of the carbazole ring is readily activated by the nitrogen atom of the carbazole ring. Thus, the amine compound having a carbazole ring or rings having an amino group introduced in 3-position of the carbazole ring or rings exhibits a low ionization potential as compared with that of the conventional amine compound. When the heretofore proposed amine compounds having a 3-amino-substituted carbazole ring or rings are used for a hole transport layer of an organic EL device, it becomes difficult to inject holes into an emitting layer, therefore, drive voltage of the organic EL device is inevitably increased.

In view of the foregoing background, an amine compound having a carbazole ring or rings having an amino substituent at 2-position of each carbazole ring is expected to exhibit an appropriate ionization potential. As examples of the amine compound having a 2-amino-substituted carbazole ring or rings, 2-ditolylaminocarbazoles are known as a charge transport material used in an organic photoconductor (see, for example, patent document 8). However, the 2-ditolylaminocarbazoles have a low glass transition temperature and, in the case when the 2-ditolylaminocarbazoles are used in an organic EL device, the organic EL device has a problem such that the durability is poor when the device is operated at a high temperature.

7-Phenyl-2-aminocarbazole compounds for use in organic electronic devices are proposed in, for example, patent document 9. Regarding these compounds having a chemical structure such that a phenyl group is bonded to 7-position of the carbazole ring, i.e., a para position to the amino group in the carbazole ring, since π-electron conjugation in the carbazole ring is extended, and the energy gap of molecule becomes small and the electron affinity is enhanced. Thus, in the case when the 7-phenyl-2-aminocarbazole compounds are used for a hole transport layer of an organic EL device, charges injected in the emitting layer and energy of excitons generated in the emitting layer become difficult to be confined in the emitting layer, and the luminous efficiency is lowered. Further, the 7-phenyl-2-aminocarbazole compounds exhibit a low triplet level, and therefore, an organic EL device comprising a phosphorescent material exhibiting a green light emission in combination with the 7-phenyl-2-aminocarbazole compounds do not exhibit a sufficient luminous efficiency.

Further, other types of carbazole compounds such as 4,4'-bis(9-carbazolyl)biphenyl and 1,3-bis(9-carbazolyl)benzene for use as a host material in an emitting layer are proposed in, for example, non-patent documents 2 and 3. These compounds have a high triplet level, but, exhibit high crystallinity and, when a thin film is formed therefrom, they are readily crystallized, and therefore, an organic EL device comprising these compounds have poor durability.

PRIOR ART DOCUMENTS (1) Patent Documents
Patent Document 1: JP 2005-154421 A
Patent Document 2: JP 2006-028176 A
Patent Document 3: JP 2006-056841 A
Patent Document 4: JP 2006-151979 A
Patent Document 5: JP 2006-298895 A
Patent Document 6: JP 2006-298898 A
Patent Document 7: JP 2008-044923 A
Patent Document 8: JP 2003-316035 A
Patent Document 9: WO 2006/108497 A
(2) Non-Patent Documents
Non-Patent Document 1: Journal of Applied Physics, 2004, vol. 95, p 7798

Non-Patent Document 2: Applied Physics Letters, 1999, vol. 75, p 4

Non-Patent Document 3: Applied Physics Letters, 2003, vol. 82, p 2422

SUMMARY OF THE INVENTION

Problems to be Solved by the Invention

Objects of the present invention are to provide a novel carbazole compound, and to provide an organic EL device exhibiting high luminous efficiency and having enhanced durability.

Means for Solving the Problems

The inventors conducted extensive researches and found that a carbazole compound represented by the following general formula (1), shown below, has good hole transport characteristics, and further that an organic EL device having a hole transport layer comprising the carbazole compound exhibits a low drive voltage, and has high luminous efficiency and enhanced durability. Based on these findings, the present invention has been completed.

Thus, in accordance with the present invention, a carbazole compound represented by the following general formula (1), and an organic EL device comprising the carbazole compound of the formula (1) are provided.

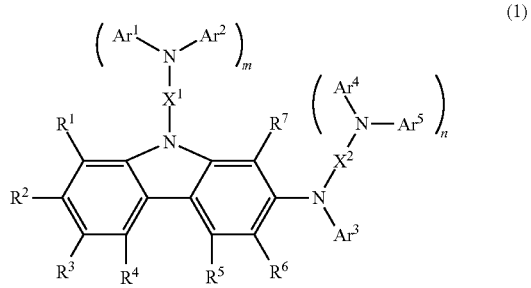

In the formula (1), m represents an integer of 0 or 1, and n represents an integer of 0 to 3, provided that, when m is 1, n is 0; and

[i]. in the case when m is 1 and n is 0, $Ar^1$, $Ar^2$, $Ar^3$ and $X^2$ independently represent a substituted or unsubstituted aryl group having 6 to 50 carbon atoms or a substituted or unsubstituted heteroaryl group having 4 to 50 carbon atoms, provided that $Ar^1$ and $Ar^2$ may be bonded together to form a ring with the nitrogen atom to which $Ar^1$ and $Ar^2$ are bonded, and $Ar^3$ and $X^2$ may be bonded together to form a ring with the nitrogen atom to which $Ar^3$ and $X^2$ are bonded;

$X^1$ represents a substituted or unsubstituted arylene group having 6 to 50 carbon atoms;

$R^1$, $R^2$, $R^4$, $R^5$ and $R^7$ independently represent a hydrogen atom, a halogen atom, a substituted or unsubstituted amino group, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms; and $R^3$ and $R^6$ independently represent a hydrogen atom, a halogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms, provided that, when at least one of $R^3$ and $R^6$ is a substituted aryl group having 6 to 50 carbon atoms or a substituted heteroaryl group having 4 to 50 carbon atoms, an amino group is excluded from the substituent in the aryl or heteroaryl group;

[ii]. in the case when m is 0 and n is an integer of 1 to 3, $Ar^3$, $Ar^4$ and $Ar^5$ independently represent a substituted or unsubstituted aryl group having 6 to 50 carbon atoms or a substituted or unsubstituted heteroaryl group having 4 to 50 carbon atoms, provided that $Ar^4$ and $Ar^5$ may be bonded together to form a ring with the nitrogen atom to which $Ar^4$ and $Ar^5$ are bonded;

$X^1$ represents a straight-chain, branched or cyclic alkyl group having 1 to 18 carbon atoms, a substituted or unsubstituted aryl group having 6 to 50 carbon atoms, or a substituted or unsubstituted heteroaryl group having 4 to 50 carbon atoms;

$X^2$ represents a substituted or unsubstituted arylene group having 6 to 50 carbon atoms; and $R^1$ through $R^7$ independently represent a hydrogen atom, a halogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms, provided that at least three of $R^1$ through $R^4$ are hydrogen atoms and at least two of $R^5$ through $R^7$ are hydrogen atoms; and

[iii]. in the case when m is 0 and n is 0, $X^1$ represents a straight-chain, branched or cyclic alkyl group having 1 to 18 carbon atoms, a substituted or unsubstituted aryl group having 6 to 50 carbon atoms, or a substituted or unsubstituted heteroaryl group having 4 to 50 carbon atoms;

$Ar^3$ and $X^2$ represents a substituted or unsubstituted aryl group having 6 to 50 carbon atoms, or a substituted or unsubstituted heteroaryl group having 4 to 50 carbon atoms, provided that the case when both of $Ar^3$ and $X^2$ independently represents an unsubstituted phenyl group, a phenyl group substituted by an alkyl group or by an alkoxy group, or a substituted or unsubstituted carbazolyl group is excluded.

$R^2$ represents a hydrogen atom, a halogen atom, a straight-chain, branched or cyclic alkyl group having 1 to 18 carbon atoms or a straight-chain, branched or cyclic alkoxy group having 1 to 18 carbon atoms; and $R^1$ and $R^3$ through $R^7$ independently represent a hydrogen atom, a halogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms.

Effect of the Invention

The carbazole compound of the formula (1) according to the present invention exhibits enhanced hole transport characteristics and high glass transition temperature, as compared with those of the conventional materials, and therefore, an organic EL device having a hole transport layer comprising the carbazole compound of the formula (1)

exhibits a low drive voltage, and has high luminous efficiency and enhanced durability.

BEST MODE FOR CARRYING OUT THE INVENTION

The invention will now be described in detail.

In the carbazole compound of formula (1), m represents an integer of 0 or 1, and n represents an integer of 0 to 3, provided that when m is 1, n is 0.

Details of the formula (1) will be described successively at every combination of m and n.

[i] In the case of m=1 and n=0:

$Ar^1$, $Ar^2$, $Ar^3$ and $X^2$ independently represent a substituted or unsubstituted aryl group having 6 to 50 carbon atoms or a substituted or unsubstituted heteroaryl group having 4 to 50 carbon atoms.

The substituted or unsubstituted aryl group having 6 to 50 carbon atoms for $Ar^1$, $Ar^2$, $Ar^3$ and $X^2$ includes, for example, substituted or unsubstituted phenyl, biphenylyl, terphenylyl, naphthyl, phenanthryl, anthryl, fluorenyl, benzofluorenyl, dibenzofluorenyl, fluoranthenyl, perylenyl, pyrenyl, picenyl and chrysenyl groups. As specific examples of the substituted or unsubstituted aryl group having 6 to 50 carbon atoms, there can be mentioned phenyl group, 4-methylphenyl group, 3-methylphenyl group, 2-methylphenyl group, 4-ethylphenyl group, 3-ethylphenyl group, 2-ethylphenyl group, 4-n-propylphenyl group, 4-isopropylphenyl group, 2-isopropylphenyl group, 4-n-butylphenyl group, 4-isobutylphenyl group, 4-sec-butylphenyl group, 4-tert-butylphenyl group, 4-n-pentylphenyl group, 4-isopentylphenyl group, 4-neopentylphenyl group, 4-n-hexylphenyl group, 4-n-octylphenyl group, 4-n-decylphenyl group, 4-n-dodecylphenyl group, 4-cyclopentylphenyl group, 4-cyclohexylphenyl group, 4-tritylphenyl group, 3-tritylphenyl group, 4-triphenylsilylphenyl group, 3-triphenylsilylphenyl group, 2,4-dimethylphenyl group, 2,5-dimethylphenyl group, 3,4-dimethylphenyl group, 3,5-dimethylphenyl group, 2,6-dimethylphenyl group, 2,3,5-trimethylphenyl group, 2,3,6-trimethylphenyl group, 3,4,5-trimethylphenyl group, 4-methoxyphenyl group, 3-methoxyphenyl group, 2-methoxyphenyl group, 4-ethoxyphenyl group, 3-ethoxyphenyl group, 2-ethoxyphenyl group, 4-n-propoxyphenyl group, 3-n-propoxyphenyl group, 4-isopropoxyphenyl group, 2-isopropoxyphenyl group, 4-n-butoxyphenyl group, 4-isobutoxyphenyl group, 4-sec-butoxyphenyl group, 4-n-pentyloxyphenyl group, 4-isopentyloxyphenyl group, 2-isopentyloxyphenyl group, 4-neopentyloxyphenyl group, 2-neopentyloxyphenyl group, 4-n-hexyloxyphenyl group, 2-(2-ethylbutyl)oxyphenyl group, 4-n-octyloxyphenyl group, 4-n-decyloxyphenyl group, 4-n-dodecyloxyphenyl group, 4-n-tetradecyloxyphenyl group, 4-cyclohexyloxyphenyl group, 2-cyclohexyloxyphenyl group, 4-phenoxyphenyl group, 2-methyl-4-methoxyphenyl group, 2-methyl-5-methoxyphenyl group, 3-methyl-4-methoxyphenyl group, 3-methyl-5-methoxyphenyl group, 3-ethyl-5-methoxyphenyl group, 2-methoxy-4-methylphenyl group, 3-methoxy-4-methylphenyl group, 2,4-dimethoxyphenyl group, 2,5-dimethoxyphenyl group, 2,6-dimethoxyphenyl group, 3,4-dimethoxyphenyl group, 3,5-dimethoxyphenyl group, 3,5-diethoxyphenyl group, 3,5-di-n-butoxyphenyl group, 2-methoxy-4-ethoxyphenyl group, 2-methoxy-6-ethoxyphenyl group, 3,4,5-trimethoxyphenyl group, 4-fluorophenyl group, 3-fluorophenyl group, 2-fluorophenyl group, 2,3-difluorophenyl group, 2,4-difluorophenyl group, 2,5-difluorophenyl group, 2,6-difluorophenyl group, 3,4-difluorophenyl group, 3,5-difluorophenyl group, 4-(1-naphthyl)phenyl group, 4-(2-naphthyl)phenyl group, 3-(1-naphthyl)phenyl group, 3-(2-naphthyl)phenyl group, 1-naphthyl group, 2-naphthyl group, 4-methyl-1-naphthyl group, 6-methyl-2-naphthyl group, 4-phenyl-1-naphthyl group, 6-phenyl-2-naphthyl group, 2-anthryl group, 9-anthryl group, 10-phenyl-9-anthryl group, 2-fluorenyl group, 9,9-dimethyl-2-fluorenyl group, 9,9-diethyl-2-fluorenyl group, 9,9-di-n-propyl-2-fluorenyl group, 9,9-di-n-octyl-2-fluorenyl group, 9,9-diphenyl-2-fluorenyl group, 9,9'-spirobifluorenyl group, 9-phenanthryl group, 2-phenanthryl group, benzofluorenyl group, dienzofluorenyl group, fluoranthenyl group, pyrenyl group, chrysenyl group, perylenyl group, picenyl group, 4-biphenylyl group, 3-biphenylyl group, 2-biphenylyl group, p-terphenylyl group, m-terphenylyl group and o-terphenylyl group.

The substituted or unsubstituted aryl group having 6 to 50 carbon atoms is not limited to these groups.

The substituted or unsubstituted heteroaryl group having 4 to 50 carbon atoms for $Ar^1$, $Ar^2$, $Ar^3$ and $X^2$ includes, for example, substituted or unsubstituted heteroaryl groups having at least one hetero atom selected from an oxygen atom, a nitrogen atom and a sulfur atom. As specific examples of the substituted or unsubstituted heteroaryl group having 4 to 50 carbon atoms, there can be mentioned 4-qunolyl group, 4-pyridyl group, 3-pyridyl group, 2-pyridyl group, 3-furyl group, 2-furyl group, 3-thienyl group, 2-thienyl group, 2-oxazolyl group, 2-thiazolyl group, 2-benzoxazolyl group, 2-benzothiazolyl group, 2-carbazolyl group, benzothiophenyl group, benzoimidazolyl group and dibenzothiophenyl group. The substituted or unsubstituted heteroaryl group having 4 to 50 carbon atoms is not limited to these groups.

$Ar^1$ and $Ar^2$ may be bonded together to form a ring with the nitrogen atom to which $Ar^1$ and $Ar^2$ are bonded, and $Ar^3$ and $X^2$ may be bonded together to form a ring with the nitrogen atom to which $Ar^3$ and $X^2$ are bonded. The ring formed from $Ar^1$ and $Ar^2$ or from $Ar^3$ and $X^2$ includes a carbazole ring, a phenoxazine ring and a phenothiazine ring, but it is not limited thereto.

In the case [i] of m=1 and n=0, $X^1$ represents a substituted or unsubstituted arylene group having 6 to 50 carbon atoms.

The substituted or unsubstituted arylene group having 6 to 50 carbon atoms includes, for example, a substituted or unsubstituted phenylene group, a substituted or unsubstituted biphenylene group, a substituted or unsubstituted terphenylene group, a substituted or unsubstituted naphthylene group, a substituted or unsubstituted fluorenylene group, a substituted or unsubstituted pyrenediyl group, a substituted or unsubstituted anthracenediyl and a substituted or unsubstituted phenanthrenediyl group. The substituted or unsubstituted arylene group having 6 to 50 carbon atoms is not limited to these groups. As specific examples of the substituents which the arylene group may have, those which are recited above as specific examples of the substituents of the aryl group for $Ar^1$, $Ar^2$, $Ar^3$ and $X^2$ can be mentioned.

In the case [i] of m=1 and n=0, $R^1$, $R^2$, $R^4$, $R^5$ and $R^7$ independently represent a hydrogen atom, a halogen atom, a substituted or unsubstituted amino group, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms.

The halogen atom for $R^1$, $R^2$, $R^4$, $R^5$ and $R^7$ includes fluorine, chlorine, bromine and iodine atoms.

The substituted or unsubstituted amino group for $R^1$, $R^2$, $R^4$, $R^5$ and $R^7$ includes, for example, dimethylamino group, diethylamino group, dipropylamino group, dibutylamino group, diphenylamino group, di(m-tolyl)amino group, di(p-tolyl)amino group, N-(m-tolyl)phenylamino group, N-(p-tolyl)phenylamino group, N-(1-naphthyl)phenylamino group, N-(2-naphthyl)phenylamino group, N-(4-biphenyl)phenylamino group, di(4-biphenyl)phenylamino group and di(2-naphthyl)amino group. The substituted or unsubstituted amino group is not limited to these groups.

As specific examples of the straight-chain, branched or cyclic alkyl group having 1 to 18 carbon atoms for $R^1$, $R^2$, $R^4$, $R^5$ and $R^7$, there can be mentioned methyl group, ethyl group, propyl group, isopropyl group, butyl group, sec-butyl group, tert-butyl group, pentyl group, hexyl group, heptyl group, octyl group, stearyl group, trichloromethyl group, trifluoromethyl group, cyclopropyl group and cyclohexyl group. The straight-chain, branched or cyclic alkyl group having 1 to 18 carbon atoms is not limited to these groups.

As specific examples of the straight-chain, branched or cyclic alkoxy group having 1 to 18 carbon atoms for $R^1$, $R^2$, $R^4$, $R^5$ and $R^7$, there can be mentioned methoxy group, ethoxy group, propoxy group, isopropoxy group, n-butoxy group, sec-butoxy group, tert-butoxy group, pentyloxy group, hexyloxy group and stearyloxy group. The straight-chain, branched or cyclic alkoxy group having 1 to 18 carbon atoms is not limited to these groups.

As specific examples of the substituted or unsubstituted aryl group having 6 to 50 carbon atoms and the substituted or unsubstituted heteroaryl group having 4 to 50 carbon atoms for $R^1$, $R^2$, $R^4$, $R^5$ and $R^7$, those which are recited above for $Ar^1$, $Ar^2$, $Ar^3$ and $X^2$ can be mentioned.

In the case [i] of m=1 and n=0, $R^3$ and $R^6$ independently represent a hydrogen atom, a halogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms. As specific examples of these alkyl, alkoxy, aryl and heteroaryl groups, those which are recited above can be mentioned. When at least one of $R^3$ and $R^6$ is a substituted aryl group having 6 to 50 carbon atoms or a substituted heteroaryl group having 4 to 50 carbon atoms, an amino group is excluded from the substituent which the aryl group and the heteroaryl group may have.

[ii] In the case of m=0 and n=1-3:

$Ar^3$, $Ar^4$ and $Ar^5$ independently represent a substituted or unsubstituted aryl group having 6 to 50 carbon atoms or a substituted or unsubstituted heteroaryl group having 4 to 50 carbon atoms. As specific examples of these aryl and heteroaryl groups, those which are recited above can be mentioned.

$Ar^4$ and $Ar^5$ may be bonded together to form a ring with the nitrogen atom to which $Ar^4$ and $Ar^5$ are bonded. As specific examples of the ring formed from $Ar^4$ and $Ar^5$, a carbazole ring, a phenoxazine ring and a phenothiazine ring are mentioned, but the ring is not limited thereto.

$X^1$ represents a straight-chain, branched or cyclic alkyl group having 1 to 18 carbon atoms, a substituted or unsubstituted aryl group having 6 to 50 carbon atoms, or a substituted or unsubstituted heteroaryl group having 4 to 50 carbon atoms. As specific examples of these alkyl, aryl and heteroaryl groups, those which are recited above can be mentioned.

$X^2$ represents a substituted or unsubstituted arylene group having 6 to 50 carbon atoms, and, as specific examples thereof, those which are recited above can be mentioned.

$R^1$ through $R^7$ independently represent a hydrogen atom, a halogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms. As specific examples of these halogen atom and alkyl, aryl and heteroaryl groups, those which are recited above can be mentioned. However, at least three of $R^1$ through $R^4$ are hydrogen atoms and at least two of $R^5$ through $R^7$ are hydrogen atoms.

[iii] In the case of m=0 and n=0:

$X^1$ represents a straight-chain, branched or cyclic alkyl group having 1 to 18 carbon atoms, a substituted or unsubstituted aryl group having 6 to 50 carbon atoms, or a substituted or unsubstituted heteroaryl group having 4 to 50 carbon atoms. As specific examples of these alkyl, aryl and heteroaryl groups, those which are recited above can be mentioned.

$Ar^3$ and $X^2$ represents a substituted or unsubstituted aryl group having 6 to 50 carbon atoms, or a substituted or unsubstituted heteroaryl group having 4 to 50 carbon atoms. As specific examples of these aryl and heteroaryl groups, those which are recited above can be mentioned. However, the case when both of $Ar^3$ and $X^2$ independently represent an unsubstituted phenyl group, a phenyl group substituted by an alkyl group or by an alkoxy group, or a substituted or unsubstituted carbazolyl group is excluded.

$R^2$ represents a hydrogen atom, a halogen atom, a straight-chain, branched or cyclic alkyl group having 1 to 18 carbon atoms or a straight-chain, branched or cyclic alkoxy group having 1 to 18 carbon atoms. As specific examples of these halogen, alkyl and alkoxy groups, those which are recited above can be mentioned.

$R^1$ and $R^3$ through $R^7$ independently represent a hydrogen atom, a halogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms. As specific examples of these halogen atom and alkyl, alkoxy, aryl and heteroaryl groups, those which are recited above can be mentioned.

In the case [i] of m=1 and n=0 in the formula (1), the carbazole compound is represented by the following general formula (2):

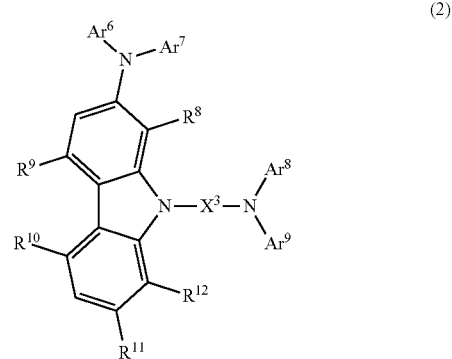

In the formula (2), $Ar^6$ through $Ar^9$ independently represent a substituted or unsubstituted aryl group having 6 to 50 carbon atoms or a substituted or unsubstituted heteroaryl group having 4 to 50 carbon atoms. $Ar^6$ and $Ar^7$ may be bonded together to form a ring with the nitrogen atom to which $Ar^6$ and $Ar^7$ are bonded, and, $Ar^8$ and $Ar^9$ may be bonded together to form a ring with the nitrogen atom to which $Ar^8$ and $Ar^9$ are bonded.

$R^8$ through $R^{12}$ independently represent a hydrogen atom, a halogen atom, a substituted or unsubstituted amino group, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms.

$X^3$ represents a substituted or unsubstituted arylene group having 6 to 50 carbon atoms.

As specific examples of the substituted or unsubstituted aryl group having 6 to 50 carbon atoms or the substituted or unsubstituted heteroaryl group having 4 to 50 carbon atoms, which are represented by $Ar^6$ through $Ar^9$, aryl groups and heteroaryl groups, which are recited above, can be mentioned.

As specific examples of the ring which may be formed from $Ar^6$ and $Ar^7$ together with the nitrogen atom to which $Ar^6$ and $Ar^7$ are bonded, and the ring which may be formed from $Ar^8$ and $Ar^9$ together with the nitrogen atom to which $Ar^8$ and $Ar^9$ are bonded, there can be mentioned a carbazole ring, a phenoxazine ring and a phenothiazine ring, but the rings are not limited thereto.

As mentioned above, $R^8$ through $R^{12}$ independently represent a hydrogen atom, a halogen atom, a substituted or unsubstituted amino group, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms. As specific examples of the halogen atom, the amino group, the alkyl group, the alkoxy group, the aryl group and the heteroaryl group, those which are recited above, can be mentioned.

As specific examples of the substituted or unsubstituted arylene group having 6 to 50 carbon atoms, represented by $X^3$, arylene groups as recited above can be mentioned. In view of excellent hole transport characteristics, the arylene group as $X^3$ is preferably at least one group selected from a substituted or unsubstituted phenylene group, a substituted or unsubstituted biphenylene group, a substituted or unsubstituted terphenylene group and a substituted or unsubstituted fluorenylene group.

Among the carbazole compounds of the formula (2), those which have a carbazole ring formed from $Ar^8$ and $Ar^9$ together with the nitrogen atom to which $Ar^8$ and $Ar^9$ are bonded, that is, carbazole compounds represented by the following general formula (3) are preferable because they have high glass transition temperature, and a high triplet level can be assured and the hole transport property is enhanced.

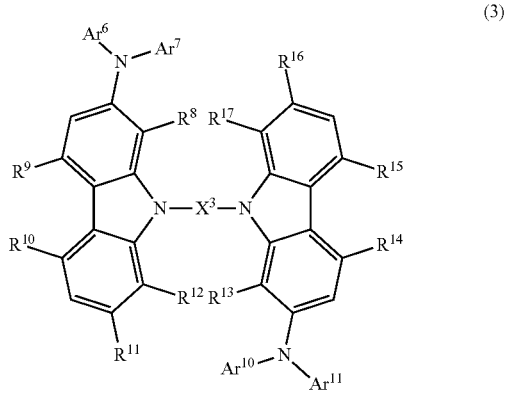

(3)

In the formula (3), $Ar^6$, $Ar^7$, $R^8$ through $R^{12}$ and $X^3$ are the same as defined above with regard to the formula (2); and, $Ar^{10}$ and $Ar^{11}$ independently represent a substituted or unsubstituted aryl group having 6 to 50 carbon atoms or a substituted or unsubstituted heteroaryl group having 4 to 50 carbon atoms.

$Ar^6$ and $Ar^7$ may be bonded together to form a ring with the nitrogen atom to which $Ar^6$ and $Ar^7$ are bonded, and $Ar^{10}$ and $Ar^{11}$ may be bonded together to form a ring with the nitrogen atom to which $Ar^{10}$ and $Ar^{11}$ are bonded.

$R^{13}$ through $R^{17}$ independently represent a hydrogen atom, a halogen atom, a substituted or unsubstituted amino group, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms.

In the carbazole compound of the formula (3), as specific examples of the substituted or unsubstituted aryl group having 6 to 50 carbon atoms and the substituted or unsubstituted heteroaryl group having 4 to 50 carbon atoms, represented by $Ar^{10}$ and $Ar^{11}$, those which are recited above can be mentioned.

As specific examples of the ring formed from $Ar^6$ and $Ar^7$, or from $Ar^{10}$ and $Ar^{11}$, a carbazole ring, a phenoxazine ring and a phenothiazine ring are mentioned, but the ring is not limited thereto.

In the carbazole compound of the formula (3), as specific examples of the halogen atom, the substituted or unsubstituted amino group, the straight-chain, branched or cyclic alkyl group having 1 to 18 carbon atoms, the straight-chain, branched or cyclic alkoxy group having 1 to 18 carbon atoms, the substituted or unsubstituted aryl group having 6 to 50 carbon atoms, and the substituted or unsubstituted heteroaryl group having 4 to 50 carbon atoms, represented by $R^{13}$ through $R^{17}$, those which are recited above can be mentioned.

In the case [iii] of m=0 and n=1-3 in the formula (1), the carbazole compound is represented by the following general formula (4):

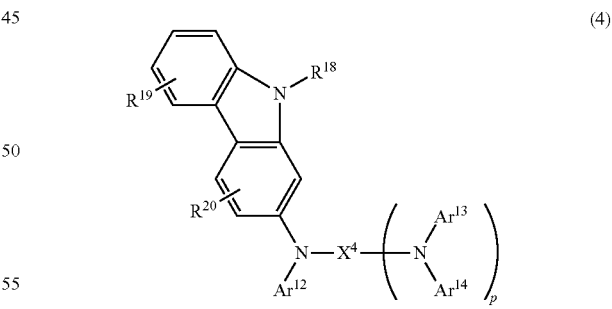

(4)

In the formula (4), $Ar^{12}$, $Ar^{13}$ and $Ar^{14}$ independently represent a substituted or unsubstituted aryl group having 6 to 50 carbon atoms, or a substituted or unsubstituted heteroaryl group having 4 to 50 carbon atoms, provided that $Ar^{13}$ and $Ar^{14}$ may be bonded together to form a ring with the nitrogen atom to which $Ar^{13}$ and $Ar^{14}$ are bonded;

$R^{18}$ represents a straight-chain, branched or cyclic alkyl group having 1 to 18 carbon atoms, a substituted or unsubstituted aryl group having 6 to 50 carbon atoms, or a substituted or unsubstituted heteroaryl group having 4 to 50 carbon atoms, provided that an amino-substituted aryl group is excluded from the substituted aryl group;

each of the four groups of $R^{19}$ and each of the three groups of $R^{20}$ independently represent a hydrogen atom, a halogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms; and $X^4$ represents a substituted or unsubstituted arylene group having 6 to 50 carbon atoms; and p is an integer of 1 to 3.

In the carbazole compound of the formula (4), as specific examples of the substituted or unsubstituted aryl group having 6 to 50 carbon atoms, and the substituted or unsubstituted heteroaryl group having 4 to 50 carbon atoms, represented by $Ar^{12}$, $Ar^{13}$ and $Ar^{14}$, those which are recited above can be mentioned.

As specific examples of the ring which may be formed from $Ar^{13}$ and $Ar^{14}$, together with the nitrogen atom to which $Ar^{13}$ and $Ar^{14}$ are bonded, a carbazole ring, a phenoxazine ring and a phenothiazine ring are mentioned, but the ring is not limited thereto.

In the carbazole compound of the formula (4), as specific examples of the straight-chain, branched or cyclic alkyl group having 1 to 18 carbon atoms, a substituted or unsubstituted aryl group having 6 to 50 carbon atoms, or a substituted or unsubstituted heteroaryl group having 4 to 50 carbon atoms, which are represented by $R^{18}$, those which are recited above can be mentioned. However, an amino-substituted aryl group is excluded from the substituted aryl group for $R^{18}$.

In the carbazole compound of the formula (4), as mentioned above, each of the four groups of $R^{19}$ and each of the three groups of $R^{20}$ independently represent a hydrogen atom, a halogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms. As specific examples of the halogen atom, the alkyl group, the alkoxy group, the aryl group and the heteroaryl group, those which are recited above, can be mentioned.

In the carbazole compound of the formula (4), as specific examples of the substituted or unsubstituted arylene group having 6 to 50 carbon atoms, which is represented by $X^4$, arylene groups as recited above can be mentioned. In view of excellent hole transport characteristics, the arylene group as $X^4$ is preferably at least one group selected from a substituted or unsubstituted phenylene group, a substituted or unsubstituted biphenylene group and a substituted or unsubstituted terphenylene group.

Preferable examples of the carbazole compound of the formula (4) include those which p is 1 and $X^4$ is an unsubstituted or substituted arylene group represented by any one of the following general formulas (5) through (9).

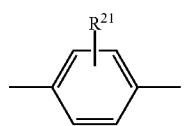
(5)

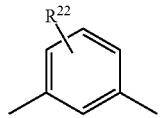
(6)

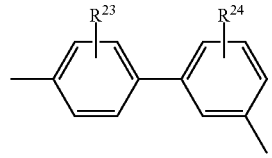
(7)

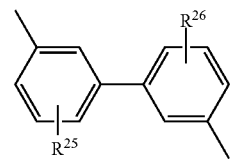
(8)

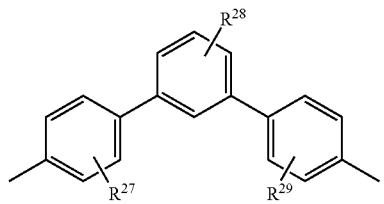
(9)

In the formulas (5) through (9), each arylene group of the formulas (5) through (9) has four groups represented by one of $R^{21}$ through $R^{29}$ in the benzene ring or each benzene ring. Each of the four groups independently represents a hydrogen atom, a halogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms.

In each arylene group of the formulae (5) through (9), each of the four groups represented by one of $R^{21}$ through $R^{29}$ in the benzene ring or each benzene ring independently represents a hydrogen atom, a halogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms; and, as specific examples of the halogen atom, the alkyl group, the alkoxy group, the aryl group and the heteroaryl group, those which are recited above can be mentioned.

In the carbazole compound of the formula (4), a preferable carbazole compound is such that $Ar^{13}$ and $Ar^{14}$ are bonded together to form a carbazole ring represented by the following general formula (10), together with the nitrogen atom to which $Ar^{13}$ and $Ar^{14}$ are bonded. Another preferable carbazole compound has a structure such that $Ar^{13}$ in the formula (4) is represented by the following general formula (11). The carbazole compound having the carbazole ring of the formula (10) or the carbazole ring of the formula (11) exhibits a high glass transition temperature and excellent hole transport property.

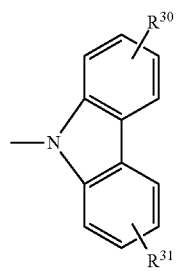

(10)

In the formula (10), the four groups each represented by $R^{30}$ or $R^{31}$ in each benzene ring independently represent a hydrogen atom, a halogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms.

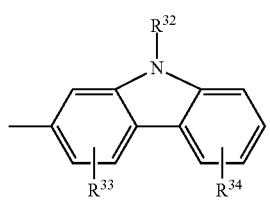

(11)

In the formula (11), $R^{32}$ represents a straight-chain, branched or cyclic alkyl group having 1 to 18 carbon atoms, a substituted or unsubstituted aryl group having 6 to 50 carbon atoms, or a substituted or unsubstituted heteroaryl group having 4 to 50 carbon atoms; and each of the three groups of $R^{33}$ and each of the four groups of $R^{34}$ in the respective benzene rings independently represent a hydrogen atom, a halogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms.

In the formula (10), as specific examples of the halogen atom, the straight-chain, branched or cyclic alkyl group having 1 to 18 carbon atoms, the straight-chain, branched or cyclic alkoxy group having 1 to 18 carbon atoms, the substituted or unsubstituted aryl group having 6 to 50 carbon atoms, or the substituted or unsubstituted heteroaryl group having 4 to 50 carbon atoms, which are represented by the four groups of $R^{30}$ or $R^{31}$, there can be mentioned those which are mentioned above.

In the formula (11), as specific examples of the straight-chain, branched or cyclic alkyl group having 1 to 18 carbon atoms, the substituted or unsubstituted aryl group having 6 to 50 carbon atoms, or the substituted or unsubstituted heteroaryl group having 4 to 50 carbon atoms, which are represented by $R^{32}$, there can be mentioned those which are mentioned above.

In the formula (11), as specific examples of the halogen atom, the straight-chain, branched or cyclic alkyl group having 1 to 18 carbon atoms, the straight-chain, branched or cyclic alkoxy group having 1 to 18 carbon atoms, the substituted or unsubstituted aryl group having 6 to 50 carbon atoms, or the substituted or unsubstituted heteroaryl group having 4 to 50 carbon atoms, which are represented by the three groups of $R^{33}$ and the four groups of $R^{34}$, there can be mentioned those which are mentioned above.

In the case [iii] of m=0 and n=0 in the formula (1), the carbazole compound is represented by the following general formula (12).

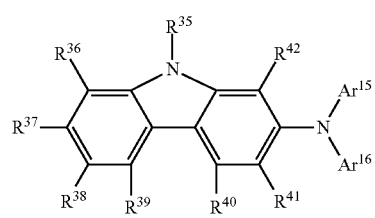

(12)

In the formula (12), $Ar^{15}$ and $Ar^{16}$ independently represent a substituted or unsubstituted aryl group having 6 to 50 carbon atoms, or a substituted or unsubstituted heteroaryl group having 4 to 50 carbon atoms, provided that the case when both of $Ar^{15}$ and $Ar^{16}$ independently represent an unsubstituted phenyl group, a phenyl group substituted by an alkyl group or by an alkoxy group, or a carbazolyl group is excluded;

$R^{35}$ represents a straight-chain, branched or cyclic alkyl group having 1 to 18 carbon atoms, a substituted or unsubstituted aryl group having 6 to 50 carbon atoms, or a substituted or unsubstituted heteroaryl group having 4 to 50 carbon atoms;

$R^{37}$ represents a hydrogen atom, a halogen atom, a straight-chain, branched or cyclic alkyl group having 1 to 18 carbon atoms, or a straight-chain, branched or cyclic alkoxy group having 1 to 18 carbon atoms; and $R^{36}$ and $R^{38}$ through $R^{42}$ independently represent a hydrogen atom, a halogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms.

In the carbazole compound of the formula (12), as mentioned above, $Ar^{15}$ and $Ar^{16}$ independently represent a substituted or unsubstituted aryl group having 6 to 50 carbon atoms, or a substituted or unsubstituted heteroaryl group having 4 to 50 carbon atoms.

As specific examples of the substituted or unsubstituted aryl group having 6 to 50 carbon atoms, those which are recited above can be mentioned. However, at least one of $Ar^{15}$ and $Ar^{16}$ is preferably a group other than an unsubstituted phenyl group, or other than a phenyl group substituted by an alkyl group or by an alkoxy group. This because the carbazole compound of the formula (12) wherein both of $Ar^{15}$ or $Ar^{16}$ are an unsubstituted phenyl group, or a phenyl group substituted by an alkyl group or by an alkoxy group, exhibits a low glass transition temperature.

As specific examples of the substituted or unsubstituted heteroaryl group having 4 to 50 carbon atoms, those which are recited above can be mentioned. However, a carbazolyl group is excluded from the substituted or unsubstituted heteroaryl group having 4 to 50 carbon atoms for $Ar^{15}$ and $Ar^{16}$.

In the carbazole compound of the formula (12), at least one of $Ar^{15}$ and $Ar^{16}$ preferably represents a substituted or unsubstituted 4-biphenylyl group, a substituted or unsubstituted 3-biphenylyl group, a substituted or unsubstituted m-terphenylyl group, or a substituted or unsubstituted 2-fluorenyl group. This is because the carbazole compounds having these groups as $Ar^{15}$ and $Ar^{16}$ exhibit a high glass transition temperature, and has a high triple level as compared with a green phosphorescent material.

In the carbazole compound of the formula (12), as mentioned above, $R^{35}$ represents a straight-chain, branched or cyclic alkyl group having 1 to 18 carbon atoms, a substituted or unsubstituted aryl group having 6 to 50 carbon atoms, or a substituted or unsubstituted heteroaryl group having 4 to 50 carbon atoms. As specific examples of these groups, those which are recited above can be mentioned.

Among the groups for $R^{35}$ in the formula (12), phenyl group, 4-biphenylyl group, 3-biphenylyl group, p-terphenylyl group, m-terphenylyl group, 1-naphthyl group, 2-naphthyl group, 9-phenathryl group and 2-fluorenyl group are preferable because of a high glass transition temperature.

In the carbazole compound of the formula (12), as mentioned above, $R^{37}$ represents a hydrogen atom, a halogen atom, a straight-chain, branched or cyclic alkyl group having 1 to 18 carbon atoms or a straight-chain, branched or cyclic alkoxy group having 1 to 18 carbon atoms. As specific examples of these groups, those which are recited above can be mentioned.

In the carbazole compound of the formula (12), as mentioned above, $R^{36}$ and $R^{38}$ through $R^{42}$ independently represent a hydrogen atom, a halogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms. As specific examples of these groups, those which are recited above can be mentioned.

Specific examples of the carbazole compound of the formula (1) according to the present invention are recited below, but are not limited thereto.

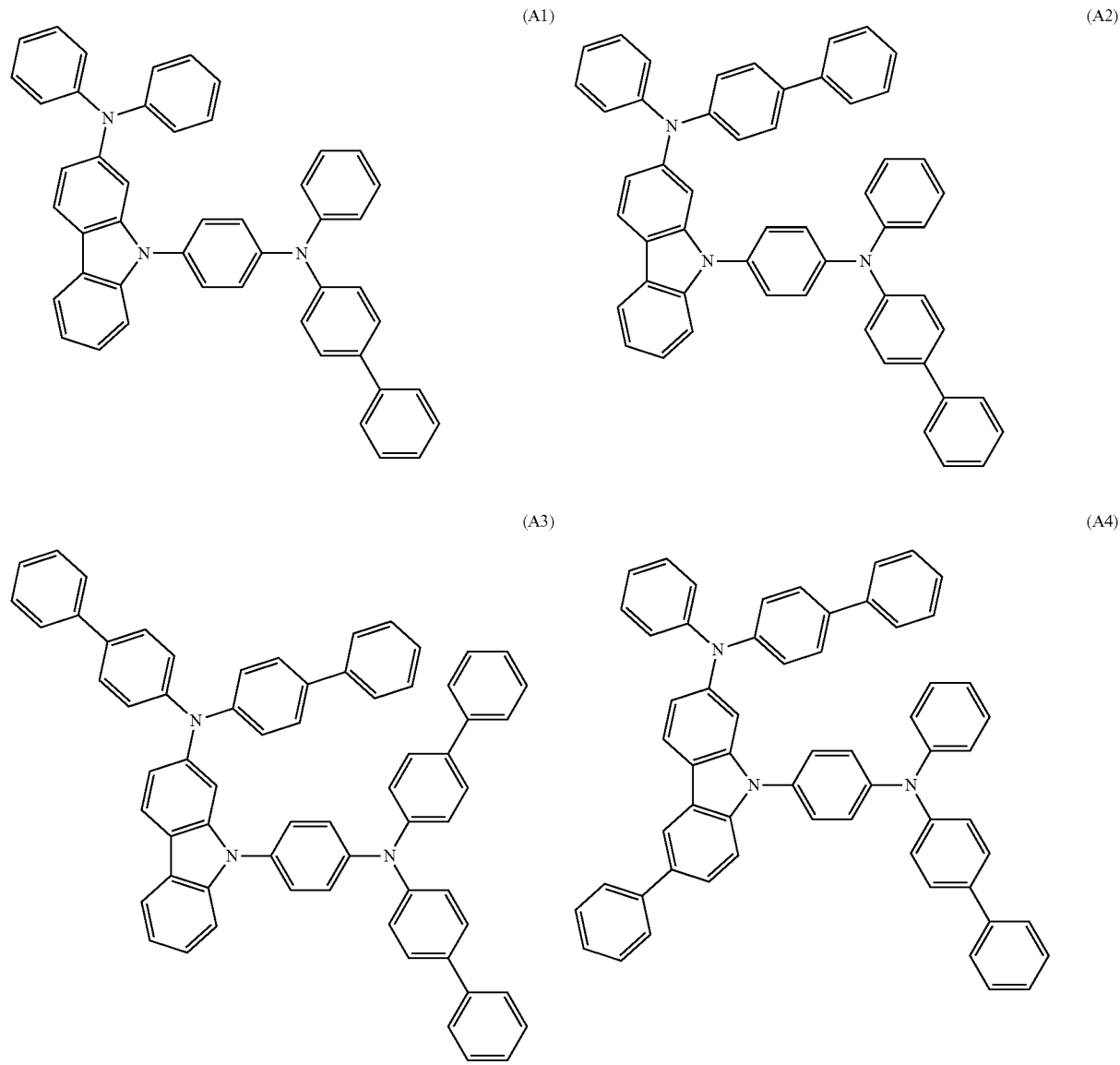

-continued
(A5)
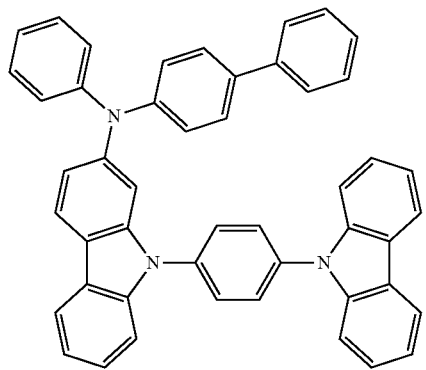
(A6)
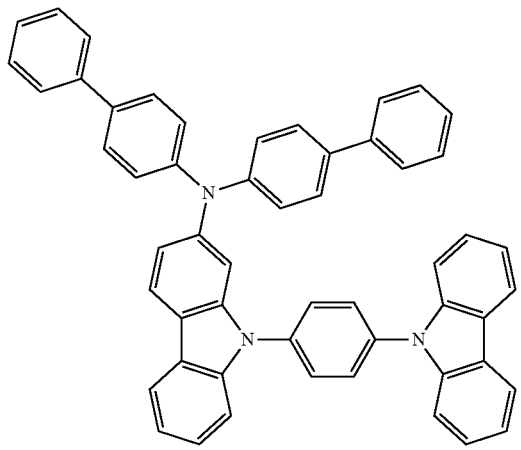
(A7)
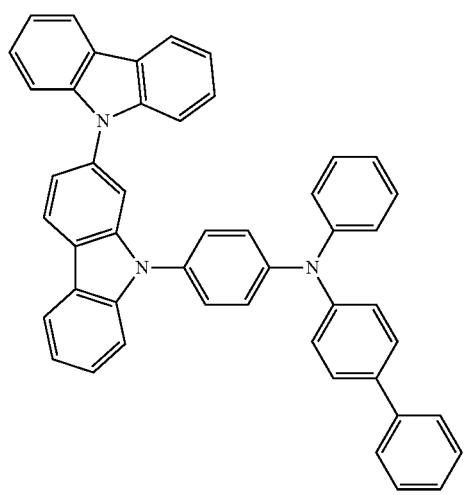
(A8)
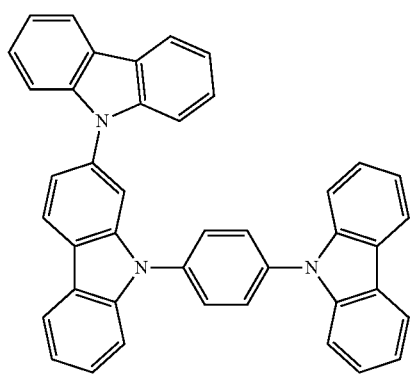
(A9)
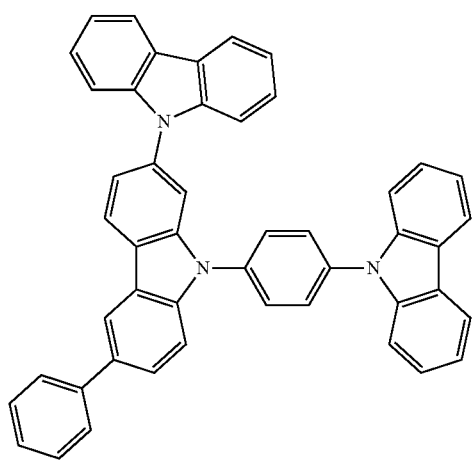
(A10)
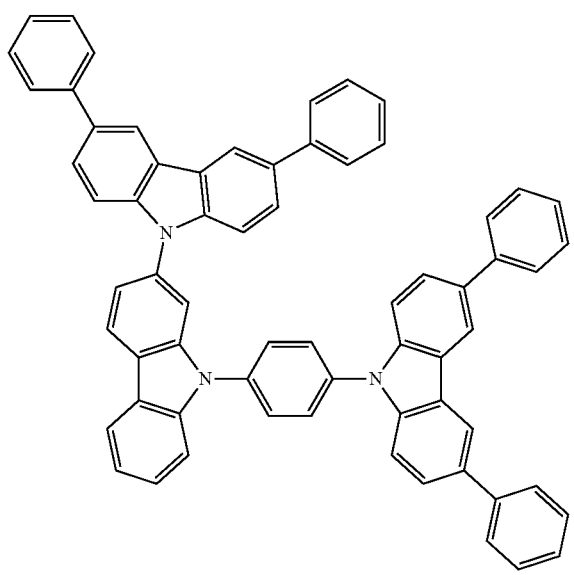

-continued
(A11)
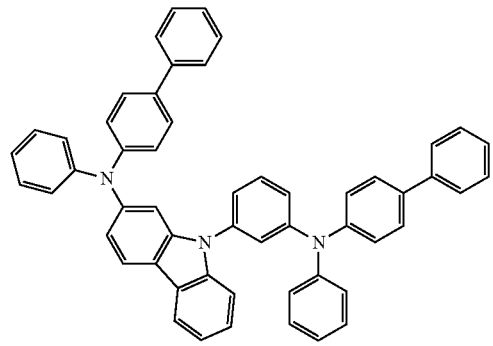
(A12)
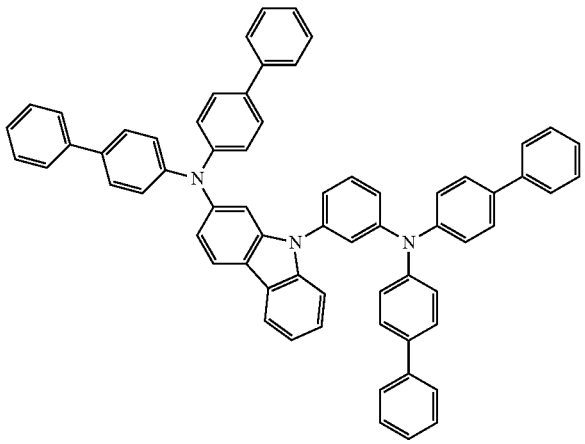
(A13)
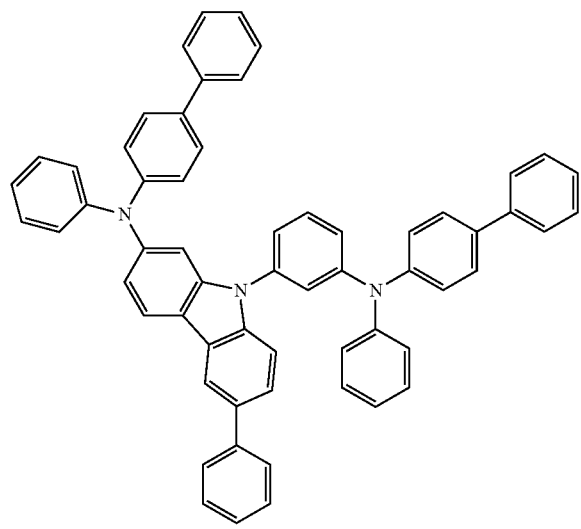
(A14)
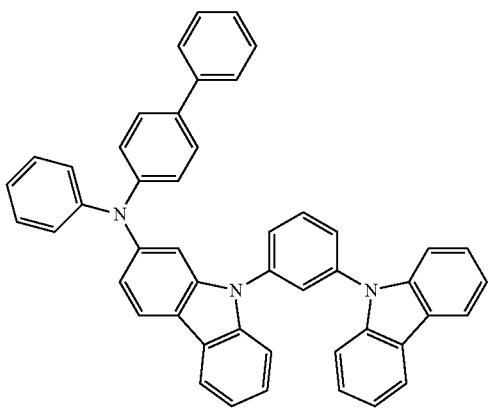
(A15)
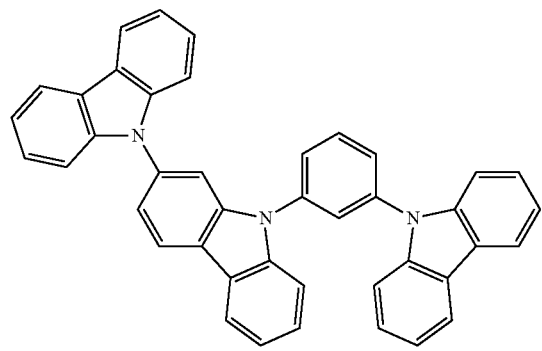

-continued
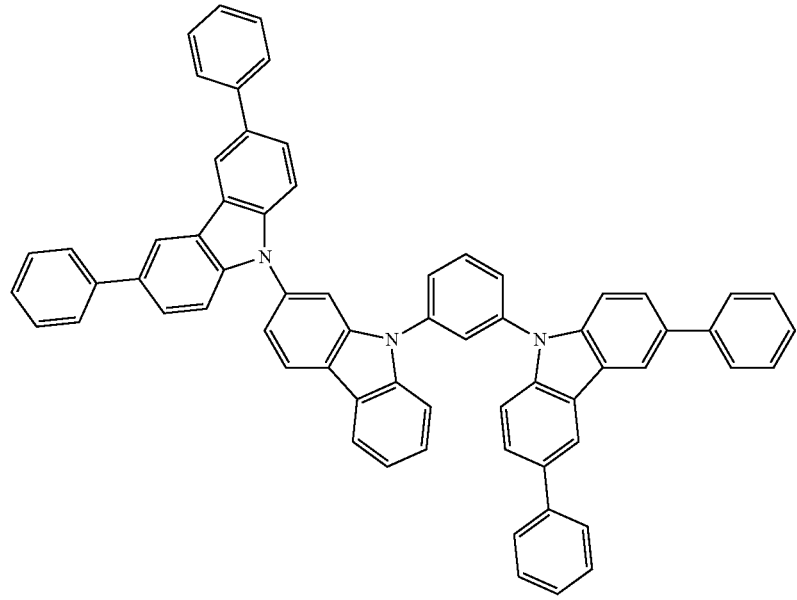
(A16)
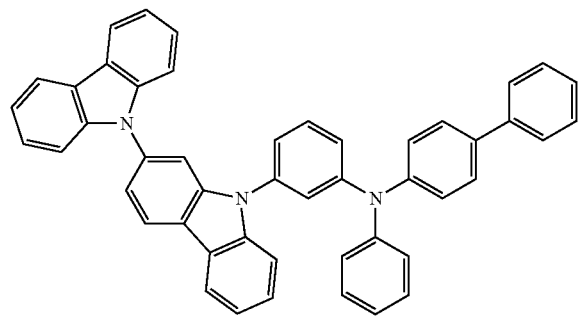
(A17)
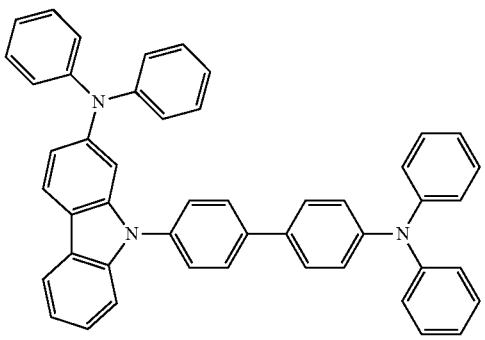
(A18)
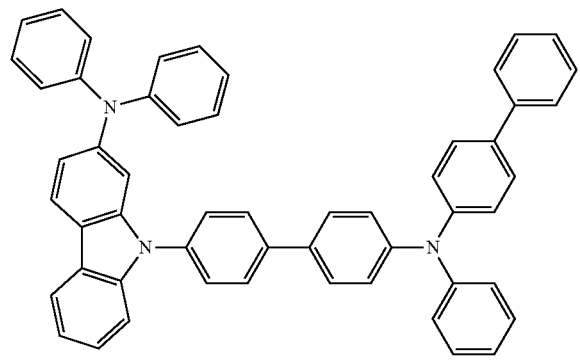
(A19)
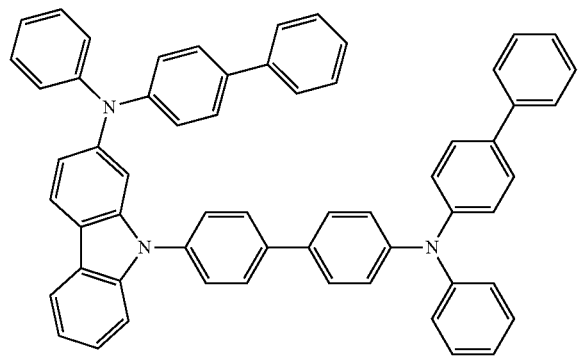
(A20)

-continued
(A21)
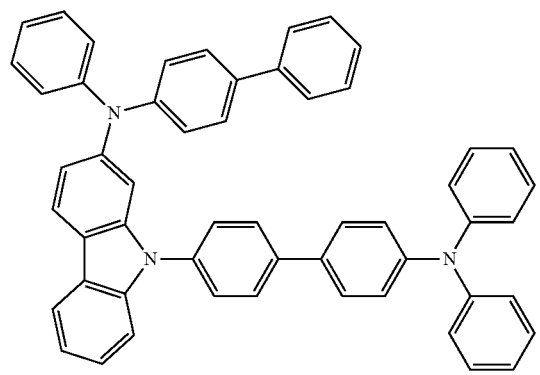
(A22)
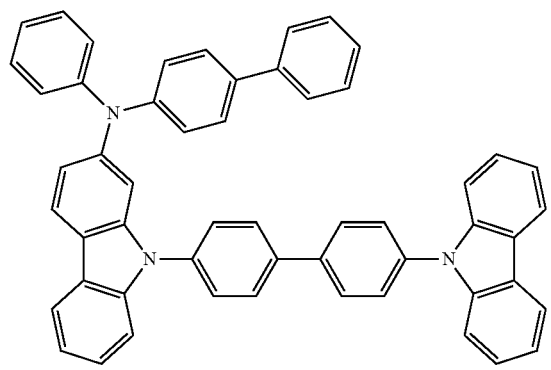
(A23)
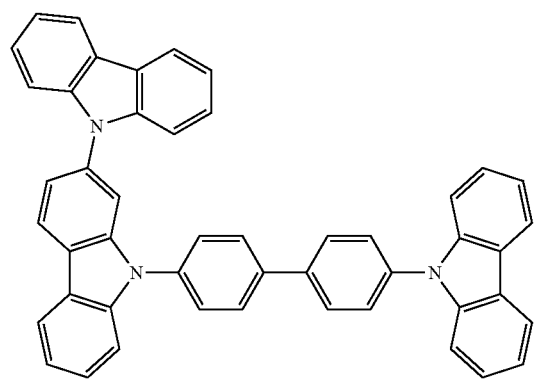
(A24)
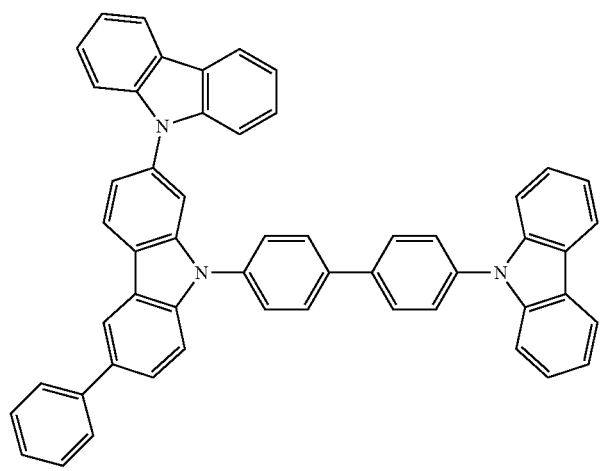
(A25)
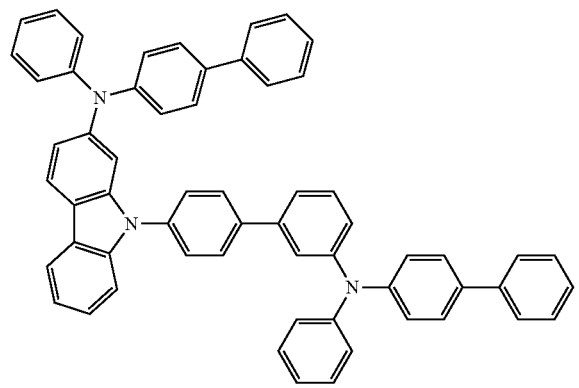
(A26)
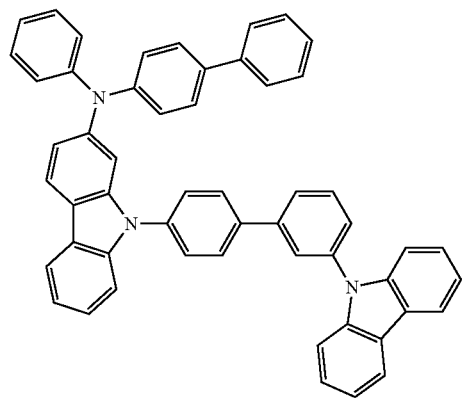
(B1)
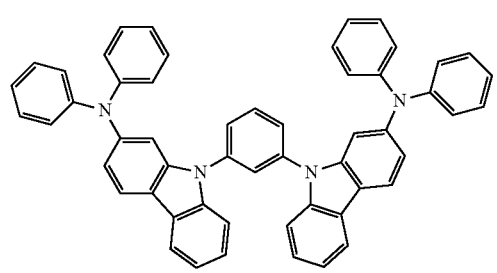
(B2)
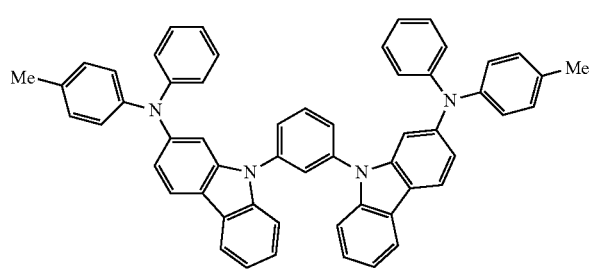

(B3)
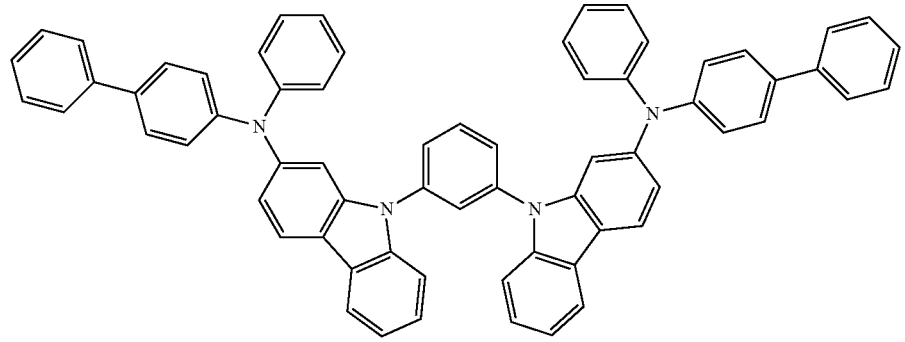
(B4)
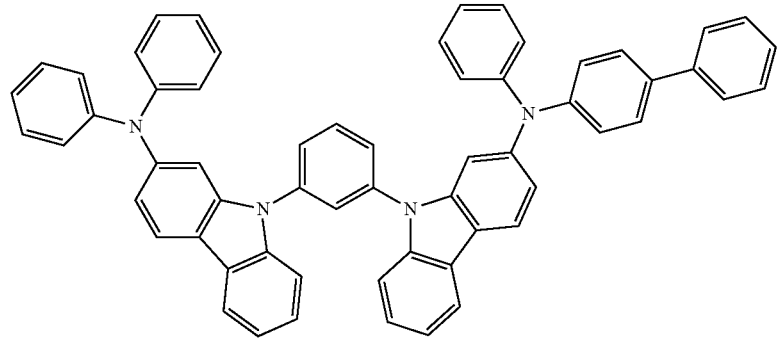
(B5)
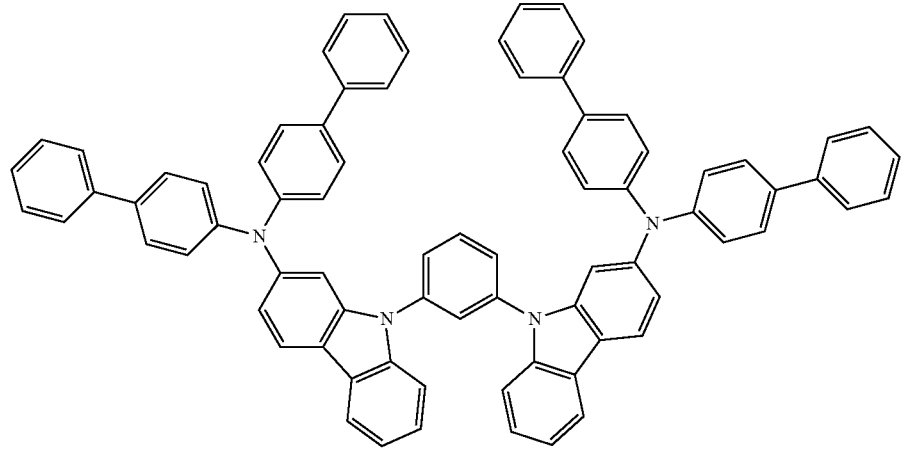
(B6) (B7)
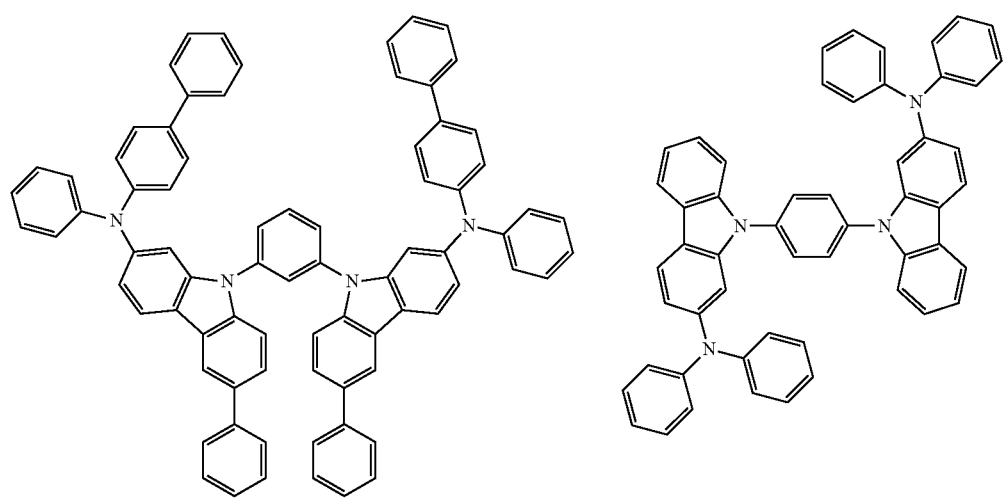

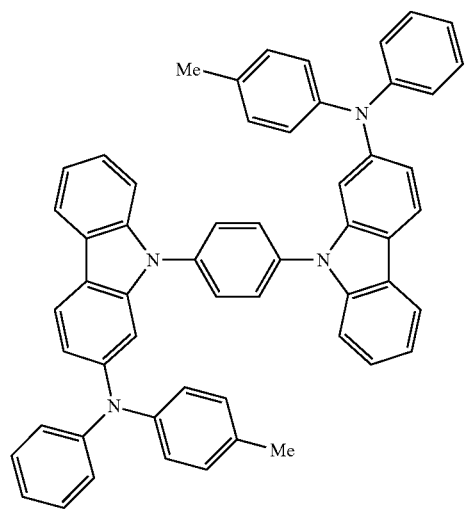
(B8)
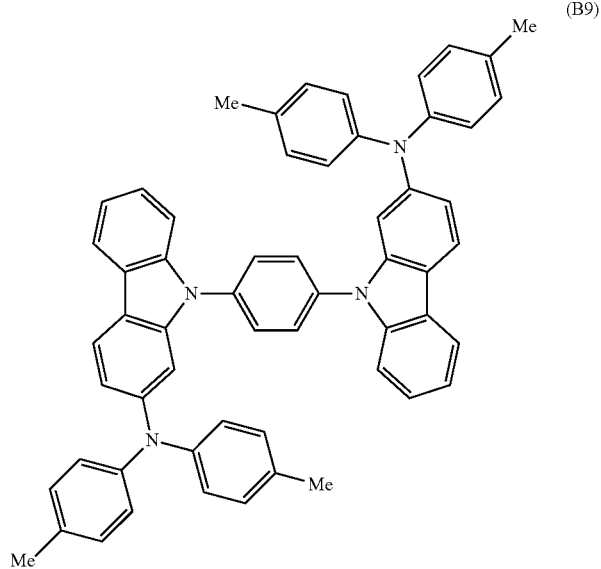
(B9)
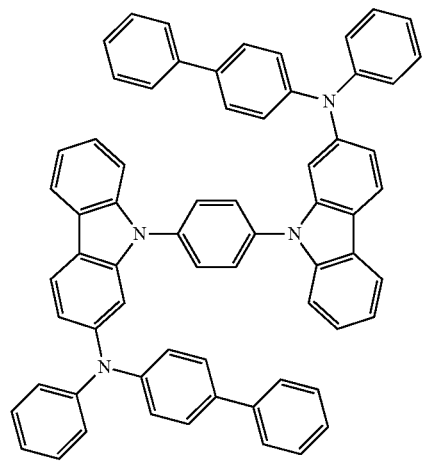
(B10)
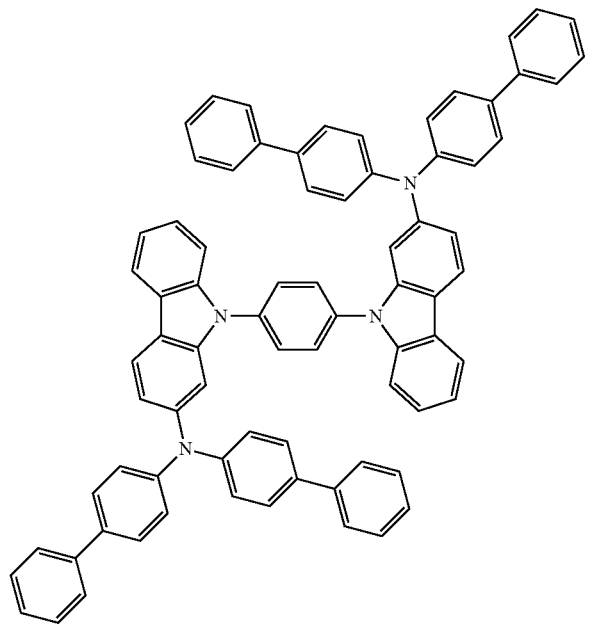
(B11)

-continued
(B12) 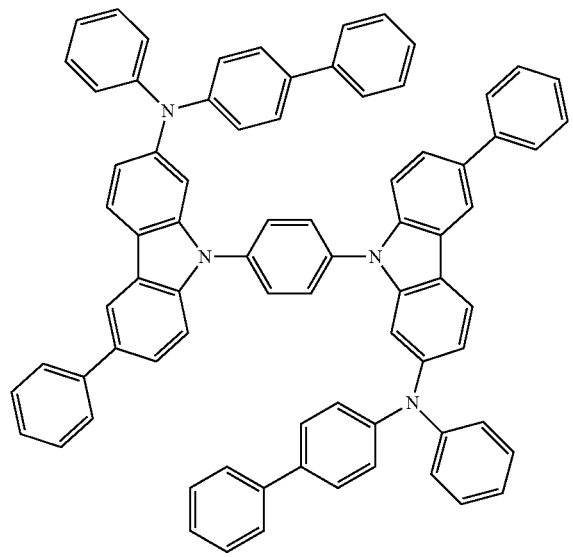
(B13) 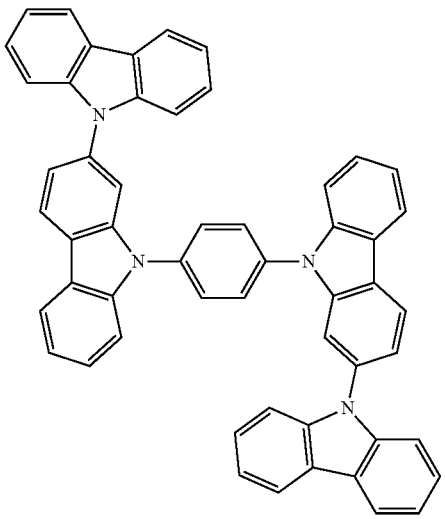
(B14) 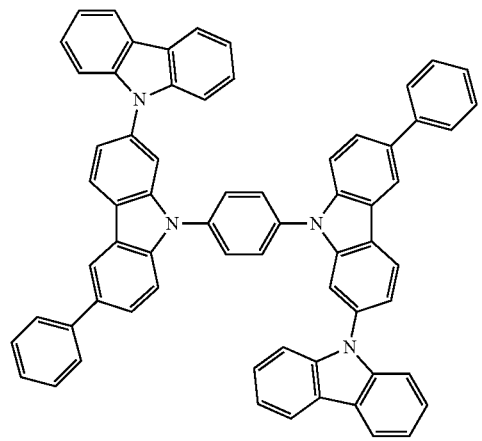
(B15) 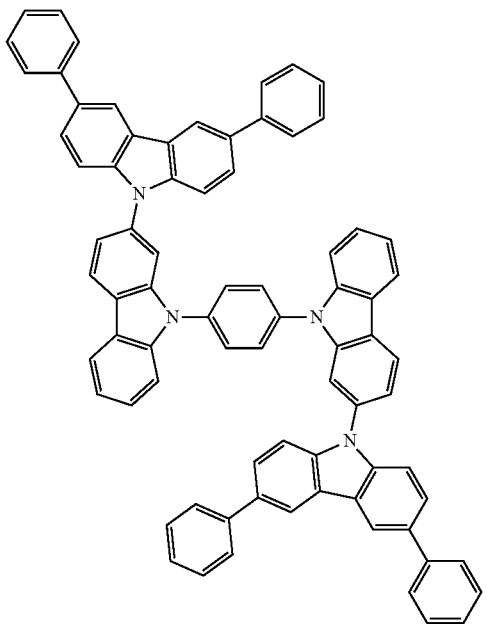
(B16) 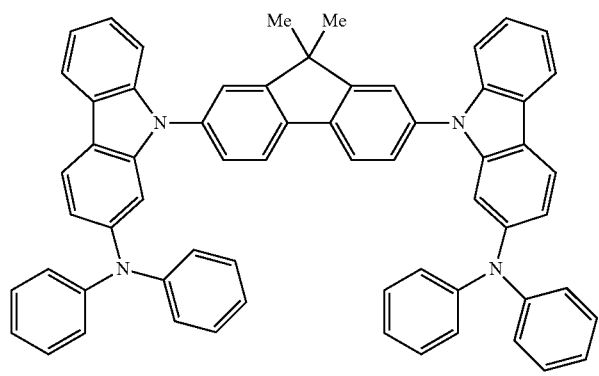

(B17)
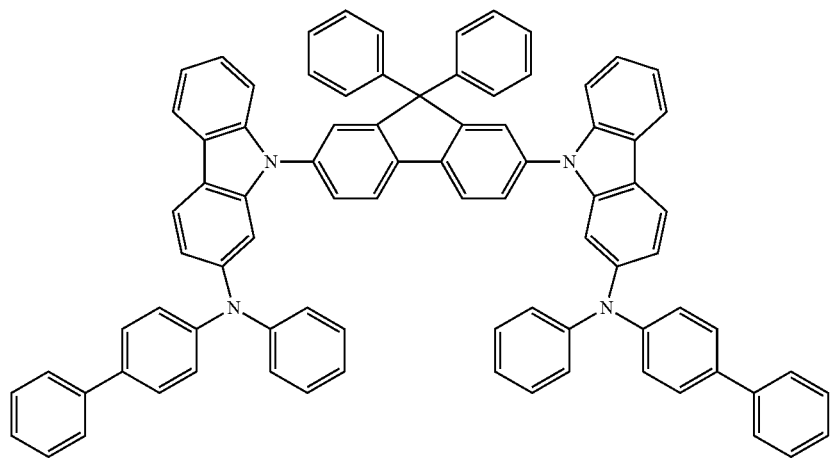
(B18)
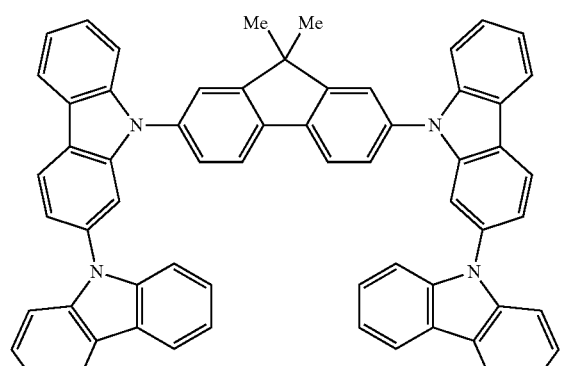
(B19)
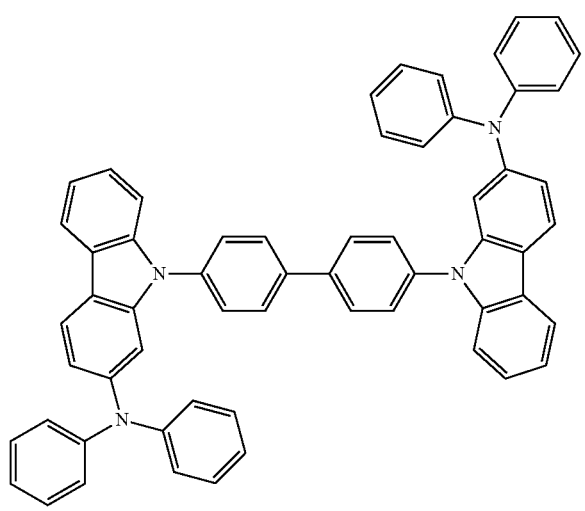
(B20)
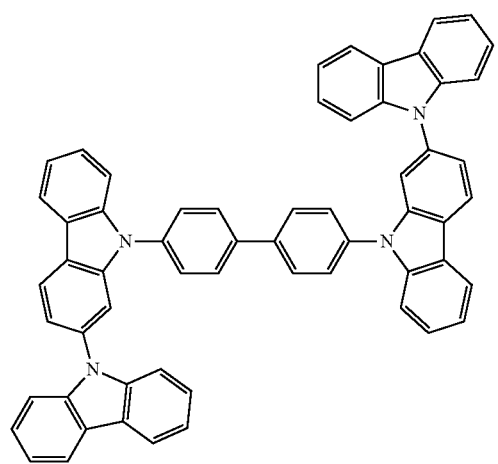
(B21)
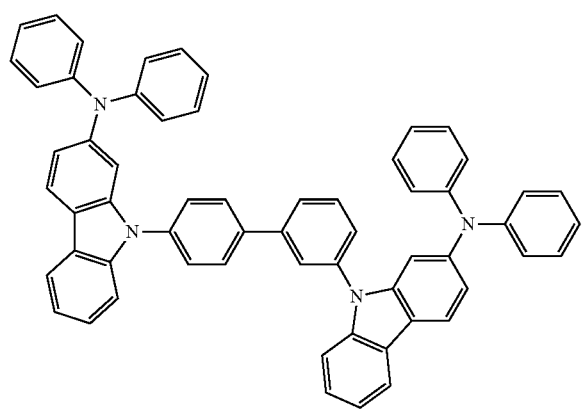

-continued
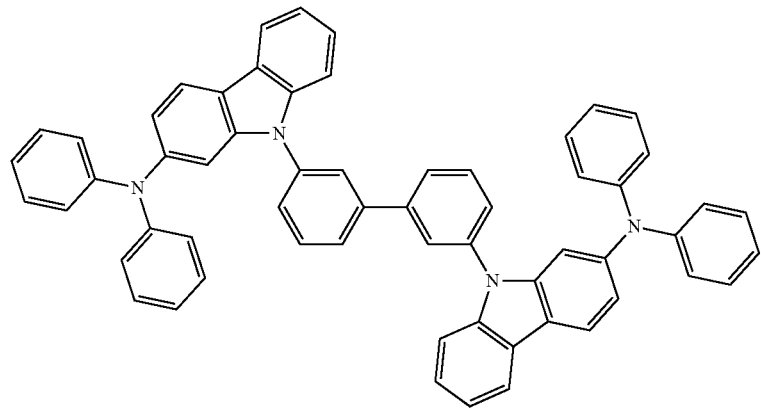
(B22)
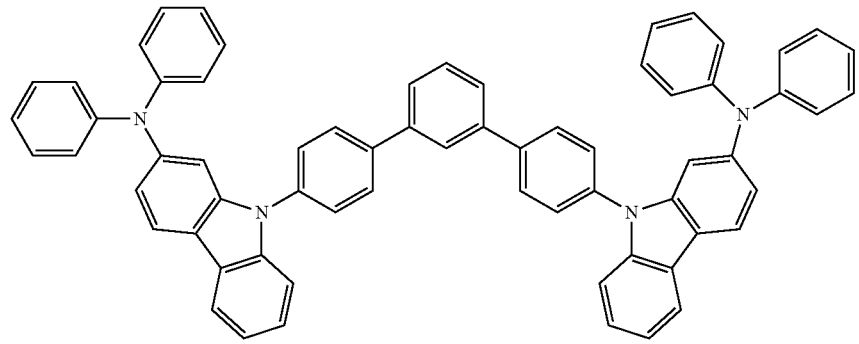
(B23)
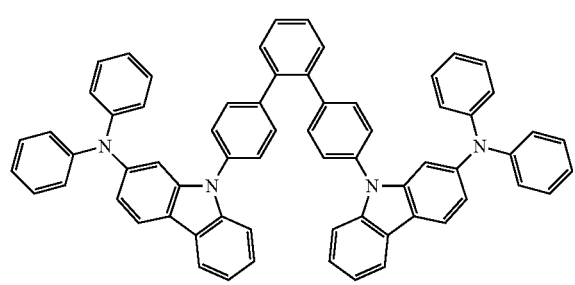
(B24)
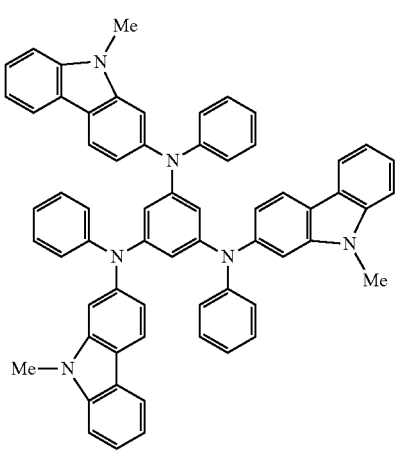
(C1)

(C2)
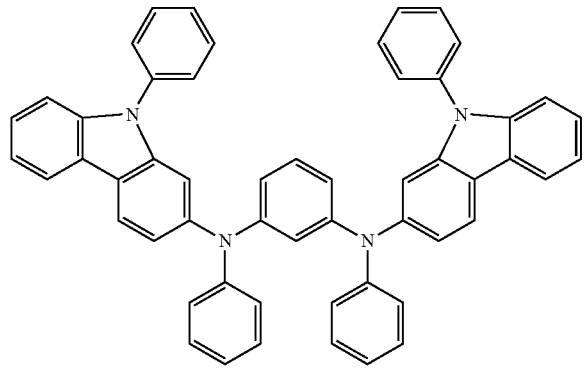
(C3)
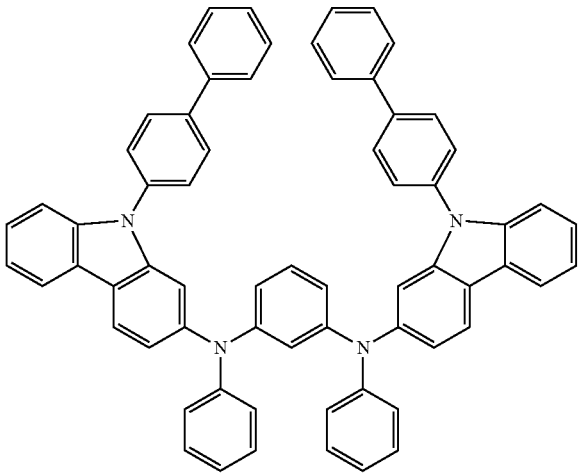
(C4)
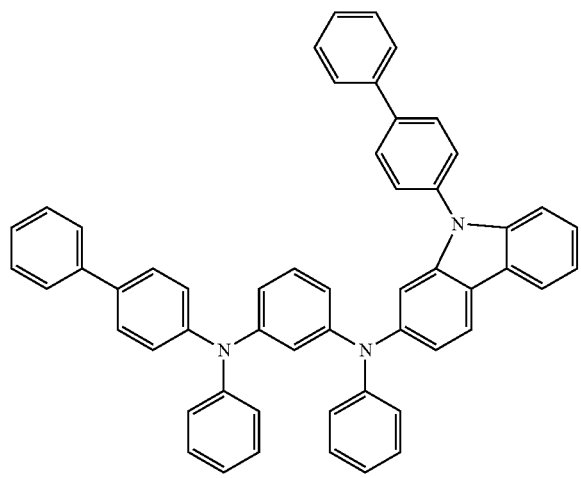
(C5)
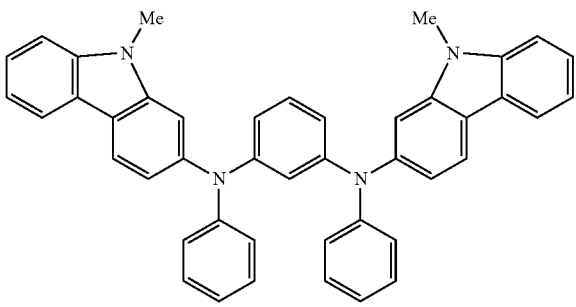
(C6)
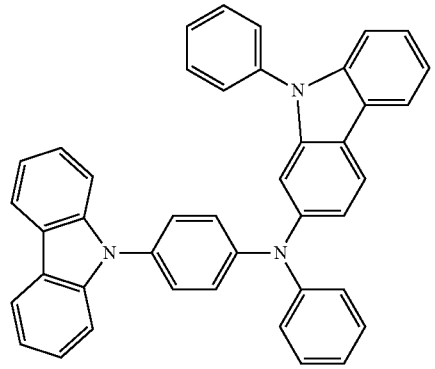
(C7)
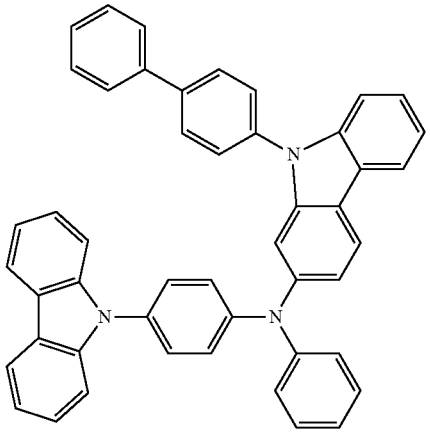

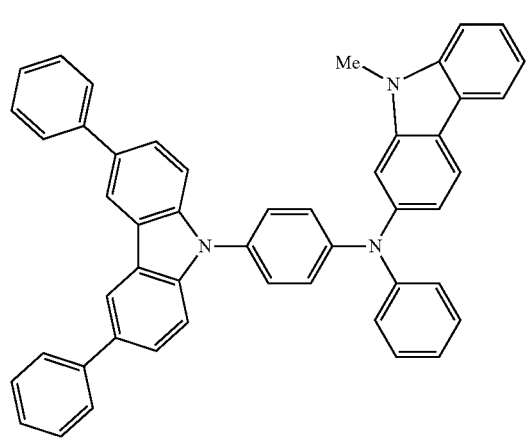
(C8)
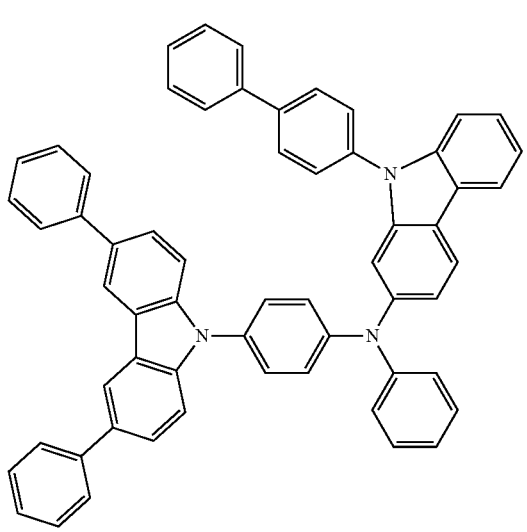
(C9)
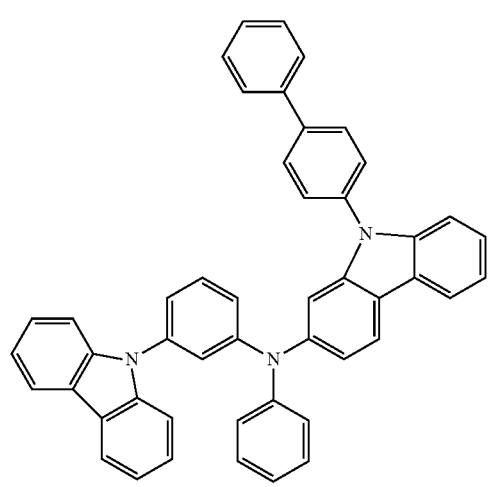
(C10)
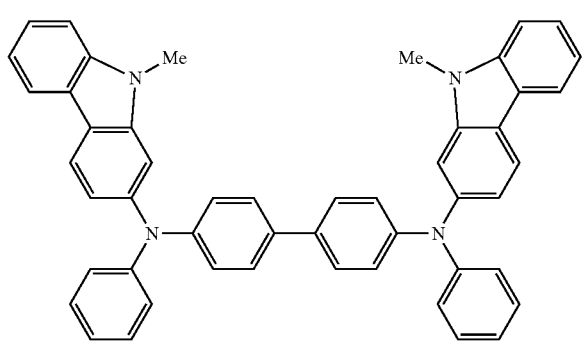
(D1)
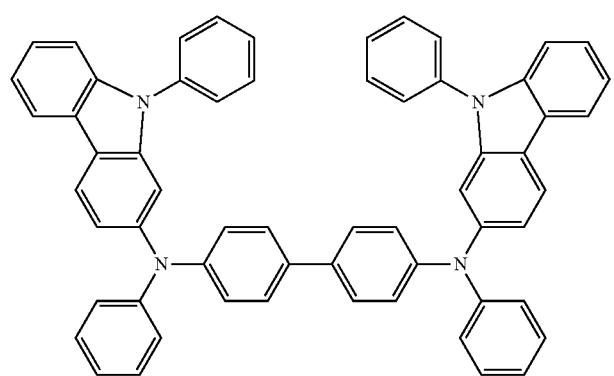
(D2)

-continued
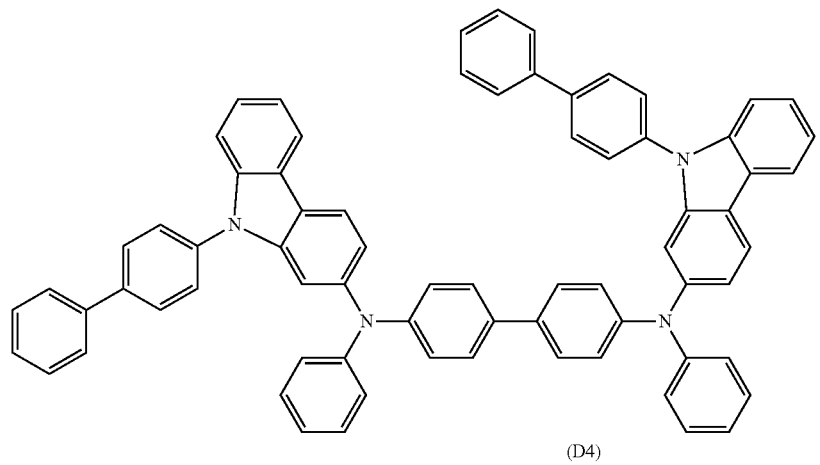
(D3)
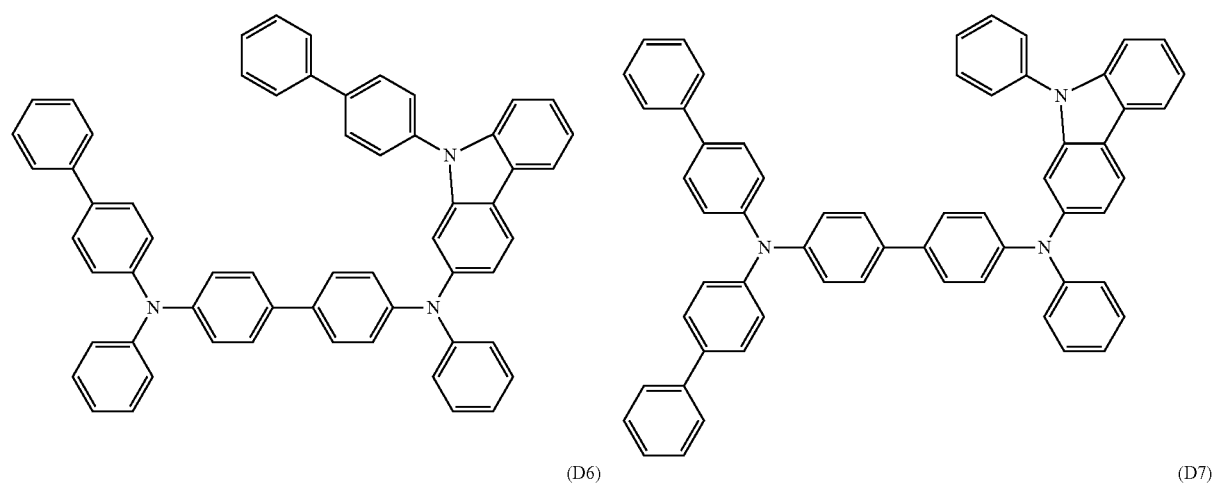
(D4)   (D5)
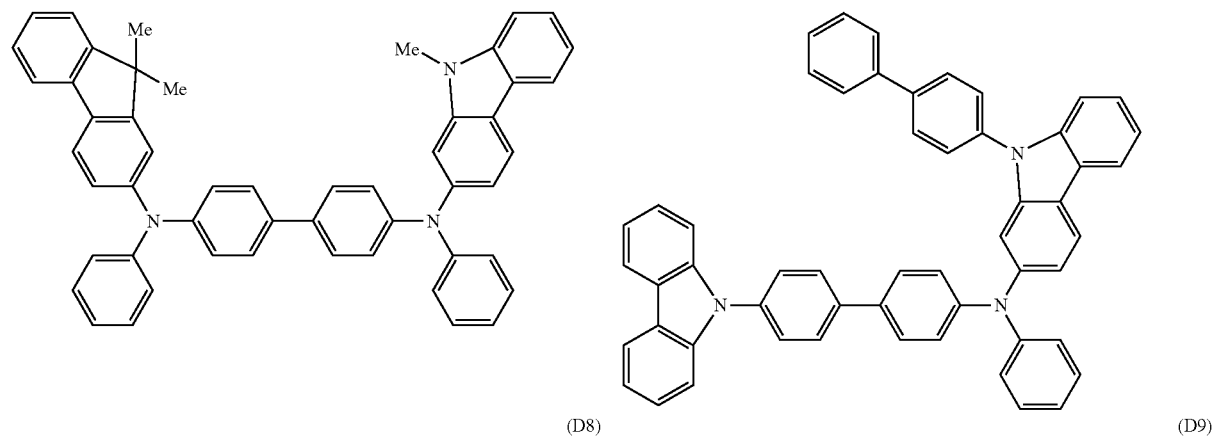
(D6)   (D7)
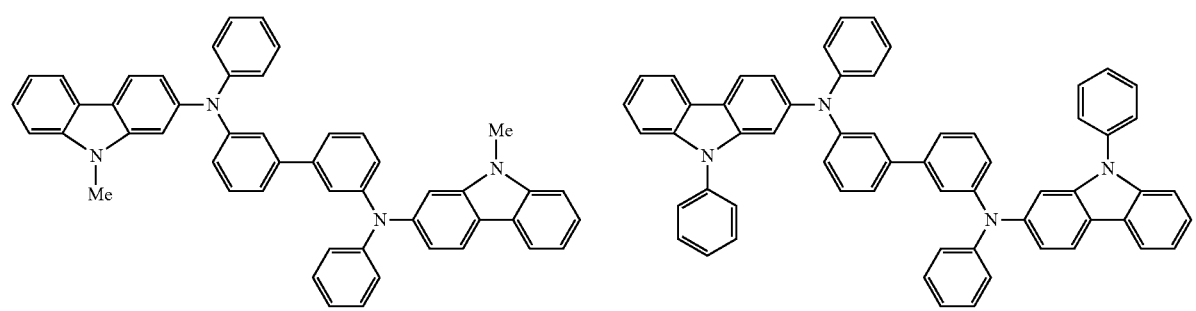
(D8)   (D9)

-continued
(D10)
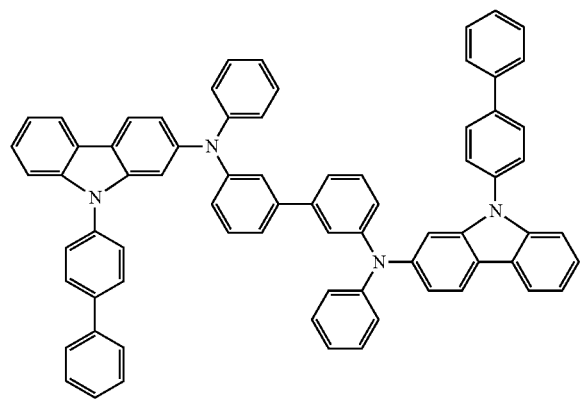
(D11)
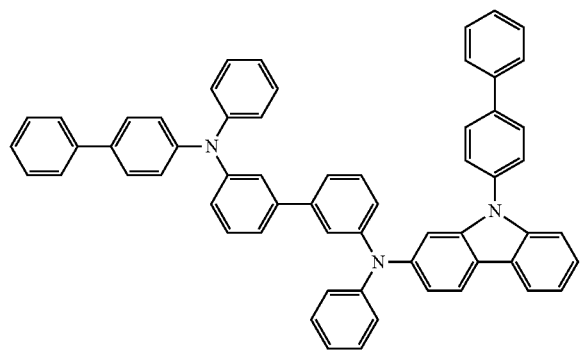
(D12)
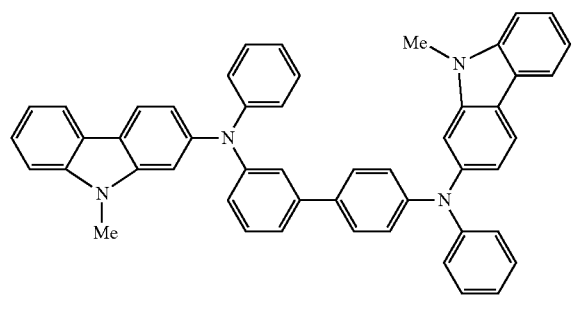
(D13)
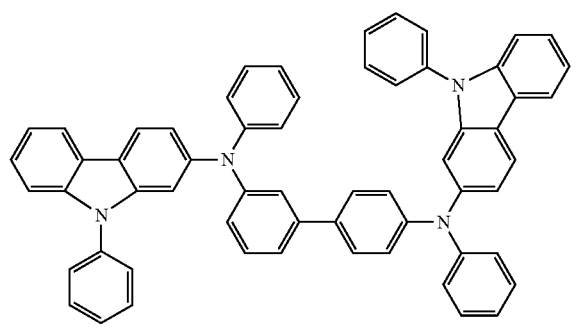
(D14)
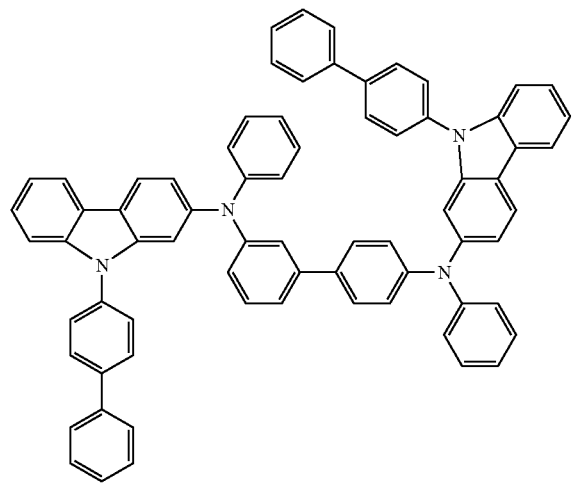
(D15)
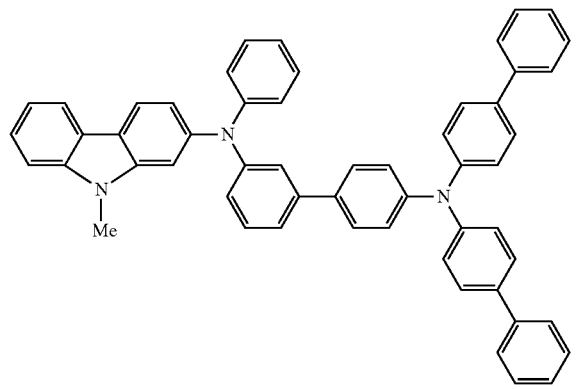
(D16)
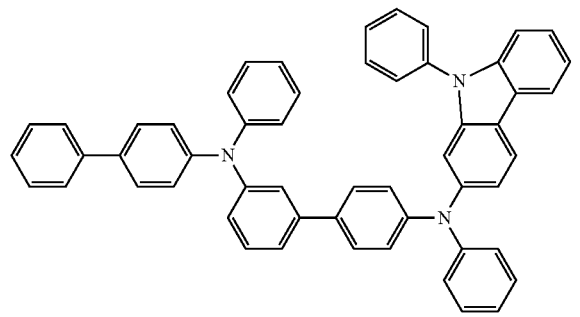
(D17)
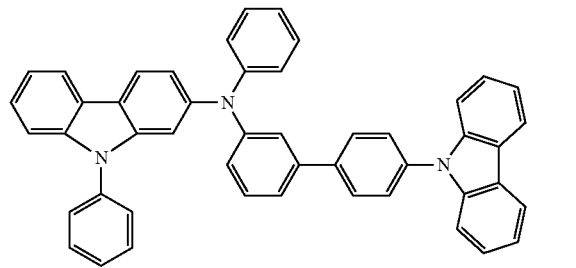

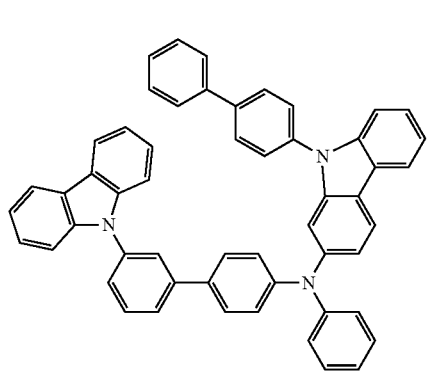
(D18)
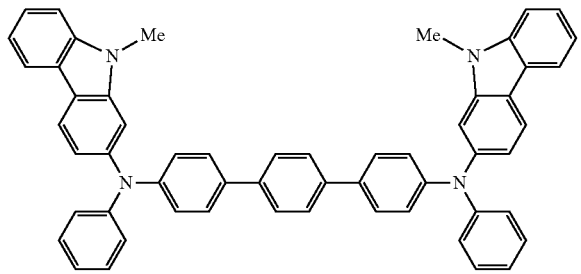
(E1)
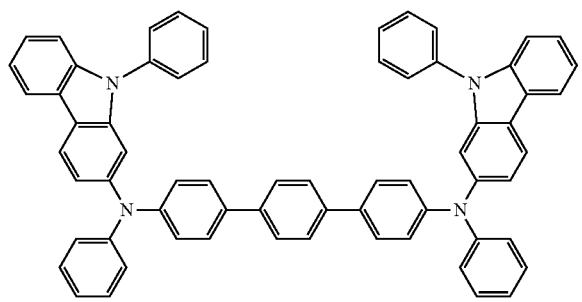
(E2)
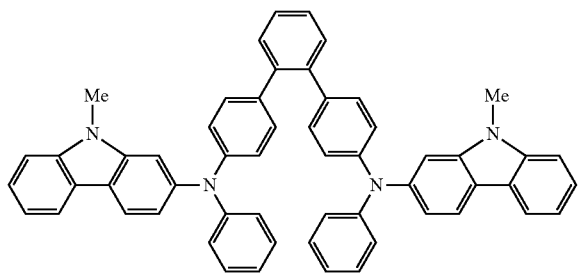
(E3)
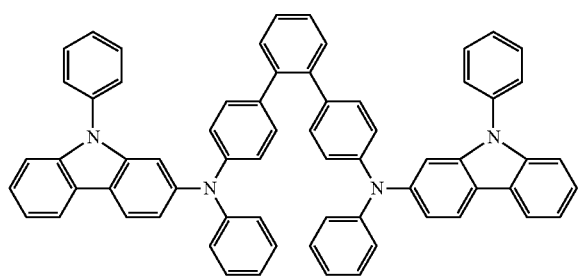
(E4)
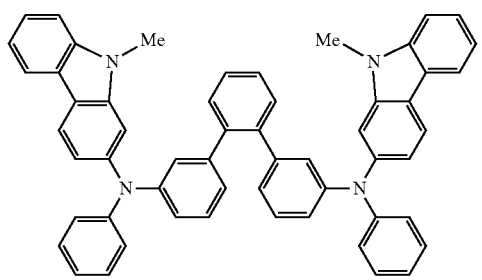
(E5)
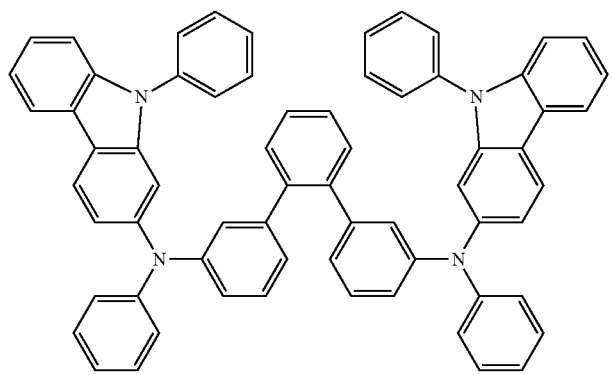
(E6)

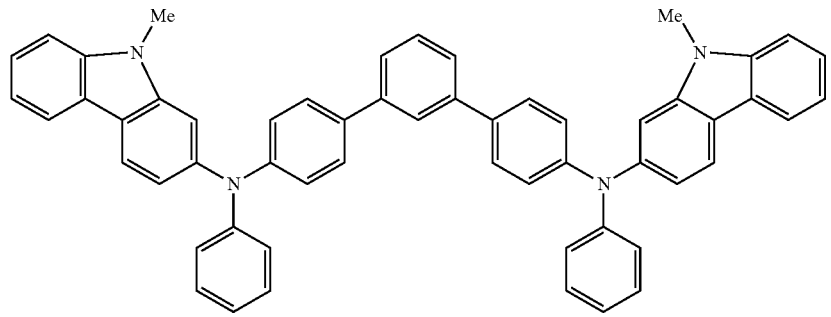
(E7)
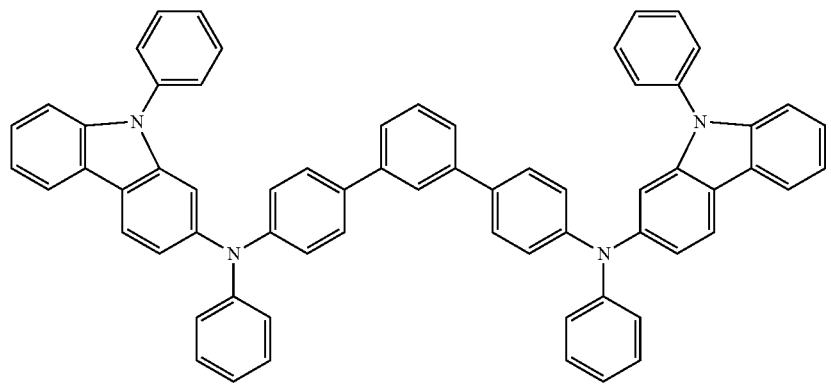
(E8)
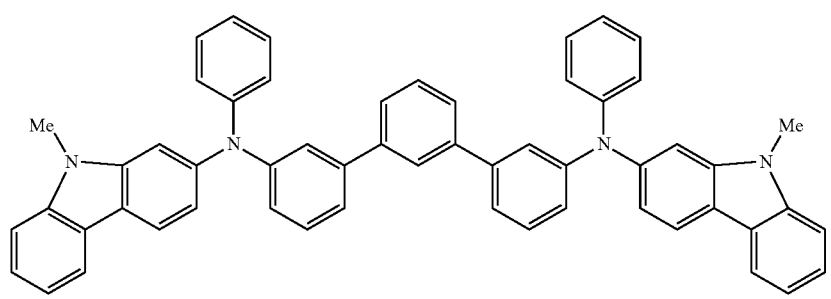
(E9)
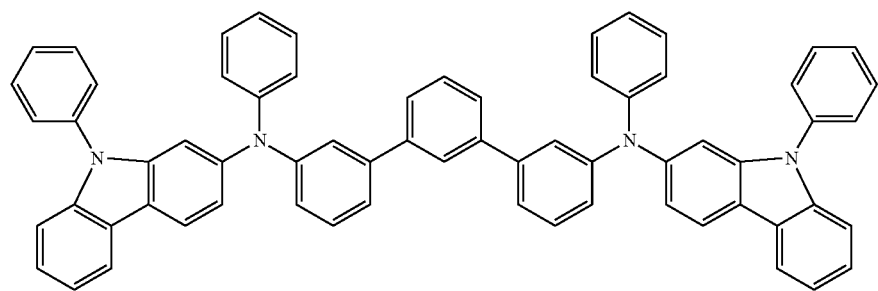
(E10)

-continued
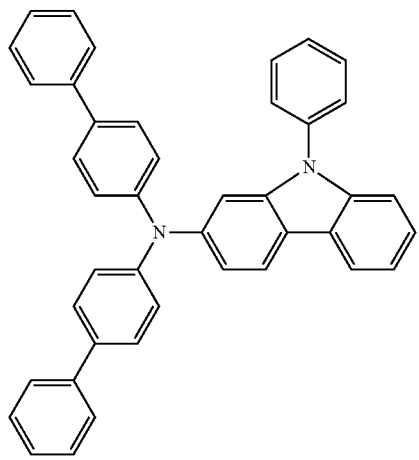 (F1)
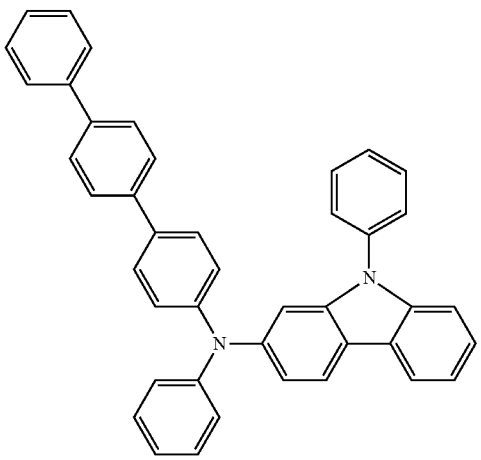 (F2)
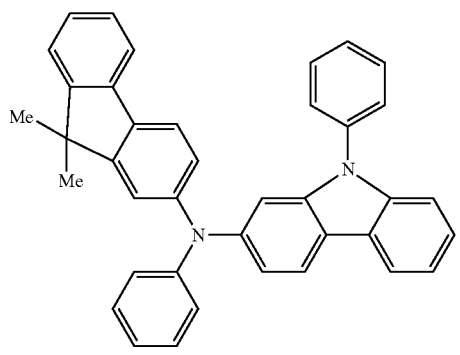 (F3)
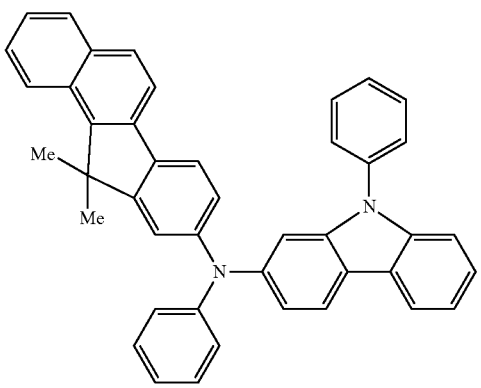 (F4)
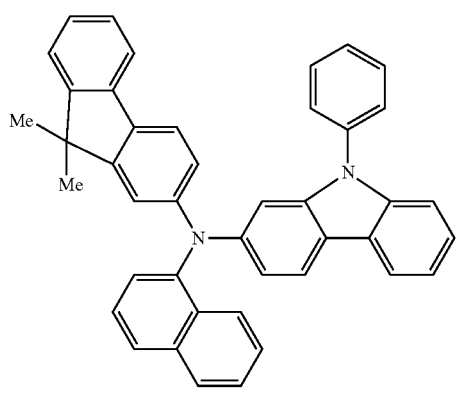 (F5)
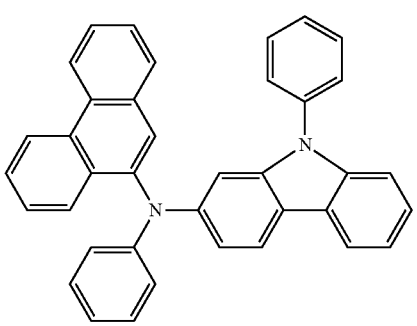 (F6)

-continued
(F7)
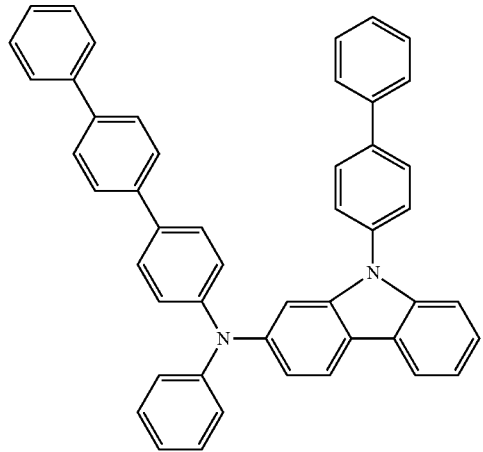
(F8)
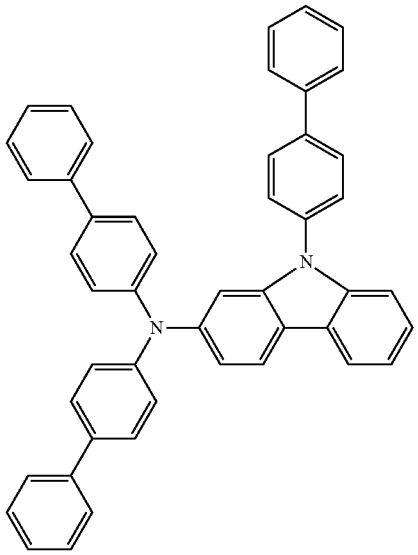
(F9)
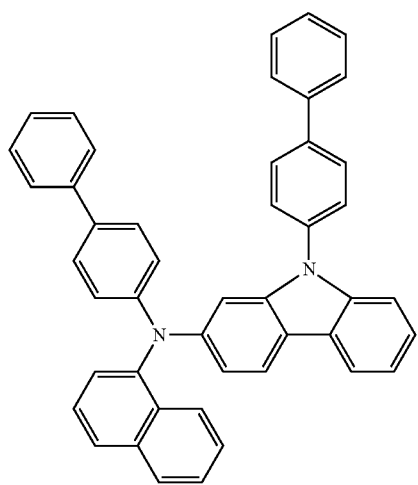
(F10)
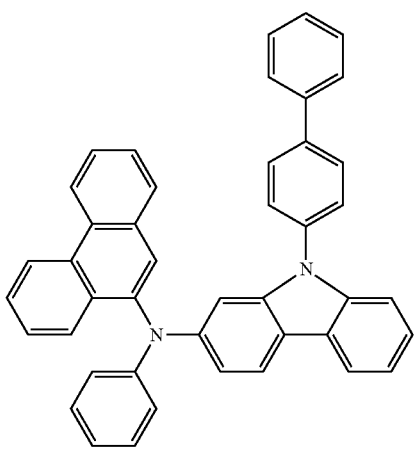
(F11)
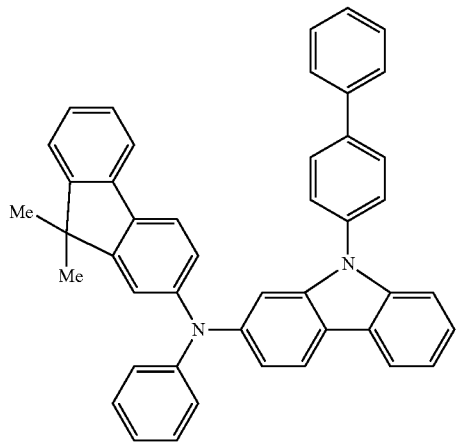
(F12)
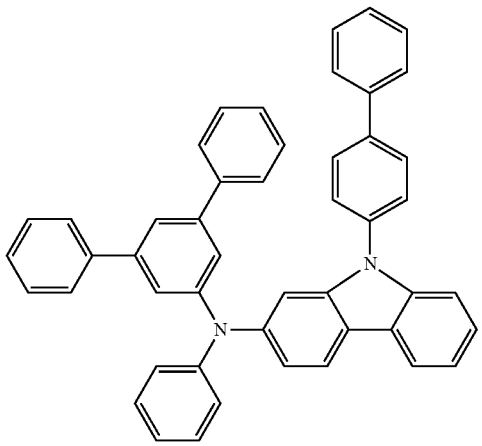

-continued
(F13)
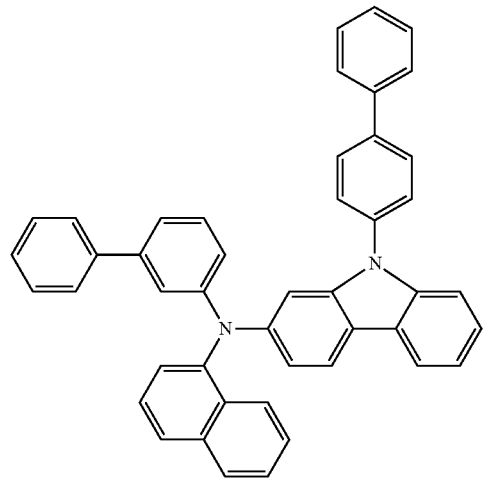
(F14)
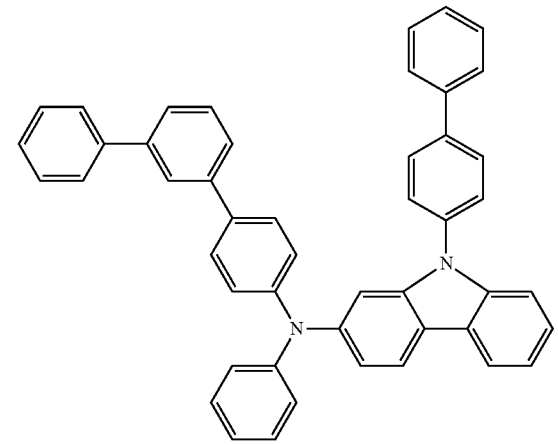
(F15)
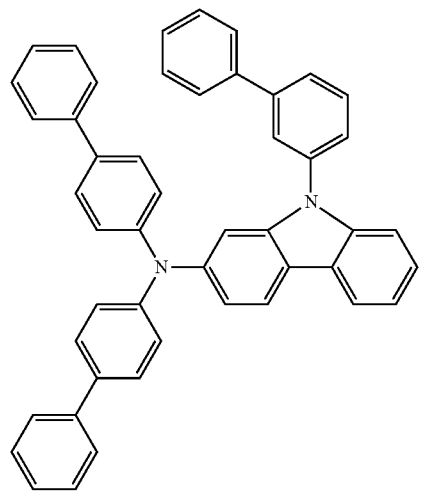
(F16)
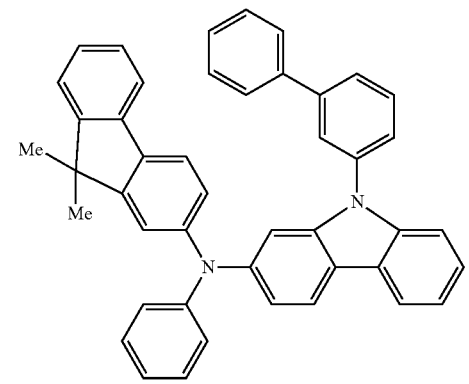
(F17)
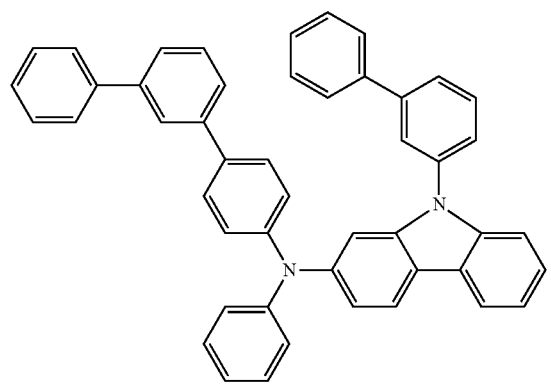
(F18)
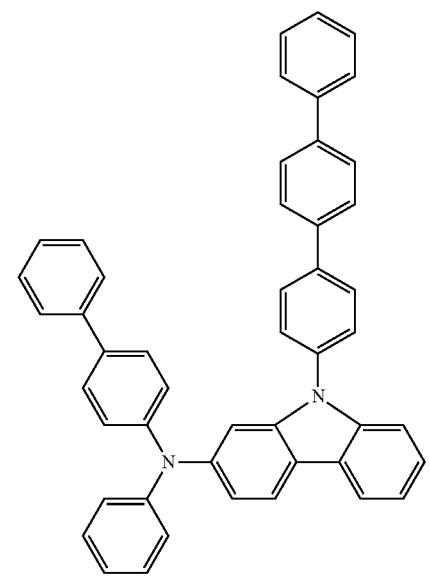

(F19)
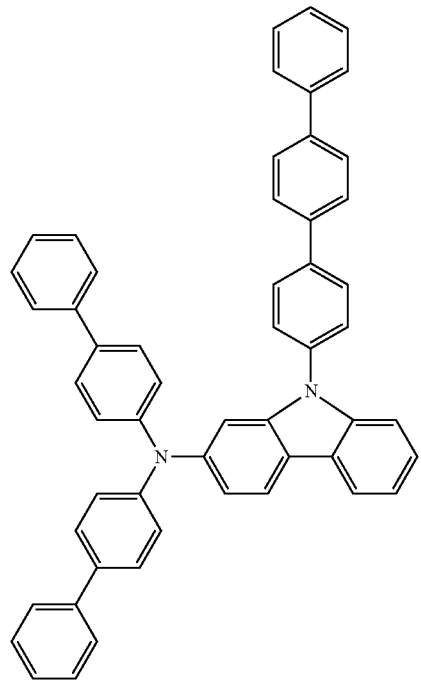
(F20)
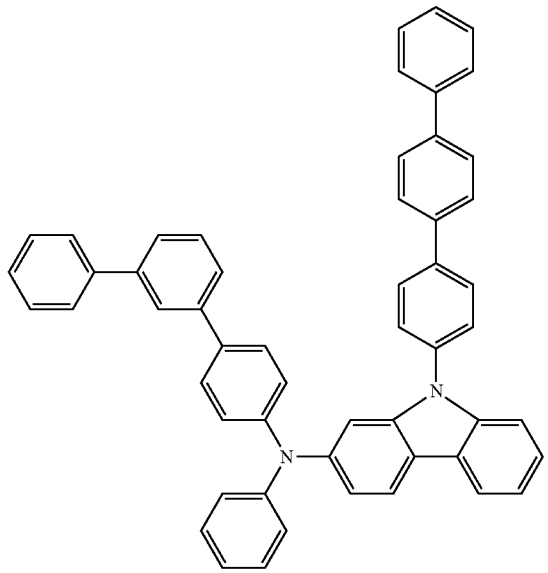
(F21)
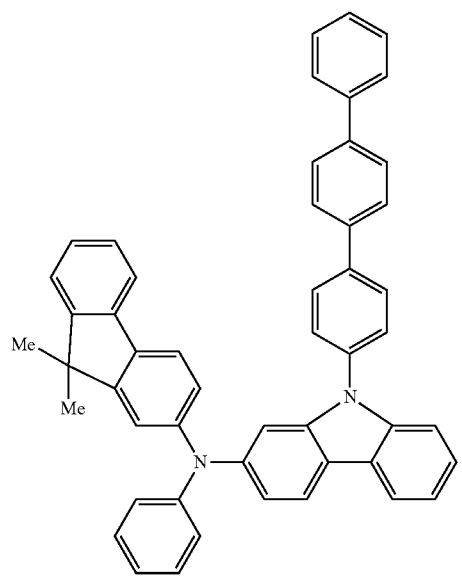
(F22)
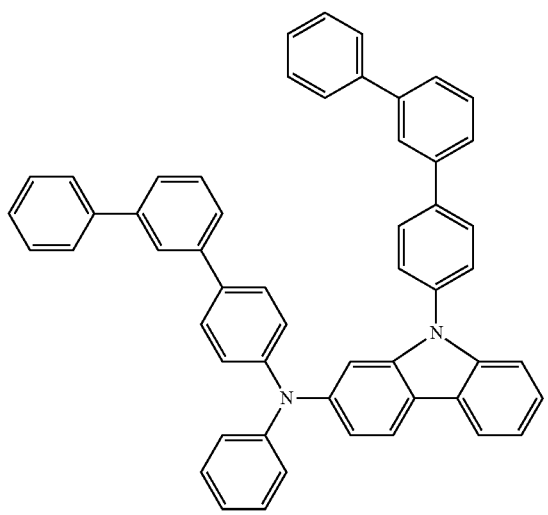

-continued
(F23)
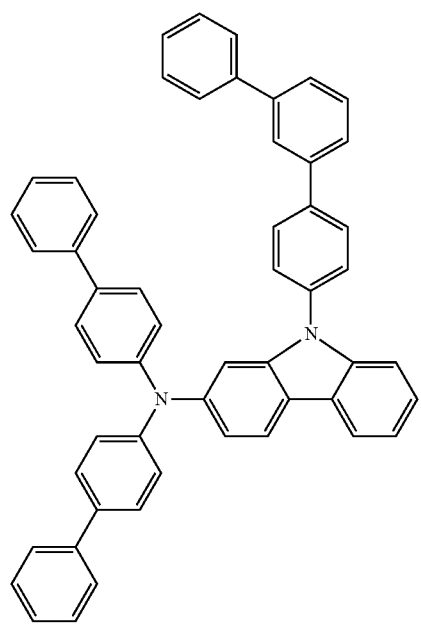
(F24)
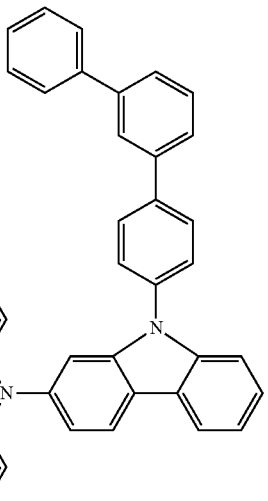
(F25)
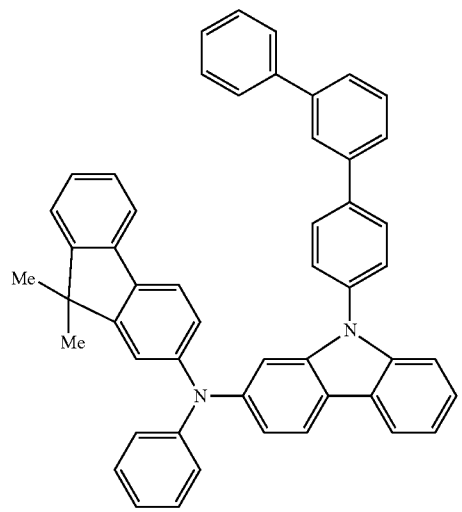
(F26)
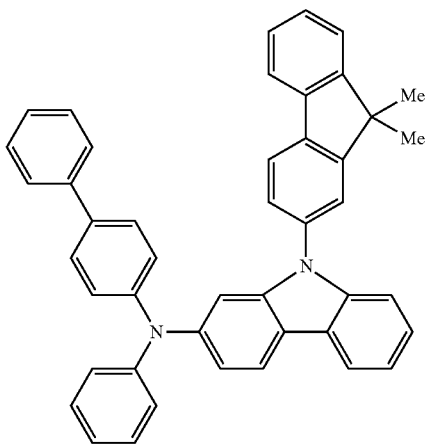
(F27)
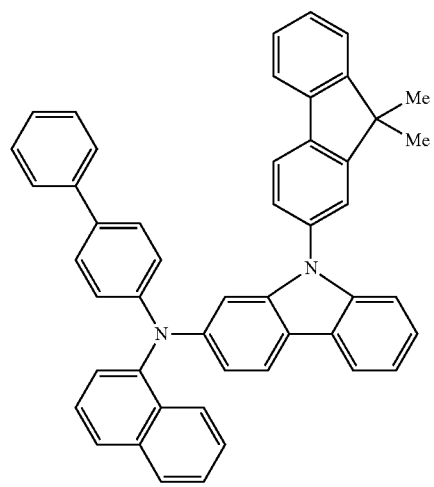
(F28)
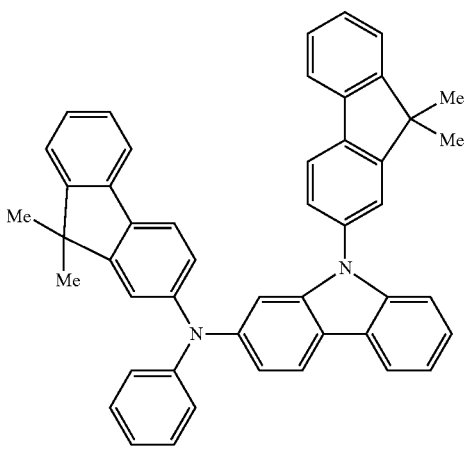

-continued
(F29)
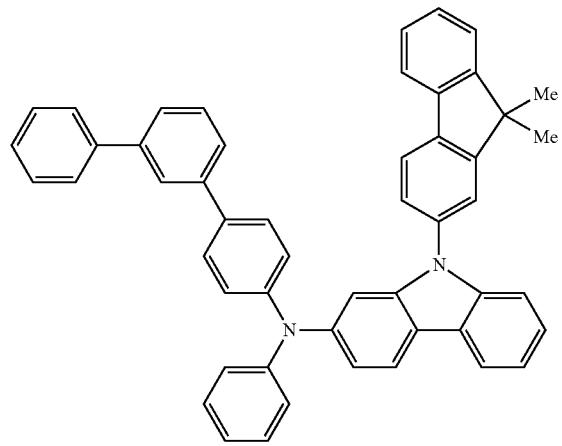
(F30)
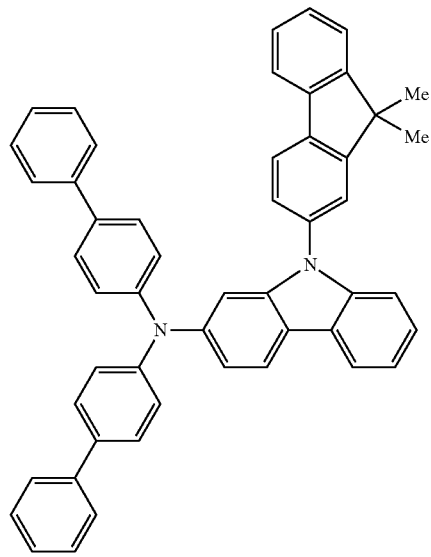
(F31)
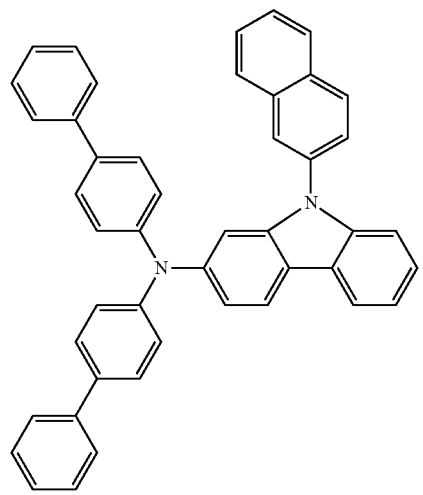
(F32)
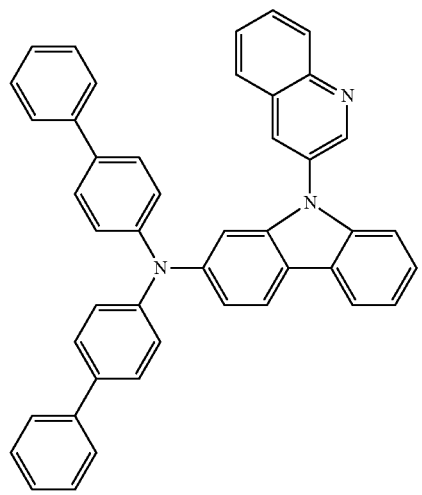
(F33)
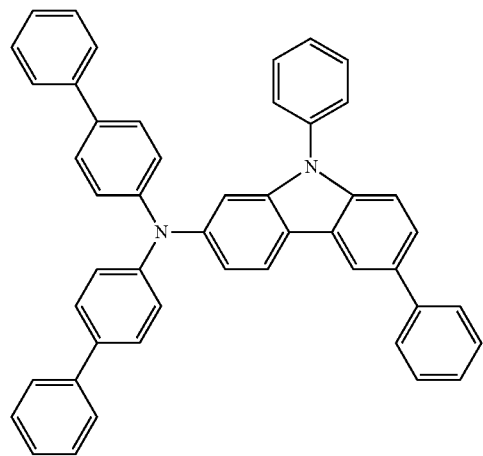
(F34)
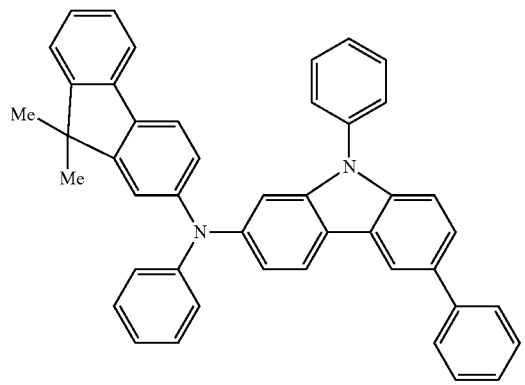

-continued
(F35)
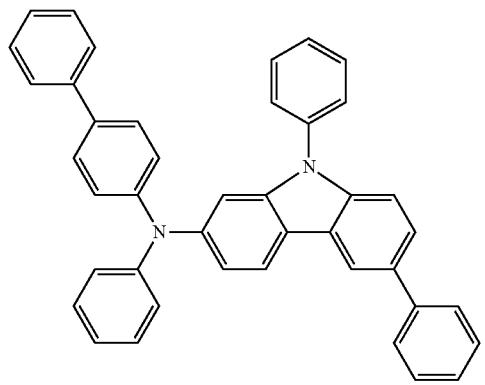
(F36)
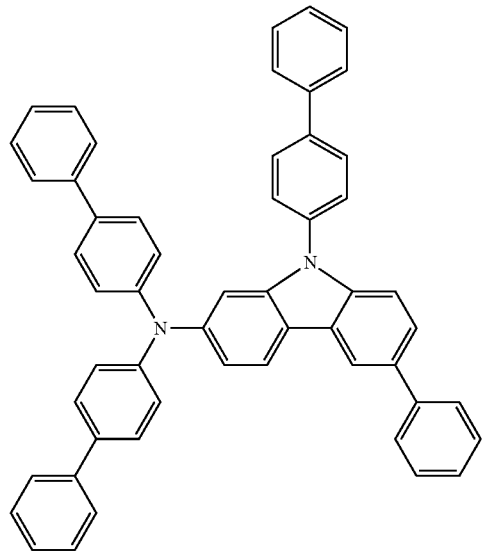
(F37)
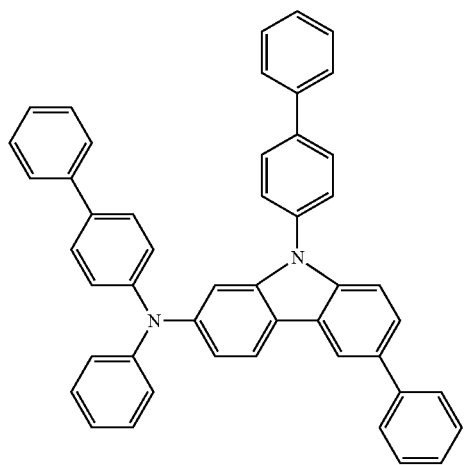
(F38)
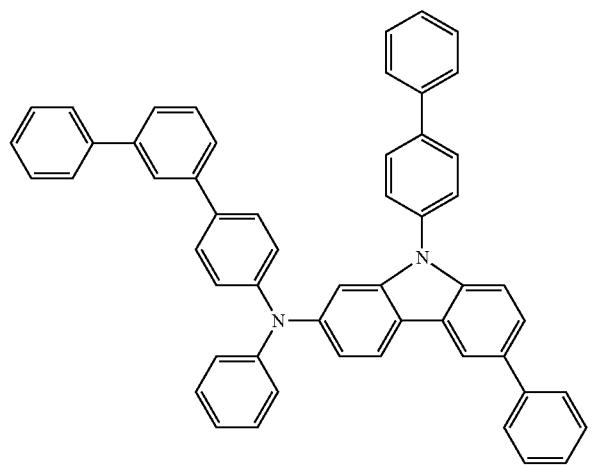
(F39)
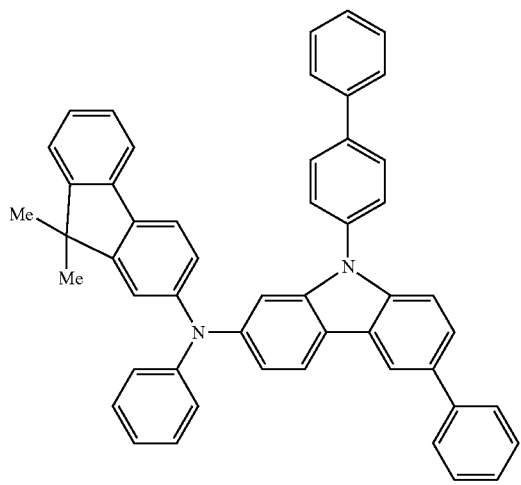
(F40)
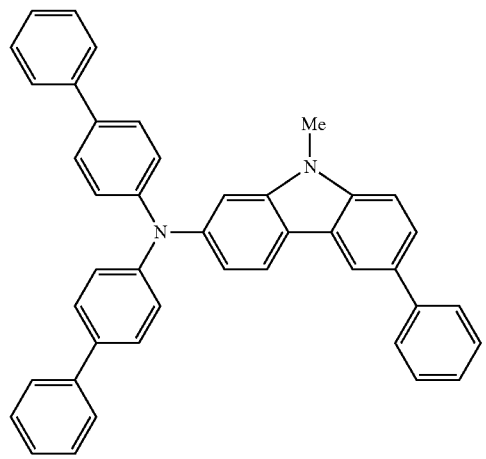

-continued (F41)
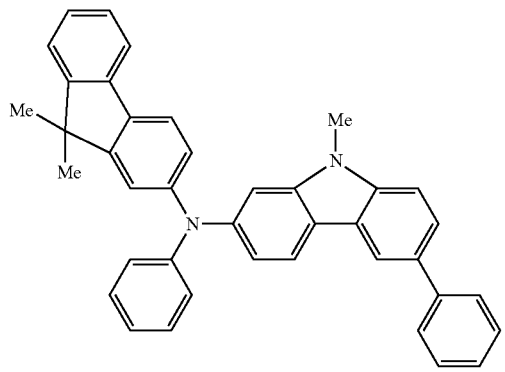

(F42)
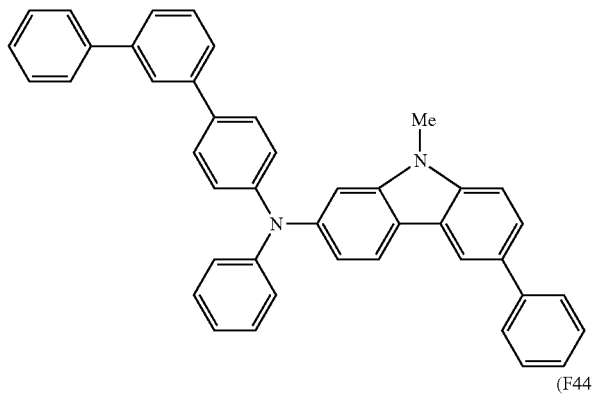

(F43)
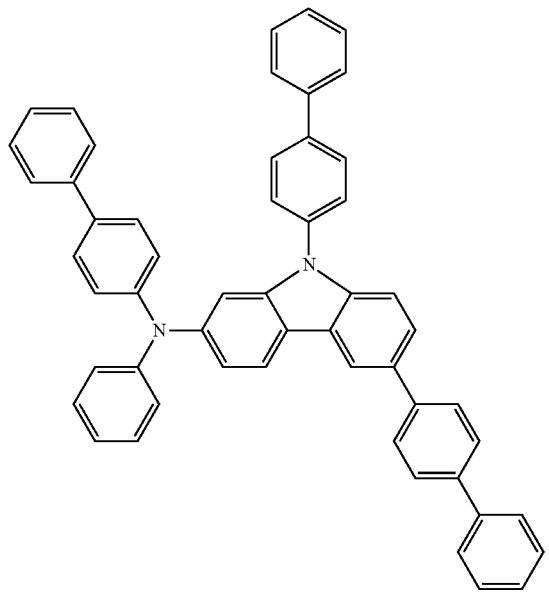

(F44)
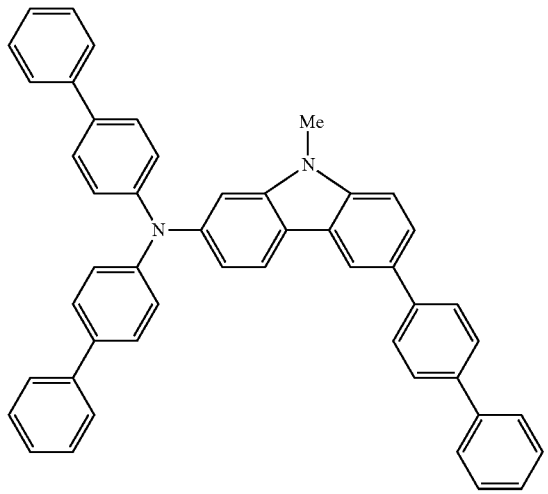

The carbazole compound of the formula (1) can be synthesized by a known method, for example, a method described in Tetrahedron Letters, 1998, vol. 39, p. 2367. More specifically the carbazole compound can be synthesized by reacting a carbazole compound having a halo substituent at a 2-position thereof with a secondary amine compound in the presence of a copper or palladium catalyst.

The carbazole compound of the formula (1) can be used as a material for constituting an emitting layer, a hole transport layer and a hole injection layer of an organic electroluminescent device.

The carbazole compound of the formula (1) exhibits excellent hole-transportability, and therefore, when it is used as a material for forming a hole transport layer and/or a hole injection layer, a resulting organic electroluminescent device exhibits improved drivability at a low voltage, a high luminous efficiency and an enhanced durability.

Further, the carbazole compound of the formula (1) exhibits a high triplet level as compared with the conventional hole transport materials, and therefore, even in the case when the emitting layer is formed from not only a fluorescent material but also a phosphorescent material, the carbazole compound exhibits enhanced luminous efficiency.

In the case when the carbazole compound of the formula (1) is used as a material for forming a hole transport layer and/or a hole injection layer, the conventional fluorescence emission material and the conventional phospholescence emission material can be used for forming an emitting layer. The emitting layer can be formed from a one kind of emission material, or the host material may be doped with one or more kinds of emission materials.

In the case when a hole injection layer and/or a hole transport layer is formed from the carbzaole compound of the formula (1), the hole injection layer and/or the hole transport layer may be formed from two or more kinds of materials, or each of the hole injection layer and the hole transport layer may be a laminate of two or more layers composed of different materials. More specifically conventional electron-accepting materials can be used in combination with the carbazole compound of the formula (1). The electron-accepting materials include, for example, molybdenum oxide and other oxides, and 7,7,8,8-tetracyanoquinodimethane, 2,3,5,6-tetrafluoro-7,7,8,8-tetracyanoquinodimethane, and hexacyanohexaazatriphenylene.

In the case when the carbazole compound of the formula (1) is used for the formation of an emitting layer of an organic EL device, the emitting layer can be formed from the carbazole compound of the formula (1) alone, from a conventional emitting host material doped with the carbazole compound of the formula (1), or from the carbazole compound of the formula (1) doped with a conventional dopant. The carbazole compound of the formula (1) exhibits a high triplet level, and therefore it is especially suitable as an emitting host material for an organic EL device using a phosphorescent material.

A hole injection layer, a hole transport layer or an emitting layer, which is comprised of the carbazole compound of the formula (1), can be formed by any conventional methods including a vacuum deposition method, a spin coating method and a casting method.

EXAMPLES

The invention will be described more in detail by the following examples that by no means limit the scope of the invention.

In the examples, the measurements according to $^1$H-NMR and $^{13}$C-NMR were conducted by using a Gemini 200 instrument available from Varian Inc.

The measurements according to field desorption mass spectrometry (FD-MS) were conducted by using "M-80B" instrument available from Hitachi Ltd.

Glass transition temperature was measured by using a differential scanning calorimeter "DSC-3100" available from MAC Science K.K. at a temperature elevation rate of 10° C./min.

Ionization potential was measured according to cyclic voltammetry analysis using HA-501 and HB-104 instruments available from Hokuto Denko Corporation.

Luminescent properties of organic EL devices were evaluated by using a luminance meter "LUMINANCEMETER BM-9" available from Topcon Technohouse Corporation, while a direct current is applied to the organic EL device.

Synthesis Example 1

Synthesis of 2-(4-chlorophenyl)nitrobenzene according to the reaction scheme (13), shown below.

In a stream of nitrogen, a 500 ml three-necked flask was charged with 25.0 g (123.0 mmol) of o-bromonitrobenzene, 21.1 g (135.3 mmol) of p-chlorophenylboric acid, 0.71 g (0.61 mmol) of tetrakis(triphenylphosphine)palladium, 100 g of tetrahydrofuran and 162 g (307.5 mmol) of an aqueous 20 weight % potassium carbonate solution, and the content was heated under reflux for 8 hours. The reaction mixture was cooled to room temperature, and separated into an aqueous phase and an organic phase. The organic phase was washed with an aqueous saturated ammonium chloride solution and then with an aqueous saturated sodium chloride solution, and then, dried over anhydrous magnesium sulfate. The dried solution was concentrated under a reduced pressure and the thus-obtained residue was purified by silica gel column chromatography using toluene as an eluent to give 27.2 g of 2-(4-chlorophenyl)nitrobenzene (yield: 94%).

The thus-obtained compound was identified by $^1$H-NMR and $^{13}$C-NMR measurements.

$^1$H-NMR (CDCl$_3$); 7.87 (d, 1H), 7.36-7.66 (m, 5H), 7.21-7.27 (m, 2H)

$^{13}$C-NMR (CDCl$_3$); 148.98, 135.85, 135.12, 134.37, 132.45, 131.79, 129.23, 128.84, 128.53, 124.21

Synthesis Example 2

Synthesis of 2-chlorocarbazole according to the reaction scheme (13), shown below.

In a stream of nitrogen, a 200 ml egg-plant flask was charged with 10.0 g (42.7 mmol) of 2-(4-chlorophenyl)nitrobenzene obtained in Synthesis Example 1, and then, 50 ml of triethyl phosphite was added. The mixture was stirred at 150° C. for 24 hours. The thus-obtained reaction mixture was distilled under a reduced pressure to remove triethyl phosphite. o-Xylene was added to the residue and then the solution was recrystallized from o-xylene give 5.1 g (25.6 mmol) of 2-chlorocarbazole as a white powder (yield: 60%).

The thus-obtained compound was identified by $^1$H-NMR and $^{13}$C-NMR measurements.

$^1$H-NMR (Acetone-d6); 10.46 (br-s, 1H), 8.10 (d, 2H), 7.37-7.55 (m, 3H), 7.15-7.24 (m, 2H)

$^{13}$C-NMR (Acetone-d6); 141.35, 141.15, 131.33, 126.70, 123.17, 122.64, 121.92, 120.84, 120.09, 119.78, 111.81, 111.43

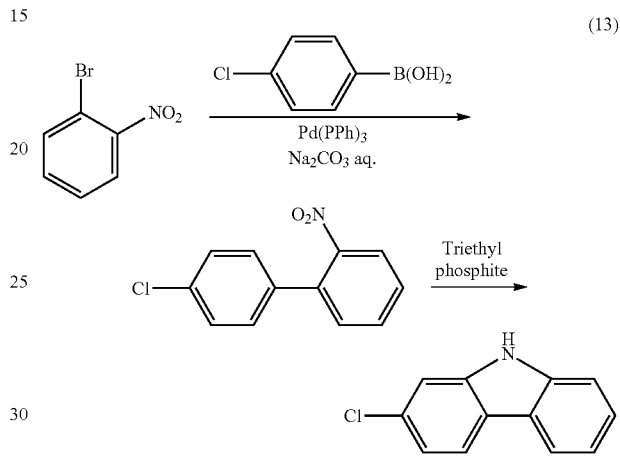

(13)

Synthesis Example 3

Synthesis of 2-chloro-9-(4-chlorophenyl)carbazole

In a stream of nitrogen, a 50 ml three-necked flask was charged with 1.6 g (7.9 mmol) of 2-chlorocarbazole obtained in Synthesis Example 2, 1.6 g (8.7 mmol) of p-bromochlorobenzene, 1.7 g (12.2 mmol) of potassium carbonate and 10 ml of o-xylene. To the thus-obtained reaction liquid of a slurry state, 19 mg (0.08 mmol) of palladium acetate and 61 mg (0.30 mmol) of tri(tert-butyl)phosphine were added, and the mixture was stirred at 130° C. for 24 hours. The reaction mixture was cooled to room temperature, and 10 g of pure water was added thereto to separate an organic phase. The organic phase was washed with water and then with an aqueous saturated sodium chloride solution. Then the organic phase was dried over anhydrous magnesium sulfate. The dried organic phase was concentrated under a reduced pressure and the thus-obtained residue was purified by silica gel column chromatography using hexane as an eluent to give 1.6 g (5.1 mmol) of 2-chloro-9-(4-chlorophenyl)carbazole as a white solid (yield: 64%).

The thus-obtained compound was identified by $^1$H-NMR and $^{13}$C-NMR measurements.

$^1$H-NMR (CDCl$_3$); 8.08 (d, 1H), 8.01 (d, 1H), 7.58 (d, 2H), 7.22-7.58 (m, 7H)

$^{13}$C-NMR (CDCl$_3$); 141.20, 141.00, 135.58, 133.53, 131.83, 130.27, 128.35, 126.31, 122.82, 121.97, 121.19, 120.66, 120.62, 120.31, 109.69

Synthesis Example 4

Synthesis of 1,4-bis(2-chlorocarbazol-9-yl)benzene

In a stream of nitrogen, a 50 ml three-necked flask was charged with 2.0 g (9.9 mmol) of 2-chlorocarbazole obtained in Synthesis Example 2, 1.1 g (4.7 mmol) of 1,4-diiodobenzene, 1.9 g (13.8 mmol) of potassium carbonate and 10 ml of o-xylene. To the thus-obtained reaction liquid of a slurry state, 5 mg (0.02 mmol) of palladium acetate and 15 mg (0.07 mmol) of tri(tert-butyl) phosphine were added, and the mixture was stirred at 130° C. for 15 hours. The reaction mixture was cooled to room temperature, and the thus-obtained precipitate was collected by filtration. The collected solid was washed with pure water and then with methanol, and then, dried under a reduced pressure. The dried solid was recrystallized from o-xylene to give 1.1 g (2.3 mmol) of 1,4-bis(2-chlorocarbazol-9-yl)benzene as a white needle crystal (yield: 48%).

The thus-obtained compound was identified by $^1$H-NMR measurement.

$^1$H-NMR (CDCl$_3$); 8.14 (d, 2H), 8.08 (d, 2H), 7.81 (s, 4H), 7.45-7.56 (m, 6H), 7.28-7.39 (m, 4H)

Example 1

Synthesis of Compound (A2) and Evaluation of Stability of Film

In a stream of nitrogen, a 50 ml three-necked flask was charged with 0.7 g (2.2 mmol) of 2-chloro-9-(4-chlorophenyl)carbazole obtained in Synthesis Example 3, 1.2 g (4.9 mmol) of N-phenyl-N-biphenylylamine, 680 mg (4.9 mmol) of sodium tert-butoxide and 10 ml of o-xylene. To the thus-obtained reaction liquid of a slurry state, 11 mg (0.05 mmol) of palladium acetate and 34 mg (0.17 mmol) of tri(tert-butyl)phosphine were added, and the mixture was stirred at 130° C. for 12 hours. The reaction mixture was cooled to room temperature, and then, 10 g of pure water was added to the reaction mixture and the mixture was stirred. The reaction mixture was separated into an aqueous phase and an organic phase. The organic phase was washed with pure water and then with an aqueous saturated sodium chloride solution, and then, the washed organic phase was dried over anhydrous magnesium sulfate. The dried organic phase was concentrated under a reduced pressure, and the thus-obtained brown solid was washed with ethanol to give 1.3 g (1.78 mmol) of the compound (A2) as a white solid (yield: 79%).

The compound (A2) was identified by the measurement according to FDMS.

FDMS: 729

A thin film was formed on a glass sheet from the compound (A2) by vacuum deposition. Even when the film was left to stand for one month at room temperature, it did not become whitely clouded (i.e., not coagulated nor crystallized). The glass transition temperature (Tg) of the compound (A2) was 101° C., that is, higher than Tg (96° C.) of a conventional NPD material.

Example 2

Synthesis of Compound (A3) and Evaluation of Stability of Film

In a stream of nitrogen, a 50 ml three-necked flask was charged with 0.7 g (2.2 mmol) of 2-chloro-9-(4-chlorophenyl)carbazole obtained in Synthesis Example 3, 1.5 g (4.9 mmol) of N,N-bis(biphenylyl)amine, 680 mg (4.92 mmol) of sodium tert-butoxide and 10 ml of o-xylene. To the thus-obtained reaction liquid of a slurry state, 11 mg (0.05 mmol) of palladium acetate and 34 mg (0.17 mmol) of tri(tert-butyl)phosphine were added, and the mixture was stirred at 130° C. for 18 hours. The reaction mixture was cooled to room temperature, and then, 10 g of pure water was added to the reaction mixture and the mixture was stirred. Then the reaction mixture was separated into an aqueous phase and an organic phase. The organic phase was washed with pure water and then with an aqueous saturated sodium chloride solution, and then, the washed organic phase was dried over anhydrous magnesium sulfate. The dried organic phase was concentrated under a reduced pressure, and the thus-obtained brown solid was recrystallized from o-xylene to give 1.1 g (1.2 mmol) of the compound (A3) as a white solid (yield: 55%).

The compound (A3) was identified by the measurement according to FDMS.

FDMS: 882

A thin film was formed on a glass sheet from the compound (A3) by the same procedure as described in Example 1. Even when the film was left to stand for one month at room temperature, it did not become whitely clouded (i.e., not coagulated nor crystallized). The glass transition temperature (Tg) of the compound (A3) was 138° C., that is, higher than Tg (96° C.) of a conventional NPD material.

Example 3

Synthesis of Compound (B7) and Evaluation of Stability of Film

In a stream of nitrogen, a 50 ml three-necked flask was charged with 1.0 g (2.1 mmol) of 1,4-bis(2-chlorocarbazol-9-yl)benzene obtained in Synthesis Example 4, 780 mg (4.6 mmol) of diphenylamine, 560 mg (5.8 mmol) of sodium tert-butoxide and 17 ml of o-xylene. To the thus-obtained reaction liquid of a slurry state, 9 mg (0.04 mmol) of palladium acetate and 29 mg (0.14 mmol) of tri(tert-butyl) phosphine were added, and the mixture was stirred at 130° C. for 24 hours. The reaction mixture was cooled to room temperature, and then, 10 g of pure water was added to the reaction mixture and the mixture was stirred. Then the thus-produced precipitate was collected by filtration, and the obtained white solid was washed with water and then with ethanol. The washed white solid was dried under a reduced pressure, and the dried solid was recrystallized from o-xylene to give 1.0 g (1.3 mmol) of the compound (B7) as a white powder (yield: 61%).

The compound (B7) was identified by the measurement according to FDMS.

FDMS: 742

A thin film was formed on a glass sheet from the compound (B7) by the same procedure as described in Example 1. Even when the film was left to stand for one month at room temperature, it did not become whitely clouded (i.e., not coagulated nor crystallized). The glass transition temperature (Tg) of the compound (B7) was 122° C., that is, higher than Tg (96° C.) of a conventional NPD material.

Example 4

Synthesis of Compound (B10) and Evaluation of Stability of Film

In a stream of nitrogen, a 50 ml three-necked flask was charged with 1.5 g (3.1 mmol) of 1,4-bis(2-chlorocarbazol-9-yl)benzene obtained in Synthesis Example 4, 1.6 g (6.8 mmol) of N-phenyl-N-biphenylylamine, 914 mg (9.5 mmol) of sodium tert-butoxide and 20 ml of o-xylene. To the thus-obtained reaction liquid of a slurry state, 15 mg (0.06 mmol) of palladium acetate and 42 mg (0.21 mmol) of tri(tert-butyl)phosphine were added, and the mixture was stirred at 130° C. for 24 hours. The reaction mixture was cooled to room temperature, and then, 10 g of pure water was added to the reaction mixture and the mixture was stirred. Then the thus-produced precipitate was collected by filtration, and the obtained white solid was washed with water and then with ethanol. The washed solid was dried under a reduced pressure, and the dried solid was recrystallized from o-xylene to give 1.9 g (2.2 mmol) of the compound (B10) as a white powder (yield: 72%).

The compound (B10) was identified by the measurement according to FDMS.

FDMS: 895

A thin film was formed on a glass sheet from the compound (B10) by the same procedure as described in Example 1. Even when the film was left to stand for one month at room temperature, it did not become whitely clouded (i.e., not coagulated nor crystallized). The glass transition temperature (Tg) of the compound (B10) was 132° C., that is, higher than Tg (96° C.) of a conventional NPD material.

Example 5

Evaluation of Ionization Potential of Compound (A2)

The compound (A2) was dissolved at a concentration of 0.001 mol/L in a tetrabutylammonium perchlorate solution in anhydrous dichloromethane having a concentration of 0.1 mol/L. Ionization potential of the compound (A2) was measured on the compound (A2) solution by means of cyclic volutammetry analysis. In the cyclic volutammmetry analysis, glassy carbon was used as a working electrode, a platinum wire was used as a counter electrode, a silver wire dipped with a solution of $AgNO_3$ in acetonitrile was used as a reference electrode, and ferrocene was used as a standard material.

The ionization potential of the compound (A2) was 0.39V vs. $Fc/Fc^+$, as expressed on a basis of the oxidation-reduction potential of ferrocene as reference standard. Thus, the ionization potential of the compound (A2) was approximately the same as that (0.31V vs. $Fc/Fc^+$) of NPD which is conventionally used as a hole transport material.

Example 6

Evaluation of Ionization Potential of Compound (A3)

Ionization potential of the compound (A3) was evaluated by the same procedure as described in Example 5. The ionization potential of the compound (A3) was 0.37V vs. $Fc/Fc^+$, and thus, approximately the same as that (0.31V vs. $Fc/Fc^+$) of NPD conventionally used as a hole transport material.

Example 7

Evaluation of Ionization Potential of Compound (B7)

Ionization potential of the compound (B7) was evaluated by the same procedure as described in Example 5. The ionization potential of the compound (B7) was 0.40V vs. $Fc/Fc^+$, and thus, approximately the same as that (0.31V vs. $Fc/Fc^+$) of NPD conventionally used as a hole transport material.

Example 8

Evaluation of Ionization Potential of Compound (B10)

Ionization potential of the compound (B10) was evaluated by the same procedure as described in Example 5. The ionization potential of the compound (B10) was 0.39V vs. $Fc/Fc^+$, and thus, approximately the same as that (0.31V vs. $Fc/Fc^+$) of NPD conventionally used as a hole transport material.

Comparative Example 1

Evaluation of Ionization Potential of Comparative Compound (a)

Ionization potential of a comparative compound (a), i.e., a carbazole compound having a structure such that an amino group is bonded to 3-positions of the two carbazole rings, which is represented by the chemical structure shown below, was evaluated by the same procedure as described in Example 5. The ionization potential of the comparative compound (a) was 0.13V vs. $Fc/Fc^+$, and thus, smaller than that (0.31V vs. $Fc/Fc^+$) of NPD conventionally used as a hole transport material.

Comparative Compound (a)

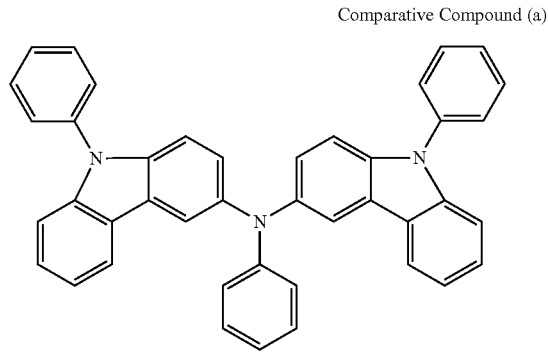 [SMILES: c1ccc(N(c2ccc3c(c2)c2ccccc2n3-c2ccccc2)c2ccc3c(c2)c2ccccc2n3-c2ccccc2)cc1]

Example 9

Evaluation of Device Made by Using Compound (A2)

An organic EL device for evaluation was made as follows. A glass substrate having laminated thereon an indium-tin oxide (ITO) transparent electrode (anode) with a thickness of 200 nm was washed with acetone and then with pure water, while being irradiated with ultrasonic wave, and then washed with boiling isopropyl alcohol. The washed substrate was further treated by irradiation with ultraviolet rays while ozone was generated. The thus-treated glass substrate was placed in a vacuum evaporation chamber, and the inner pressure was reduced to $1 \times 10^{-4}$ Pa by a vacuum pump. Phthalocyanine copper was vapor-deposited at a deposition rate of 0.1 nm/sec on the transparent ITO electrode to form a hole injection layer with a thickness of 25 nm. Then the compound (A2) was vapor-deposited on the hole injection layer at a deposition rate of 0.3 nm/sec to form a hole transport layer with a thickness of 40 nm. Tris(8-quinolinolate)aluminum (hereinafter referred to "$Alq_3$" for brevity when appropriate) was vapor-deposited on the hole transport layer at a deposition rate of 0.3 nm/sec to form an emitting layer with a thickness of 60 nm, and then, lithium fluoride was vapor-deposited on the emitting layer at a deposition rate of 0.01 nm/sec to form an electron injection layer with a thickness of 0.5 nm. Further aluminum was vapor-deposited on the electron injection layer at a deposition rate of 0.25 nm/sec to form a cathode with a thickness of 100 nm. A thus-obtained assembly was encapsulated with a glass sheet and an UV-curable resin in an atmosphere of nitrogen gas to give an organic EL device for evaluation.

Driving voltage and external quantum efficiency of the organic EL device were measured at a current density of 20 mA/cm². The results are shown in Table 1, below.

Example 10

Evaluation of Device Made by Using Compound (A3)

An organic EL device for evaluation was made by the same procedure as described in Example 9 except that the compound (A3) was used instead of the compound (A2), and driving voltage and external quantum efficiency of the organic EL device were measured at a current density of 20 mA/cm². The results are shown in Table 1, below.

Example 11

Evaluation of Device Made by Using Compound (B7)

An organic EL device for evaluation was made by the same procedure as described in Example 9 except that the compound (B7) was used instead of the compound (A2), and driving voltage and external quantum efficiency of the organic EL device were measured at a current density of 20 mA/cm². The results are shown in Table 1, below.

Example 12

Evaluation of Device Made by Using Compound (B10)

An organic EL device for evaluation was made by the same procedure as described in Example 9 except that the compound (B10) was used instead of the compound (A2), and driving voltage and external quantum efficiency of the organic EL device were measured at a current density of 20 mA/cm². The results are shown in Table 1, below.

Comparative Example 2

An organic EL device for comparative evaluation was made by the same procedure as described in Example 9 except that NPD was used instead of the compound (A2), and driving voltage and external quantum efficiency of the organic EL device were measured at a current density of 20 mA/cm². The results are shown in Table 1, below.

Comparative Example 3

An organic EL device for comparative evaluation was made by the same procedure as described in Example 9 except that the comparative compound (a) was used instead of the compound (A2), and driving voltage and external quantum efficiency of the organic EL device were measured at a current density of 20 mA/cm². The results are shown in Table 1, below.

TABLE 1

|  | Compound in hole transport layer | Driving voltage (V) | External quantum efficiency (%) |
| --- | --- | --- | --- |
| Example 9 | (A2) | 5.4 | 1.01 |
| Example 10 | (A3) | 5.1 | 1.03 |
| Example 11 | (B7) | 5.3 | 1.05 |
| Example 12 | (B10) | 5.4 | 1.04 |
| Com. Ex. 2 | NPD | 5.8 | 0.92 |
| Com. Ex. 3 | Comparative compound (a) | 6.0 | 0.81 |

Example 13

Evaluation of Device Made by Using Compound (A2)

An organic EL device for evaluation was made as follows. A glass substrate having laminated thereon an indium-tin oxide (ITO) transparent electrode (anode) with a thickness of 200 nm was washed with acetone and then with pure water, while being irradiated with ultrasonic wave, and then washed with boiling isopropyl alcohol. The substrate was further treated by irradiation with ultraviolet rays while ozone was generated. The thus-treated glass substrate was placed in a vacuum evaporation chamber, and the inner pressure was reduced to $1\times10^{-4}$ Pa by a vacuum pump. NPD was vapor-deposited at a deposition rate of 0.3 nm/sec on the transparent ITO electrode to form a hole injection layer with a thickness of 20 nm. Then the compound (A2) was vapor-deposited on the hole injection layer at a deposition rate of 0.3 nm/sec to form a hole transport layer with a thickness of 30 nm. Tris(2-phenylpyridine)iridium (hereinafter referred to "Ir(ppy)$_3$" for brevity when appropriate) as a phospholuminous dopant material and 4,4'-bis(N-carbazolyl)biphenyl (hereinafter referred to "CBP" for brevity when appropriate) as a host material were co-vapor-deposited on the hole transport layer at a weight ratio of 1:11.5 and at a deposition rate of 0.25 nm/sec to form an emitting layer with a thickness of 20 nm.

Then 2,9-dimethyl-4,7-diphenyl-1,10-phenanthroline (hereinafter referred to "BCP" for brevity when appropriate) was vapor-deposited on the emitting layer at a deposition rate of 0.3 nm/sec to form an exciton blocking layer with a thickness of 10 nm. Alq$_3$ was vapor-deposited on the exciton blocking layer at a deposition rate of 0.3 nm/sec to form an electron transport layer with a thickness of 30 nm. Then lithium fluoride was vapor-deposited on the electron transport layer at a deposition rate of 0.01 nm/sec to form an electron injection layer with a thickness of 0.5 nm. Further aluminum was vacuum-deposited on the electron injection layer at a deposition rate of 0.25 nm/sec to form a cathode with a thickness of 100 nm. A thus-obtained assembly was encapsulated with a glass sheet and an UV-curable resin in an atmosphere of nitrogen gas to give an organic EL device for evaluation.

Driving voltage and external quantum efficiency of the organic EL device were measured at a current density of 20 mA/cm². The results are shown in Table 2, below.

Example 14

Evaluation of Device Made by Using Compound (A3)

An organic EL device for evaluation was made by the same procedure as described in Example 13 except that the compound (A3) was used instead of the compound (A2), and driving voltage and external quantum efficiency of the organic EL device were measured at a current density of 20 mA/cm². The results are shown in Table 2, below.

Example 15

Evaluation of Device Made by Using Compound (B7)

An organic EL device for evaluation was made by the same procedure as described in Example 13 except that the compound (B7) was used instead of the compound (A2), and driving voltage and external quantum efficiency of the

Example 16

Evaluation of Device Made by Using Compound (B10)

An organic EL device for evaluation was made by the same procedure as described in Example 13 except that the compound (B10) was used instead of the compound (A2), and driving voltage and external quantum efficiency of the organic EL device were measured at a current density of 20 mA/cm$^2$. The results are shown in Table 2, below.

Comparative Example 4

An organic EL device for comparative evaluation was made by the same procedure as described in Example 13 except that NPD was used instead of the compound (A2), and driving voltage and external quantum efficiency of the organic EL device were measured at a current density of 20 mA/cm$^2$. The results are shown in Table 2, below.

TABLE 2

|  | Compound in hole transport layer | Driving voltage (V) | External quantum efficiency (%) |
| --- | --- | --- | --- |
| Example 13 | (A2) | 8.5 | 12.0 |
| Example 14 | (A3) | 8.1 | 11.5 |
| Example 15 | (B7) | 8.4 | 12.3 |
| Example 16 | (B10) | 8.3 | 12.2 |
| Com. Ex. 4 | NPD | 8.8 | 8.70 |

Synthesis Example 5

Synthesis of 2-chloro-9-phenylcarbazole

In a stream of nitrogen, a 50 ml three-necked flask was charged with 4.0 g (19.8 mmol) of 2-chlorocarbazole obtained in Synthesis Example 2, 15.4 g (99.4 mmol) of bromobenzene, 3.8 g (27.7 mmol) of potassium carbonate and 10 ml of o-xylene. To the thus-obtained reaction liquid of a slurry state, 44 mg (0.19 mmol) of palladium acetate and 0.14 g (0.69 mmol) of tri(tert-butyl) phosphine were added, and the mixture was stirred at 130° C. for 24 hours. The reaction mixture was cooled to room temperature, and 10 g of pure water was added thereto to separate an organic phase. The organic phase was washed with water and then with an aqueous saturated sodium chloride solution. Then the organic phase was dried over anhydrous magnesium sulfate. The dried organic phase was concentrated under a reduced pressure and the thus-obtained residue was purified by silica-gel column chromatography using a mixed liquid of toluene and hexane as an eluent to give 4.5 g (16.2 mmol) of colorless oily 2-chloro-9-phenylcarbazole (yield: 81%).

The thus-obtained compound was identified by $^1$H-NMR and $^{13}$C-NMR measurements.

$^1$H-NMR (CDCl$_3$); 8.08 (d, 1H), 8.01 (d, 1H), 7.16-7.64 (m, 10H)

$^{13}$C-NMR (CDCl$_3$); 141.40, 141.20, 137.04, 131.66, 130.01, 127.85, 127.06, 126.19, 122.72, 121.88, 121.11, 120.36, 120.23, 109.94, 109.87

Synthesis Example 6

Synthesis of 2-chloro-9-biphenylylcarbazole

In a stream of nitrogen, a 50 ml three-necked flask was charged with 4.0 g (19.8 mmol) of 2-chlorocarbazole obtained in Synthesis Example 2, 5.5 g (23.7 mmol) of 4-bromobiphenyl, 3.83 g (27.7 mmol) of potassium carbonate and 20 ml of o-xylene. To the thus-obtained reaction liquid of a slurry state, 44 mg (0.19 mmol) of palladium acetate and 0.14 g (0.69 mmol) of tri(tert-butyl)phosphine were added, and the mixture was stirred at 130° C. for 24 hours. The reaction mixture was cooled to room temperature, and the deposited precipitate was collected by filtration. The thus-obtained solid was washed with pure water and then with methanol, and dried under a reduced pressure. The dried solid was recrystallized from n-butanol to give 4.9 g (13.8 mmol) of 2-chloro-9-biphenylylcarbazole as a white powder (yield: 69%).

The thus-obtained compound was identified by $^1$H-NMR and $^{13}$C-NMR measurements.

$^1$H-NMR (CDCl$_3$); 8.07 (d, 1H), 8.00 (d, 1H), 7.77 (d, 2H), 7.65 (d, 2H), 7.54 (d, 2H), 7.21-7.41 (m, 8H)

$^{13}$C-NMR (CDCl$_3$); 141.38, 141.18, 140.72, 140.08, 136.17, 131.75, 128.99, 128.66, 127.74, 127.27, 127.16, 126.23, 122.82, 121.99, 121.19, 120.47, 120.29, 110.05, 109.98

Synthesis Example 7

Synthesis of 2-chloro-9-methylcarbazole

In a stream of nitrogen, a 200 ml three-necked flask was charged with 10.0 g (49.5 mmol) of 2-chlorocarbazole obtained in Synthesis Example 2, 8.4 g (59.4 mmol) of iodomethane, 11.2 g (49.5 mmol) of benzyltriethylammonium chloride and 100 ml of dimethylsulfoxide. To the mixture, 6.1 g of an aqueous 48% sodium hydroxide solution was added while being stirred. The mixture was maintained at 70° C. for 2 hours to conduct reaction. Then the reaction mixture was cooled to room temperature, and incorporated in 100 g of pure water. The thus-deposited precipitate was collected by filtration. The obtained white solid was washed with pure water, and dried under a reduced pressure. The dried solid was recrystallized from ethanol to give 6.5 g (30.2 mmol) of 2-chloro-9-methylcarbazole as a white powder (yield: 61%).

The thus-obtained compound was identified by $^1$H-NMR and $^{13}$C-NMR measurements.

$^1$H-NMR (CDCl$_3$); 7.99 (d, 1H), 7.90 (d, 1H), 7.12-7.49 (m, 5H), 3.70 (s, 3H)

$^{13}$C-NMR(CDCl$_3$); 141.44, 141.18, 131.39, 125.93, 122.21, 121.31, 121.02, 120.22, 119.36, 119.26, 108.61, 29.17

Synthesis Example 8

Synthesis of N-phenyl-N-[2-(9-biphenylyl)carbazolyl]amine

In a stream of nitrogen, a 200 ml three-necked flask was charged with 19.0 g (53.6 mmol) of 2-chloro-9-biphenylylcarbazole obtained in Synthesis Example 6, 7.4 g (80.4 mmol) of aniline, 7.21 g (75.0 mmol) of sodium tert-butoxide and 120 ml of o-xylene. To the thus-obtained reaction liquid of a slurry state, 120 mg (0.53 mmol) of palladium acetate and 378 mg (1.87 mmol) of tri(tert-butyl) phosphine were added, and the mixture was stirred at 130° C. for 12 hours. The reaction mixture was cooled to room temperature, and then 70 g of pure water was added and stirred. The reaction mixture was separated into an aqueous phase and an organic phase. The organic phase was washed with pure water and then with an aqueous saturated sodium chloride solution, and then dried over anhydrous magnesium sulfate. The dried product was concentrated under a reduced pressure to give a brown solid. The brown solid was recrystallized from o-xylene to give 16.8 g (3.0 mmol) of N-phenyl-N-[2-(9-biphenylyl)carbazolyl]amine as a white powder (yield: 76%).

The thus-obtained compound was identified by $^1$H-NMR and $^{13}$C-NMR measurements.

$^1$H-NMR (CDCl$_3$); 7.95-8.04 (m, 2H), 7.74 (d, 2H), 7.18-7.66 (m, 12H), 6.99-7.12 (m, 4H), 5.77 (br, 1H)

$^{13}$C-NMR (CDCl$_3$); 143.62, 142.19, 141.73, 141.02, 140.21, 136.79, 129.37, 128.95, 128.49, 127.63, 127.23, 127.14, 124.79, 123.77, 121.11, 120.71, 120.12, 119.45, 118.00, 117.27, 112.38, 109.63, 99.03

Synthesis Example 9

Synthesis of N-phenyl-N-[2-(9-methyl)carbazolyl]amine

In a stream of nitrogen, a 100 ml three-necked flask was charged with 4.0 g (18.6 mmol) of 2-chloro-9-methylcarbazole obtained in Synthesis Example 7, 3.4 g (37.2 mmol) of aniline, 2.5 g (26.0 mmol) of sodium tert-butoxide and 40 ml of o-xylene. To the thus-obtained reaction liquid of a slurry state, 41 mg (0.18 mmol) of palladium acetate and 131 mg (0.65 mmol) of tri(tert-butyl)phosphine were added, and the mixture was stirred at 130° C. for 8 hours. The reaction mixture was cooled to room temperature, and the 30 g of pure water was added and stirred. The reaction mixture was separated into an aqueous phase and an organic phase. The organic phase was washed with pure water and then with an aqueous saturated sodium chloride solution, and then dried over anhydrous magnesium sulfate. The dried product was concentrated under a reduced pressure to give a brown solid. The brown solid was purified by silica-gel column chromatography using a mixed liquid of toluene with hexane as an eluent to give 4.8 g (17.6 mmol) of N-phenyl-N-[2-(9-methyl)carbazolyl]amine as a white powder (yield: 94%).

The thus-obtained compound was identified by $^1$H-NMR and $^{13}$C-NMR measurements.

$^1$H-NMR (CDCl$_3$); 7.90-8.00 (m, 2H), 6.89-7.43 (m, 10H)

$^{13}$C-NMR (CDCl$_3$); 143.76, 142.30, 141.66, 141.15, 129.43, 124.50, 123.09, 121.11, 120.78, 119.39, 118.99, 117.60, 117.43, 111.54, 108.20, 97.47, 29.10

Example 17

Synthesis of Compound (C3) and Evaluation of Stability of Film

In a stream of nitrogen, a 50 ml three-necked flask was charged with 1.0 g (2.4 mmol) of N-phenyl-N-(2-(9-biphenylyl)carbazolyl)amine obtained in Synthesis Example 8, 0.27 g (1.1 mmol) of m-dibromobenzene, 309 mg (3.2 mmol) of sodium tert-butoxide and 8 ml of o-xylene. To the thus-obtained reaction liquid of a slurry state, 5 mg (0.02 mmol) of palladium acetate and 16 mg (0.08 mmol) of tri(tert-butyl)phosphine were added, and the mixture was stirred at 130° C. for 7 hours. The reaction mixture was cooled to room temperature, and then, 10 g of pure water was added to the reaction mixture and the mixture was stirred. The reaction mixture was separated into an aqueous phase and an organic phase. The organic phase was washed with pure water and then with an aqueous saturated sodium chloride solution, and then, the washed organic phase was dried over anhydrous magnesium sulfate. The dried organic phase was concentrated under a reduced pressure to give a brown solid. The brown solid was purified by silica-gel column chromatography using a mixed liquid of toluene with hexane as an eluent to give 0.7 g (0.78 mmol) of the compound (C3) as a glassy solid (yield: 67%).

The compound (C3) was identified by the measurement according to FDMS.

FDMS: 895

A thin film was formed on a glass sheet from the compound (C3) by vacuum deposition. Even when the film was left to stand for one month at room temperature, it did not become whitely clouded (i.e., not coagulated nor crystallized). The glass transition temperature (Tg) of the compound (C3) was 150° C., that is, higher than Tg (96° C.) of a conventional NPD material.

Example 18

Synthesis of Compound (C6) and Evaluation of Stability of Film

In a stream of nitrogen, a 50 ml three-necked flask was charged with 2.0 g (3.6 mmol) of 2-chloro-9-phenylcarbazole obtained in Synthesis Example 5, 2.5 g (7.4 mmol) of N-phenyl-N-[4-(9-carbazoyl)phenyl]amine, 1.0 g (10.4 mmol) of sodium tert-butoxide and 10 ml of o-xylene. To the thus-obtained reaction liquid of a slurry state, 16 mg (0.07 mmol) of palladium acetate and 52 mg (0.26 mmol) of tri(tert-butyl)phosphine were added, and the mixture was stirred at 130° C. for 20 hours. The reaction mixture was cooled to room temperature, and then, 10 g of pure water was added to the reaction mixture and the mixture was stirred. The reaction mixture was separated into an aqueous phase and an organic phase. The organic phase was washed with pure water and then with an aqueous saturated sodium chloride solution, and then, the washed organic phase was dried over anhydrous magnesium sulfate. The dried organic phase was concentrated under a reduced pressure to give a brown solid. The brown solid was purified by silica-gel column chromatography using a mixed liquid of toluene with hexane as an eluent to give 1.5 g (2.6 mmol) of the compound (C6) as a glassy solid (yield: 34%).

The compound (C6) was identified by the measurement according to FDMS.

FDMS: 575

A thin film was formed on a glass sheet by the same procedure as described in Example 17. Even when the film was left to stand for one month at room temperature, it did not become whitely clouded (i.e., not coagulated nor crystallized). The glass transition temperature (Tg) of the compound (C6) was 100° C., that is, higher than Tg (96° C.) of a conventional NPD material.

Example 19

Synthesis of Compound (D3) and Evaluation of Stability of Film

In a stream of nitrogen, a 50 ml three-necked flask was charged with 1.5 g (3.6 mmol) of N-phenyl-N-(2-(9-biphenylyl)carbazoyl)amine, 690 mg (1.7 mmol) of 4,4'-diiodobiphenyl, 457 mg (4.7 mmol) of sodium tert-butoxide and 10 ml of o-xylene. To the thus-obtained reaction liquid of a slurry state, 7 mg (0.03 mmol) of palladium acetate and 21 mg (0.10 mmol) of tri(tert-butyl)phosphine were added, and the mixture was stirred at 120° C. for 6 hours. The reaction mixture was cooled to room temperature, and then, 10 g of pure water was added to the reaction mixture and the mixture was stirred. The thus-deposited precipitate was collected by filtration. The obtained yellow solid was washed with pure water and then with ethanol, and dried under a reduced pressure. The dried solid was recrystallized from o-xylene to give 1.3 g (1.3 mmol) of the compound (D3) as a yellow powder (yield: 81%).

The compound (D3) was identified by the measurement according to FDMS.

FDMS: 971

A thin film was formed on a glass sheet from the compound (D3) by the same procedure as described in Example 17. Even when the film was left to stand for one month at room temperature, it did not become whitely clouded (i.e., not coagulated nor crystallized). The glass transition temperature (Tg) was 145° C., that is, higher than Tg (96° C.) of a conventional NPD material.

Example 20

Synthesis of Compound (D10) and Evaluation of Stability of Film

In a stream of nitrogen, a 50 ml three-necked flask was charged with 1.5 g (3.6 mmol) of N-phenyl-N-(2-(9-biphenylyl)carbazolyl)amine obtained in Synthesis Example 8, 385 mg (1.7 mmol) of 3,3'-dichlorobiphenyl, 457 mg (4.7 mmol) of sodium tert-butoxide and 10 ml of o-xylene. To the thus-obtained reaction liquid of a slurry state, 7 mg (0.03 mmol) of palladium acetate and 21 mg (0.10 mmol) of tri(tert-butyl)phosphine were added, and the mixture was stirred at 130° C. for 24 hours. The reaction mixture was cooled to room temperature, and then, 10 g of pure water was added to the reaction mixture and the mixture was stirred. The thus-deposited precipitate was collected by filtration. The obtained white solid was washed with water and then with ethanol, and then, dried under a reduced pressure. The dried solid was then recrystallized from o-xylene to give 1.1 g (1.1 mmol) of the compound (D10) as a white powder (yield: 63%).

The compound (D10) was identified by the measurement according to FDMS.

FDMS: 971

A thin film was formed on a glass sheet from the compound (D10) by the same procedure as described in Example 17. Even when the film was left to stand for one month at room temperature, it did not become whitely clouded (i.e., not coagulated nor crystallized). The glass transition temperature (Tg) of the compound (D10) was 134° C., that is, higher than Tg (96° C.) of a conventional NPD material.

Example 21

Synthesis of Compound (D14) and Evaluation of Stability of Film

In a stream of nitrogen, a 50 ml three-necked flask was charged with 2.0 g (4.8 mmol) of N-phenyl-N-(2-(9-biphenylyl)carbazolyl)amine obtained in Synthesis Example 8, 491 mg (2.2 mmol) of 3,4'-dichlorobiphenyl, 594 mg (6.1 mmol) of sodium tert-butoxide and 10 ml of o-xylene. To the thus-obtained reaction liquid of a slurry state, 10 mg (0.04 mmol) of palladium acetate and 31 mg (0.15 mmol) of tri(tert-butyl)phosphine were added, and the mixture was stirred at 130° C. for 24 hours. The reaction mixture was cooled to room temperature, and then, 10 g of pure water was added to the reaction mixture and the mixture was stirred. The reaction mixture was then separated into an aqueous phase and an organic phase. The organic phase was washed with pure water and then with an aqueous saturated sodium chloride solution, and then, the washed organic phase was dried over anhydrous magnesium sulfate. The dried organic phase was concentrated under a reduced pressure to give a brown solid. The brown solid was purified by silica-gel column chromatography using a mixed liquid of toluene with hexane as an eluent to give 1.7 g (1.7 mmol) of the compound (D14) as a glassy solid (yield: 79%).

The compound (D14) was identified by the measurement according to FDMS.

FDMS: 971

A thin film was formed on a glass sheet from the compound (D14) by the same procedure as described in Example 17. Even when the film was left to stand for one month at room temperature, it did not become whitely clouded (i.e., not coagulated nor crystallized). The glass transition temperature (Tg) of the compound (D14) was 138° C., that is, higher than Tg (96° C.) of a conventional electroluminescent material NPD.

Example 22

Synthesis of Compound (E7) and Evaluation of Stability of Film

In a stream of nitrogen, a 50 ml three-necked flask was charged with 4.0 g (14.6 mmol) of N-phenyl-N-(2-(9-methyl)carbazolyl)amine obtained in Synthesis Example 9, 1.99 g (6.6 mmol) of 4,4"-dichloro-m-terphenyl, 1.7 g (18.6 mmol) of sodium tert-butoxide and 20 ml of o-xylene. To the thus-obtained reaction liquid of a slurry state, 29 mg (0.13 mmol) of palladium acetate and 94 mg (0.46 mmol) of tri(tert-butyl)phosphine were added, and the mixture was stirred at 130° C. for 24 hours. The reaction mixture was cooled to room temperature, and then, 20 g of pure water was added to the reaction mixture and the mixture was stirred. The thus-deposited precipitate was collected by filtration. The obtained white solid was washed with water and then with ethanol, and then, dried under a reduced pressure. The dried solid was then recrystallized from o-xylene to give 3.8 g (4.9 mmol) of the compound (E7) as a white powder (yield: 74%).

The compound (E7) was identified by the measurement according to FDMS.

FDMS: 770

A thin film was formed on a glass sheet from the compound (E7) by the same procedure as described in Example 17. Even when the film was left to stand for one month at room temperature, it did not become whitely clouded (i.e., not coagulated nor crystallized). The glass transition temperature (Tg) of the compound (E7) was 138° C., that is, higher than Tg (96° C.) of a conventional NPD material.

Example 23

Evaluation of Ionization Potential of Compound (C3)

The compound (C3) was dissolved at a concentration of 0.001 mol/L in a tetrabutylammonium perchlorate solution in anhydrous dichloromethane having a concentration of 0.1 mol/L. Ionization potential of the compound (C3) was measured on the compound (C3) solution by means of cyclic volutammetry analysis. In the cyclic volutammmetry analysis, glassy carbon was used as a working electrode, a platinum wire was used as a counter electrode, a silver wire dipped with a solution of $AgNO_3$ in acetonitrile was used as a reference electrode, and ferrocene was used as a standard material.

The ionization potential of the compound (C3) was 0.39V vs. $Fc/Fc^+$, as expressed on a basis of the oxidation-reduction potential of ferrocene as reference standard. Thus, the ionization potential of the compound (C3) was approximately the same as that (0.31V vs. $Fc/Fc^+$) of NPD which is conventionally used as a hole transport material.

Example 24

Evaluation of Ionization Potential of Compound (C6)

Ionization potential of the compound (C6) was evaluated by the same procedure as described in Example 23. The ionization potential of the compound (C6) was 0.38V vs. $Fc/Fc^+$, and thus, approximately the same as that (0.31V vs. $Fc/Fc^+$) of NPD conventionally used as a hole transport material.

Example 25

Evaluation of Ionization Potential of Compound (D3)

Ionization potential of the compound (D3) was evaluated by the same procedure as described in Example 23. The ionization potential of the compound (D3) was 0.28V vs. Fc/Fc$^+$, and thus, approximately the same as that (0.31V vs. Fc/Fc$^+$) of NPD conventionally used as a hole transport material.

Example 26

Evaluation of Ionization Potential of Compound (D10)

Ionization potential of the compound (D10) was evaluated by the same procedure as described in Example 23. The ionization potential of the compound (D10) was 0.37V vs. Fc/Fc$^+$, and thus, approximately the same as that (0.31V vs. Fc/Fc$^+$) of NPD conventionally used as a hole transport material.

Example 27

Evaluation of Ionization Potential of Compound (D14)

Ionization potential of the compound (D14) was evaluated by the same procedure as described in Example 23. The ionization potential of the compound (D14) was 0.37V vs. Fc/Fc$^+$, and thus, approximately the same as that (0.31V vs. Fc/Fc$^+$) of NPD conventionally used as a hole transport material.

Example 28

Evaluation of Ionization Potential of Compound (E7)

Ionization potential of the compound (E7) was evaluated by the same procedure as described in Example 23. The ionization potential of the compound (E7) was 0.35V vs. Fc/Fc$^+$, and thus, approximately the same as that (0.31V vs. Fc/Fc$^+$) of NPD conventionally used as a hole transport material.

Comparative Example 5

Evaluation of Ionization Potential of Comparative Compound (b)

Ionization potential of a comparative compound (b), i.e., a carbazole compound having a structure such that an amino group is bonded to 3-positions of the two carbazole rings, which is represented by the chemical structure shown below, was evaluated by the same procedure as described in Example 23. The ionization potential of the comparative compound (b) was 0.15V vs. Fc/Fc$^+$, and thus, smaller than that (0.31V vs. Fc/Fc$^+$) of NPD conventionally used as a hole transport material.

Comparative Compound (b)

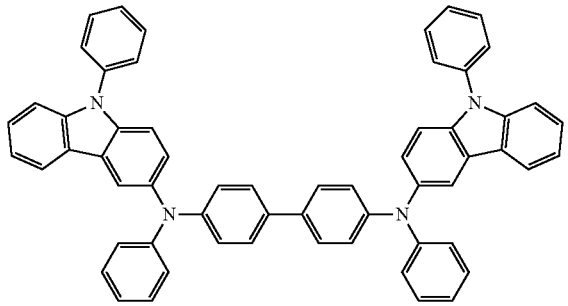

Example 29

Evaluation of Device Made by Using Compound (C3)

An organic EL device for evaluation was made as follows. A glass substrate having laminated thereon an indium-tin oxide (ITO) transparent electrode (anode) with a thickness of 200 nm was washed with acetone and then with pure water, while being irradiated with ultrasonic wave, and then washed with boiling isopropyl alcohol. The substrate was further treated by irradiation with ultraviolet rays while ozone was generated. The thus-treated glass substrate was placed in a vacuum evaporation chamber, and the inner pressure was reduced to $1\times10^{-4}$ Pa by a vacuum pump. Phthalocyanine copper was vapor-deposited at a deposition rate of 0.1 nm/sec on the transparent ITO electrode to form a hole injection layer with a thickness of 25 nm. Then the compound (C3) was vapor-deposited on the hole injection layer at a deposition rate of 0.3 nm/sec to form a hole transport layer with a thickness of 40 nm.

Alq$_3$ was vapor-deposited on the hole transport layer at a deposition rate of 0.3 nm/sec to form an emitting layer with a thickness of 60 nm, and then, lithium fluoride was vapor-deposited on the emitting layer at a deposition rate of 0.01 nm/sec to form an electron injection layer with a thickness of 0.5 nm. Further aluminum was vapor-deposited on the electron injection layer at a deposition rate of 0.25 nm/sec to form a cathode with a thickness of 100 nm. A thus-obtained assembly was encapsulated with a glass sheet and an UV-curable resin in an atmosphere of nitrogen gas to give an organic EL device for evaluation.

Driving voltage and external quantum efficiency of the organic EL device were measured at a current density of 20 mA/cm$^2$. The results are shown in Table 3, below.

Example 30

Evaluation of Device Made by Using Compound (C6)

An organic EL device for evaluation was made by the same procedure as described in Example 29 except that the compound (C6) was used instead of the compound (C3), and driving voltage and external quantum efficiency of the organic EL device were measured at a current density of 20 mA/cm$^2$. The results are shown in Table 3, below.

Example 31

Evaluation of Device Made by Using Compound (D3)

An organic EL device for evaluation was made by the same procedure as described in Example 29 except that the compound (D3) was used instead of the compound (C3), and driving voltage and external quantum efficiency of the organic EL device were measured at a current density of 20 mA/cm$^2$. The results are shown in Table 3, below.

Example 32

Evaluation of Device Made by Using Compound (D10)

An organic EL device for evaluation was made by the same procedure as described in Example 29 except that the compound (D10) was used instead of the compound (C3), and driving voltage and external quantum efficiency of the organic EL device were measured at a current density of 20 mA/cm$^2$. The results are shown in Table 3, below.

Example 33

Evaluation of Device Made by Using Compound (D14)

An organic EL device for evaluation was made by the same procedure as described in Example 29 except that the compound (D14) was used instead of the compound (C3), and driving voltage and external quantum efficiency of the organic EL device were measured at a current density of 20 mA/cm$^2$. The results are shown in Table 3, below.

Example 34

Evaluation of Device Made by Using Compound (E7)

An organic EL device for evaluation was made by the same procedure as described in Example 29 except that the compound (E7) was used instead of the compound (C3), and driving voltage and external quantum efficiency of the organic EL device were measured at a current density of 20 mA/cm$^2$. The results are shown in Table 3, below.

Comparative Example 6

An organic EL device for comparative evaluation was made by the same procedure as described in Example 29 except that NPD was used instead of the compound (C3), and driving voltage and external quantum efficiency of the organic EL device were measured at a current density of 20 mA/cm$^2$. The results are shown in Table 3, below.

Comparative Example 7

An organic EL device for comparative evaluation was made by the same procedure as described in Example 29 except that the comparative compound (b) was used instead of the compound (C3), and driving voltage and external quantum efficiency of the organic EL device were measured at a current density of 20 mA/cm$^2$. The results are shown in Table 3, below.

TABLE 3

|  | Compound in hole transport layer | Driving voltage (V) | External quantum efficiency (%) |
| --- | --- | --- | --- |
| Example 29 | (C3) | 5.4 | 1.01 |
| Example 30 | (C6) | 5.1 | 1.03 |
| Example 31 | (D3) | 5.3 | 1.05 |
| Example 32 | (D10) | 5.2 | 1.04 |
| Example 33 | (D14) | 5.3 | 0.99 |
| Example 34 | (E7) | 5.2 | 1.06 |
| Com. Ex. 6 | NPD | 5.8 | 0.92 |
| Com. Ex. 7 | Comparative comppound (b) | 6.0 | 0.76 |

Synthesis Example 10

Synthesis of 2-chloro-6-phenyl-N-phenylcarbazole

In a stream of nitrogen, a 200 ml three-necked flask was charged with 8.0 g (28.8 mmol) of 2-chloro-N-phenylylcarbazole obtained in Synthesis Example 5, and then, 160 mL of dichloromethane and 4.1 g (23.0 mmol) of N-bromosuccinimide were added to the content of the flask. The mixture was stirred at room temperature for 2 hours, and 100 mL of water was added to the reaction mixture. The reaction mixture was separated into an aqueous phase and an organic phase. The organic phase was washed with water and then with an aqueous saturated sodium chloride solution, and then dried over anhydrous magnesium sulfate. The dried organic phase was concentrated under a reduced pressure to give an oily product. The oily product was comprised of the starting compound, i.e., 2-chloro-N-phenylylcarbazole, and 2-chloro-6-bromo-N-phenylylcarbazole. The 2-chloro-6-bromo-N-phenylylcarbazole had a purity of 75%.

In a stream of nitrogen, a 100 ml three-necked flask was charged with 10 g of the above-mentioned mixture of 2-chloro-N-phenylylcarbazole and 2-chloro-6-bromo-N-phenylylcarbazole, 3.4 g (27.8 mmol) of phenylboric acid, 0.32 g (0.28 mmol) tetrakis(triphenylphosphine)palladium, 50 ml of tetrahydrofuran and 37 g (70.0 mmol) of an aqueous 20 weight % sodium carbonate solution were added to the content of the flask. The mixture was heated under reflux for 5 hours. Then the reaction mixture was cooled to room temperature, and separated into an aqueous phase and an organic phase. The organic phase was washed with an aqueous saturated ammonium chloride solution and then with an aqueous saturated sodium chloride solution, and then dried over anhydrous magnesium sulfate. The dried organic phase was concentrated under a reduced pressure, and the obtained residue was purified by silica-gel column chromatography using a mixed liquid of toluene and hexane as an eluent to give 6.5 g (18.4 mmol) of 2-chloro-6-phenyl-N-phenylcarbazole as white crystal (yield: 63%).

The thus-obtained compound was identified by $^1$H-NMR and $^{13}$C-NMR measurements.

$^1$H-NMR (CDCl$_3$); 8.28 (s, 1H), 8.06 (d, 1H), 7.23-7.71 (m, 14H)

$^{13}$C-NMR (CDCl$_3$); 141.82, 141.71, 140.65, 137.01, 133.97, 131.88, 130.07, 128.79, 127.93, 127.30, 126.99, 126.68, 125.75, 123.26, 122.01, 121.17, 120.55, 118.73, 110.20, 110.03

Example 35

Synthesis of Compound (F1) and Evaluation of Stability of Film

In a stream of nitrogen, a 50 ml three-necked flask was charged with 1.0 g (3.6 mmol) of 2-chloro-N-phenylcarbazole obtained in Synthesis Example 5, 1.1 g (3.6 mmol) of N,N-bis(4-biphenylyl)amine, 484 mg (5.0 mmol) of sodium tert-butoxide and 10 ml of o-xylene. To the thus-obtained reaction liquid of a slurry state, 8 mg (0.03 mmol) of palladium acetate and 25 mg (0.12 mmol) of tri(tert-butyl) phosphine were added, and the mixture was stirred at 130° C. for 24 hours. The reaction mixture was cooled to room temperature, and then, the deposited precipitate was collected by filtration. The thus-obtained solid was washed with water and then with ethanol, and then dried under a reduced pressure. The dried product was recrystallized from o-xylene to give 1.7 g (3.0 mmol) of the compound (F1) as a white powder (yield: 85%).

The compound (F1) was identified by was identified by FDMS, $^1$H-NMR and $^{13}$C-NMR measurements.

FDMS: 562

$^1$H-NMR (CDCl$_3$); 8.05 (d, 1H), 8.02 (d, 1H), 7.07-7.57 (m, 28H)

$^{13}$C-NMR (CDCl$_3$); 147.30, 145.93, 141.84, 141.38, 140.62, 137.45, 134.96, 129.88, 128.77, 127.72, 127.41, 126.86, 126.81, 126.62, 125.43, 123.64, 123.31, 121.15, 120.23, 119.87, 118.90, 109.72, 106.88

A thin film was formed on a glass sheet from the compound (F1) by vacuum deposition. Even when the film was left to stand for one month at room temperature, it did not become whitely clouded (i.e., not coagulated nor crystallized). The glass transition temperature (Tg) of the compound (F1) was 96° C. Even when the film on the glass sheet was heated to 90° C., it did not become whitely clouded.

Example 36

Synthesis of Compound (F8) and Evaluation of Stability of Film

In a stream of nitrogen, a 50 ml three-necked flask was charged with 1.2 g (3.6 mmol) of 2-chloro-N-(4-biphenylyl)carbazole obtained in Synthesis Example 6, 1.1 g (3.6 mmol) of N,N-bis(4-biphenylyl)amine, 484 mg (5.0 mmol) of sodium tert-butoxide and 10 ml of o-xylene. To the thus-obtained reaction liquid of a slurry state, 8 mg (0.03 mmol) of palladium acetate and 25 mg (0.12 mmol) of tri(tert-butyl)phosphine were added, and the mixture was stirred at 130° C. for 24 hours. The reaction mixture was cooled to room temperature, and 10 mL of water was added thereto to separate into an organic phase and an aqueous phase. The organic phase was washed with water and then with an aqueous saturated sodium chloride solution. Then the organic phase was dried over anhydrous magnesium sulfate. The dried organic phase was concentrated under a reduced pressure and the thus-obtained residue was purified by silica gel column chromatography using a mixed liquid of toluene and hexane as an eluent to give 1.6 g (2.5 mmol) of the compound (F8) as a glassy solid (yield: 72%).

The compound (F8) was identified by FDMS, $^1$H-NMR and $^{13}$C-NMR measurements.

FDMS: 638

$^1$H-NMR (CDCl$_3$); 8.08 (d, 1H), 8.04 (d, 1H), 7.71 (d, 2H), 7.10-7.62 (m, 30H)

$^{13}$C-NMR (CDCl$_3$); 147.30, 145.94, 141.81, 141.33, 140.58, 140.18, 140.10, 136.57, 134.94, 128.86, 128.73, 128.51, 127.71, 127.56, 127.08, 127.01, 126.77, 126.61, 125.45, 123.62, 123.37, 121.15, 120.29, 119.94, 119.87, 118.99, 109.80, 106.99

A thin film was formed on a glass sheet from the compound (F8) by the same procedure as described in Example 35. Even when the film was left to stand for one month at room temperature, it did not become whitely clouded (i.e., not coagulated nor crystallized). The glass transition temperature (Tg) of the compound (F8) was 119° C. Even when the film on the glass sheet was heated to 90° C., it did not become whitely clouded.

Example 37

Synthesis of Compound (F11) and Evaluation of Stability of Film

In a stream of nitrogen, a 50 ml three-necked flask was charged with 1.7 g (4.1 mmol) of N-phenyl-N-(2-(N-(4-biphenylyl))carbazolyl)amine obtained in Synthesis Example 8, 1.1 g (4.1 mmol) of 2-bromo-9,9-dimethylfluorene, 556 mg (5.7 mmol) of sodium tert-butoxide and 15 ml of o-xylene. To the thus-obtained reaction liquid of a slurry state, 9 mg (0.04 mmol) of palladium acetate and 29 mg (0.14 mmol) of tri(tert-butyl)phosphine were added, and the mixture was stirred at 130° C. for 3 hours. The reaction mixture was cooled to room temperature, and 10 mL of water was added thereto to separate into an organic phase and an aqueous phase. The organic phase was washed with water and then with an aqueous saturated sodium chloride solution. Then the organic phase was dried over anhydrous magnesium sulfate. The dried organic phase was concentrated under a reduced pressure and the thus-obtained residue was purified by silica-gel column chromatography using a mixed liquid of toluene and hexane as an eluent to give 2.1 g (3.5 mmol) of the compound (F11) as a glassy solid (yield: 85%).

The compound (F11) was identified by FDMS, $^1$H-NMR and $^{13}$C-NMR measurements.

FDMS: 602

$^1$H-NMR (CDCl$_3$); 7.99-8.08 (m, 2H), 7.49-7.68 (m, 8H), 7.14-7.45 (m, 15H), 6.99-7.08 (m, 3H), 1.39 (s, 6H)

$^{13}$C-NMR (CDCl$_3$); 154.82, 153.38, 148.21, 147.63, 146.55, 141.75, 141.26, 140.14, 140.10, 139.04, 136.59, 133.60, 129.13, 128.84, 128.44, 127.54, 127.06, 126.97, 126.30, 125.25, 124.02, 123.44, 122.54, 122.43, 120.95, 120.51, 120.22, 119.72, 119.32, 118.31, 117.73, 109.72, 105.91, 46.86, 27.17

A thin film was formed on a glass sheet from the compound (F11) by the same procedure as described in Example 35. Even when the film was left to stand for one month at room temperature, it did not become whitely clouded (i.e., not coagulated nor crystallized). The glass transition temperature (Tg) of the compound (F11) was 108° C. Even when the film on the glass sheet was heated to 90° C., it did not become whitely clouded.

Example 38

Synthesis of Compound (F31) and Evaluation of Stability of Film

In a stream of nitrogen, a 100 ml three-necked flask was charged with 4.3 g (21.4 mmol) of 2-chlorocarbazole obtained in Synthesis Example 2, 4.4 g (21.4 mmol) of 2-bromonaphthalene, 4.1 g (29.2 mmol) of potassium carbonate and 35 mL of o-xylene. To the thus-obtained reaction liquid of a slurry state, 48 mg (0.21 mmol) of palladium acetate and 148 mg (0.73 mmol) of tri(tert-butyl)phosphine were added, and the mixture was stirred at 130° C. for 12 hours. The reaction mixture was cooled to room temperature, and 50 mL of pure water was added thereto to separate into an organic phase and an aqueous phase. The organic phase was washed with water and then with an aqueous saturated sodium chloride solution to give a solution of 2-chloro-N-(2-naphthyl)carbazole in o-xylene.

Then a 100 ml three-necked flask was charged with the 2-chloro-N-(2-naphthyl) carbazole solution, and then, 6.8 g (21.4 mmol) of N,N-bis(4-biphenylyl)amine, 2.8 g (29.9 mmol) of sodium tert-butoxide and 35 mL of o-xylene were added to the content of the flask. To the thus-obtained reaction liquid of a slurry state, 48 mg (0.21 mmol) of palladium acetate and 148 mg (0.73 mmol) of tri(tert-butyl) phosphine were added, and the mixture was stirred at 130° C. for 14 hours. The reaction mixture was cooled to room temperature, and the deposited precipitate was collected by filtration. The obtained solid was washed with water and then with ethanol, and then dried under a reduced pressure. The dried product was recrystallized from o-xylene to give 8.1 g (13.3 mmol) of the compound (F31) as a white powder (yield: 620).

The thus-obtained compound was identified by FDMS, $^1$H-NMR and $^{13}$C-NMR measurements.

FDMS: 612

$^1$H-NMR (CDCl$_3$); 7.77-8.11 (m, 6H), 7.18-7.62 (m, 26H)

$^{13}$C-NMR (CDCl$_3$); 147.23, 146.05, 141.92, 141.44, 140.58, 135.01, 134.87, 133.86, 132.23, 129.83, 128.68, 127.82, 127.78, 127.69, 126.73, 126.61, 126.37, 125.38, 125.03, 124.89, 123.70, 123.40, 121.06, 120.27, 119.83, 119.78, 118.71, 109.69, 106.78

A thin film was formed on a glass sheet from the compound (F31) by the same procedure as described in Example 35. Even when the film was left to stand for one month at room temperature, it did not become whitely clouded (i.e., not coagulated nor crystallized). The glass transition temperature (Tg) of the compound (F31) was 101° C. Even when the film on the glass sheet was heated to 90° C., it did not become whitely clouded.

Example 39

Synthesis of Compound (F35) and Evaluation of Stability of Film

In a stream of nitrogen, a 50 ml three-necked flask was charged with 3.0 g (8.4 mmol) of 2-chloro-6-phenyl-N-phenylcarbazole obtained in Synthesis Example 10, 2.0 g (8.4 mmol) of N-phenyl-N-biphenylamine, 1.1 g (11.8 mmol) of sodium tert-butoxide and 30 mL of o-xylene. To the reaction mixture of a slurry state, 19 mg (0.08 mmol) of palladium acetate and 60 mg (0.29 mmol) of tri(tert-butyl) phosphine were added, and the mixture was stirred at 130° C. for 10 hours. The reaction mixture was then cooled to room temperature, and 15 mL of water was added thereto to effect phase separation into an organic phase and an aqueous phase. The organic phase was washed with water and then with an aqueous saturated sodium chloride solution, and then dried over magnesium sulfate. The dried product was concentrated under a reduced pressure. The obtained residue was purified by silica-gel column chromatography using a mixed liquid of toluene and hexane as an eluent to give 3.7 g (6.7 mmol) of the compound (F35) as a glassy solid (yield: 79%).

The thus-obtained compound (F35) was identified by FDMS, $^1$H-NMR and $^{13}$C-NMR measurements.

FDMS: 562

$^1$H-NMR (CDCl$_3$); 8.26 (s, 1H), 8.05 (d, 1H), 7.70 (d, 2H), 6.96-7.62 (m, 26H)

$^{13}$C-NMR (CDCl$_3$); 147.90, 147.41, 146.31, 142.24, 141.93, 140.80, 140.62, 137.39, 134.71, 133.66, 129.87, 129.15, 128.75, 128.71, 127.63, 127.41, 127.27, 126.73, 126.57, 124.83, 123.95, 123.86, 123.40, 122.63, 121.06, 119.67, 118.75, 118.26, 109.89, 106.63

A thin film was formed on a glass sheet from the compound (F35) by the same procedure as described in Example 35. Even when the film was left to stand for one month at room temperature, it did not become whitely clouded (i.e., not coagulated nor crystallized). The glass transition temperature (Tg) of the compound (F35) was 95° C. Even when the film on the glass sheet was heated to 90° C., it did not become whitely clouded.

Comparative Example 8

Evaluation of Stability of Film of Comparative Compound (c)

A thin film was formed on a glass sheet from a comparative compound (c) having a chemical structure shown below by the same procedure as described in Example 1. When the film was left to stand for one month at room temperature, it became whitely clouded. The glass transition temperature (Tg) of the comparative compound (c) was lower than 90° C. When the film on the glass sheet was heated to 90° C., it became whitely clouded.

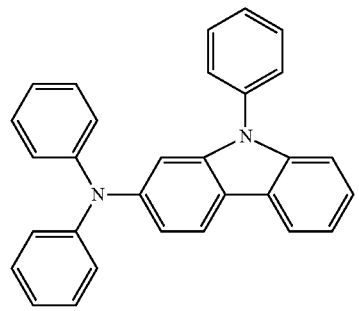

Comparative Compound (c)

Example 40

Evaluation of Ionization Potential of Compound (F1)

The compound (F1) was dissolved at a concentration of 0.001 mol/L in a tetrabutylammonium perchlorate solution in anhydrous dichloromethane having a concentration of 0.1 mol/L. Ionization potential of the compound (F1) was measured on the compound (F1) solution by means of cyclic volutammetry analysis. In the cyclic volutammmetry analysis, glassy carbon was used as a working electrode, a platinum wire was used as a counter electrode, a silver wire dipped with a solution of AgNO$_3$ in acetonitrile was used as a reference electrode, and ferrocene was used as a standard material.

The ionization potential of the compound (F1) was 0.35V vs. Fc/Fc$^+$, as expressed on a basis of the oxidation-reduction potential of ferrocene as reference standard. Thus, the ionization potential of the compound (F1) was approximately the same as that (0.31V vs. Fc/Fc$^+$) of NPD which is conventionally used as a hole transport material.

Example 41

Evaluation of Ionization Potential of Compound (F8)

Ionization potential of the compound (F8) was evaluated by the same procedure as described in Example 40. The ionization potential of the compound (F8) was 0.34V vs. Fc/Fc$^+$, and thus, approximately the same as that (0.31V vs. Fc/Fc$^+$) of NPD conventionally used as a hole transport material.

Example 42

Evaluation of Ionization Potential of Compound (F11)

Ionization potential of the compound (F11) was evaluated by the same procedure as described in Example 40. The ionization potential of the compound (F11) was 0.28V vs. Fc/Fc$^+$, and thus, approximately the same as that (0.31V vs. Fc/Fc$^+$) of NPD conventionally used as a hole transport material.

Example 43

Evaluation of Ionization Potential of Compound (F31)

Ionization potential of the compound (F31) was evaluated by the same procedure as described in Example 40. The ionization potential of the compound (F31) was 0.33V vs. Fc/Fc$^+$, and thus, approximately the same as that (0.31V vs. Fc/Fc$^+$) of NPD conventionally used as a hole transport material.

Example 44

Evaluation of Ionization Potential of Compound (F33)

Ionization potential of the compound (F33) was evaluated by the same procedure as described in Example 40. The ionization potential of the compound (F33) was 0.35V vs. Fc/Fc+, and thus, approximately the same as that (0.31V vs. Fc/Fc+) of NPD conventionally used as a hole transport material.

Example 45

Evaluation of Device Made by Using Compound (F1)

An organic EL device for evaluation was made as follows. A glass substrate having laminated thereon an indium-tin oxide (ITO) transparent electrode (anode) with a thickness of 200 nm was washed with acetone and then with pure water, while being irradiated with ultrasonic wave, and then washed with boiling isopropyl alcohol. The substrate was further treated by irradiation with ultraviolet rays while ozone was generated. The thus-treated glass substrate was placed in a vacuum evaporation chamber, and the inner pressure was reduced to $1 \times 10^{-4}$ Pa by a vacuum pump. Phthalocyanine copper was vapor-deposited at a deposition rate of 0.1 nm/sec on the transparent ITO electrode to form a hole injection layer with a thickness of 25 nm. Then the compound (F1) was vapor-deposited on the hole injection layer at a deposition rate of 0.3 nm/sec to form a hole transport layer with a thickness of 40 nm. Alq$_3$ was vapor-deposited on the hole transport layer at a deposition rate of 0.3 nm/sec to form an emitting layer with a thickness of 60 nm, and then, lithium fluoride was vapor-deposited on the emitting layer at a deposition rate of 0.01 nm/sec to form an electron injection layer with a thickness of 0.5 nm. Further aluminum was vapor-deposited on the electron injection layer at a deposition rate of 0.25 nm/sec to form a cathode with a thickness of 100 nm. A thus-obtained assembly was encapsulated with a glass sheet and an UV-curable resin in an atmosphere of nitrogen gas to give an organic EL device for evaluation.

Driving voltage and external quantum efficiency of the organic EL device were measured at a current density of 20 mA/cm$^2$. The results are shown in Table 4, below.

Example 46

Evaluation of Device Made by Using Compound (F8)

An organic EL device for evaluation was made by the same procedure as described in Example 45 except that the compound (F8) was used instead of the compound (F1), and driving voltage and external quantum efficiency of the organic EL device were measured at a current density of 20 mA/cm$^2$. The results are shown in Table 4, below.

Example 47

Evaluation of Device Made by Using Compound (F11)

An organic EL device for evaluation was made by the same procedure as described in Example 45 except that the compound (F11) was used instead of the compound (F1), and driving voltage and external quantum efficiency of the organic EL device were measured at a current density of 20 mA/cm$^2$. The results are shown in Table 4, below.

Example 48

Evaluation of Device Made by Using Compound (F31)

An organic EL device for evaluation was made by the same procedure as described in Example 45 except that the compound (F31) was used instead of the compound (F1), and driving voltage and external quantum efficiency of the organic EL device were measured at a current density of 20 mA/cm$^2$. The results are shown in Table 4, below.

Example 49

Evaluation of Device Made by Using Compound (F33)

An organic EL device for evaluation was made by the same procedure as described in Example 45 except that the compound (F33) was used instead of the compound (F1), and driving voltage and external quantum efficiency of the organic EL device were measured at a current density of 20 mA/cm$^2$. The results are shown in Table 4, below.

Comparative Example 9

An organic EL device for evaluation was made by the same procedure as described in Example 45 except that NPD was used instead of the compound (F1), and driving voltage and external quantum efficiency of the organic EL device were measured at a current density of 20 mA/cm$^2$. The results are shown in Table 4, below.

Comparative Example 10

An organic EL device for evaluation was made by the same procedure as described in Example 45 except that the comparative compound (a) shown in Comparative Example 1 was used instead of the compound (F1), and driving voltage and external quantum efficiency of the organic EL device were measured at a current density of 20 mA/cm$^2$. The results are shown in Table 4, below.

TABLE 4

| | Compound in hole transport layer | Driving voltage (V) | External quantum efficiency (%) |
|---|---|---|---|
| Example 45 | (F1) | 5.5 | 1.00 |
| Example 46 | (F8) | 5.4 | 1.03 |
| Example 47 | (F11) | 5.3 | 0.99 |
| Example 48 | (F31) | 5.2 | 0.97 |
| Example 49 | (F33) | 5.4 | 1.02 |
| Com. Ex. 9 | NPD | 5.8 | 0.92 |
| Com. Ex. 10 | Comparative comppound (a) | 6.0 | 0.81 |

Example 50

Evaluation of Device Made by Using Compound (F1)

An organic EL device for evaluation was made as follows. A glass substrate having laminated thereon an indium-tin oxide (ITO) transparent electrode (anode) with a thickness of 200 nm was washed with acetone and then with pure water, while being irradiated with ultrasonic wave, and then washed with boiling isopropyl alcohol. The substrate was further treated by irradiation with ultraviolet rays while ozone was generated. The thus-treated glass substrate was placed in a vacuum evaporation chamber, and the inner pressure was reduced to $1 \times 10^{-4}$ Pa by a vacuum pump. NPD was vapor-deposited at a deposition rate of 0.3 nm/sec on the transparent ITO electrode to form a hole injection layer with a thickness of 20 nm. Then the compound (F1) was vapor-deposited on the hole injection layer at a deposition rate of 0.3 nm/sec to form a hole transport layer with a thickness of 30 nm.

Then Ir(ppy)$_3$ as a phospholuminous dopant material and CBP as a host material were co-vapor-deposited on the hole transport layer at a weight ratio of 1:11.5 and at a deposition rate of 0.25 nm/sec to form an emitting layer with a thickness of 20 nm. Then 2,9-dimethyl-4,7-diphenyl-1,10-phenanthroline (BCP) was vapor-deposited on the emitting layer at a deposition rate of 0.3 nm/sec to form an exciton blocking layer with a thickness of 10 nm. Alq$_3$ was vapor-deposited on the exciton blocking layer at a deposition rate of 0.3 nm/sec to form an electron transport layer with a thickness of 30 nm. Then lithium fluoride was vapor-deposited on the electron transport layer at a deposition rate of 0.01 nm/sec to form an electron injection layer with a thickness of 0.5 nm. Further aluminum was vacuum-deposited on the electron injection layer at a deposition rate of 0.25 nm/sec to form a cathode with a thickness of 100 nm. A thus-obtained assembly was encapsulated with a glass sheet and an UV-curable resin in an atmosphere of nitrogen gas to give an organic EL device for evaluation.

Driving voltage and external quantum efficiency of the organic EL device were measured at a current density of 20 mA/cm$^2$. The results are shown in Table 5, below.

Example 51

Evaluation of Device Made by Using Compound (F8)

An organic EL device for evaluation was made by the same procedure as described in Example 50 except that the compound (F8) was used instead of the compound (F1), and driving voltage and external quantum efficiency of the organic EL device were measured at a current density of 20 mA/cm$^2$. The results are shown in Table 5, below.

Example 52

Evaluation of Device Made by Using Compound (F11)

An organic EL device for evaluation was made by the same procedure as described in Example 50 except that the compound (F11) was used instead of the compound (F1), and driving voltage and external quantum efficiency of the organic EL device were measured at a current density of 20 mA/cm$^2$. The results are shown in Table 5, below.

Example 53

Evaluation of Device Made by Using Compound (F31)

An organic EL device for evaluation was made by the same procedure as described in Example 50 except that the compound (F31) was used instead of the compound (F1), and driving voltage and external quantum efficiency of the organic EL device were measured at a current density of 20 mA/cm$^2$. The results are shown in Table 5, below.

Example 54

Evaluation of Device Made by Using Compound (F33)

An organic EL device for evaluation was made by the same procedure as described in Example 50 except that the compound (F33) was used instead of the compound (F1), and driving voltage and external quantum efficiency of the organic EL device were measured at a current density of 20 mA/cm$^2$. The results are shown in Table 5, below.

Comparative Example 11

An organic EL device for evaluation was made by the same procedure as described in Example 50 except that NPD was used instead of the compound (F1), and driving voltage and external quantum efficiency of the organic EL device were measured at a current density of 20 mA/cm$^2$. The results are shown in Table 5, below.

Comparative Example 12

An organic EL device for evaluation was made by the same procedure as described in Example 50 except that a comparative compound (d) having a chemical structure shown below was used instead of the compound (F1). Driving voltage and external quantum efficiency of the organic EL device were measured at a current density of 20 mA/cm$^2$. The results are shown in Table 5, below.

Comparative Compound (d)

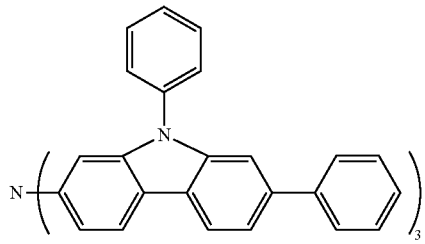

TABLE 5

|  | Compound in hole transport layer | Driving voltage (V) | External quantum efficiency (%) |
| --- | --- | --- | --- |
| Example 50 | (F1) | 8.2 | 11.9 |
| Example 51 | (F8) | 8.3 | 11.8 |
| Example 52 | (F11) | 8.3 | 10.9 |
| Example 53 | (F31) | 8.4 | 10.5 |
| Example 54 | (F33) | 8.5 | 11.5 |
| Com. Ex. 11 | NPD | 8.8 | 8.70 |
| Com. Ex. 12 | Comparative comppound (d) | 8.2 | 8.65 |

INDUSTRIAL APPLICABILITY

The carbazole compound of the formula (1) according to the present invention can be used for a light emitting layer, a hole transport layer or a hole injection layer of an organic EL device.

Especially the carbazole compound of the formula (1) has excellent hole transporting characteristics, therefore, an organic EL device having a hole transport layer and/or a hole injection layer comprising the carbazole compound of the formula (1) can be operated at a low drive voltage, and exhibits high luminescence efficiency and enhanced durability.

Further the carbazole compound of the formula (1) has a high triplet level as compared with the conventional material, therefore, high luminescence efficiency can be achieved in the organic EL device having an emitting layer comprised of not only a fluorescent material but also a phosphorescent material.

In the case when the carbazole compound of the formula (1) is used for a light emitting layer of an organic EL device, the light emitting layer can be formed either from the carbazole compound of the formula (1) alone, or from a combination of the carbazole compound of the formula (1) with a conventional luminescent host material, such as a conventional luminescent host material doped with the carbazole compound of the formula (1), or the carbazole compound of the formula (1) doped with a conventional luminescent host material. The carbazole compound of the formula (1) has high triplet level, therefore, it is especially suitable for a luminescent host material of an organic EL device using a phosphorescent material.

A hole injection layer, a hole transport layer and a light emitting layer, which comprise the carbazole compound of the formula (1), can be formed by any known method including, for example, vacuum deposition, spin coating and casting methods.

The invention claimed is:

1. A carbazole compound represented by the following general formula (12):

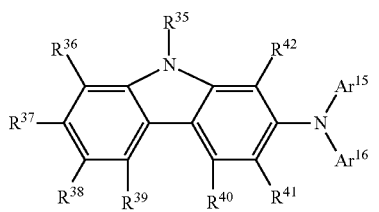

(12)

wherein:
$Ar^{15}$ and $Ar^{16}$ in the formula (12) independently represent a methyl-substituted or unsubstituted 4-biphenylyl group, a methyl-substituted or unsubstituted 3-biphenylyl group, a methyl-substituted or unsubstituted m-terphenylyl group, or a methyl-substituted or unsubstituted 2-fluorenyl group;

$R^{35}$ represents a straight-chain, branched or cyclic alkyl group having 1 to 18 carbon atoms, a substituted or unsubstituted biphenylyl group, a substituted or unsubstituted terphenylyl group, a substituted or unsubstituted naphthyl group, a substituted or unsubstituted phenanthryl group, a substituted or unsubstituted anthryl group, a substituted or unsubstituted fluoranthenyl group, a substituted or unsubstituted perylenyl group, a substituted or unsubstituted pyrenyl group, a substituted or unsubstituted pycenyl group, a substituted or unsubstituted chrysenyl group, or a substituted or unsubstituted heteroaryl group having 4 to 50 carbon atoms;

$R^{37}$ represents a hydrogen atom, a halogen atom, a straight-chain, branched or cyclic alkyl group having 1 to 18 carbon atoms, or a straight-chain, branched or cyclic alkoxy group having 1 to 18 carbon atoms; and $R^{36}$ and $R^{38}$ through $R^{42}$ independently represent a hydrogen atom, a halogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 50 carbon atoms, or a substituted or unsubstituted heteroaryl group having 4 to 50 carbon atoms.

* * * * *